United States Patent
Sun et al.

(10) Patent No.: US 11,174,329 B2
(45) Date of Patent: *Nov. 16, 2021

(54) MULTI- OR DUAL-HEADED COMPOSITIONS USEFUL FOR CHAIN SHUTTLING AND PROCESS TO PREPARE THE SAME

(71) Applicant: Dow Global Technologies LLC, Midland, MI (US)

(72) Inventors: Lixin Sun, Sugar Land, TX (US); Zhe Zhou, Lake Jackson, TX (US); Jaclyn Murphy, Ashland, MA (US); Edmund M. Carnahan, Pearland, TX (US)

(73) Assignee: Dow Global Technologies LLC, Midland, MI (US)

( * ) Notice: Subject to any disclaimer, the term of this patent is extended or adjusted under 35 U.S.C. 154(b) by 250 days.

This patent is subject to a terminal disclaimer.

(21) Appl. No.: 16/338,232

(22) PCT Filed: Sep. 29, 2017

(86) PCT No.: PCT/US2017/054458
§ 371 (c)(1),
(2) Date: Mar. 29, 2019

(87) PCT Pub. No.: WO2018/064553
PCT Pub. Date: Apr. 5, 2018

(65) Prior Publication Data
US 2019/0225719 A1 Jul. 25, 2019

Related U.S. Application Data

(60) Provisional application No. 62/402,060, filed on Sep. 30, 2016.

(51) Int. Cl.
| | |
|---|---|
| *C08F 4/10* | (2006.01) |
| *C08F 4/52* | (2006.01) |
| *C08F 110/02* | (2006.01) |
| *C08F 12/34* | (2006.01) |
| *C07C 13/465* | (2006.01) |

(52) U.S. Cl.
CPC .......... *C08F 110/02* (2013.01); *C07C 13/465* (2013.01); *C08F 12/34* (2013.01); *C07C 2602/24* (2017.05); *C08F 4/10* (2013.01); *C08F 4/52* (2013.01); *C08F 2410/01* (2013.01); *C08F 2410/03* (2013.01)

(58) Field of Classification Search
CPC ...... C08F 4/10; C08F 4/50; C08F 4/52; C08F 4/54
See application file for complete search history.

(56) References Cited

U.S. PATENT DOCUMENTS

| | | |
|---|---|---|
| 4,543,399 A | 9/1985 | Jenkins, III et al. |
| 4,588,790 A | 5/1986 | Jenkins, III et al. |
| 5,028,670 A | 7/1991 | Chinh et al. |
| 5,032,562 A | 7/1991 | Lo et al. |
| 5,064,802 A | 11/1991 | Stevens et al. |
| 5,106,804 A | 4/1992 | Bailly et al. |
| 5,153,157 A | 10/1992 | Hlatky et al. |
| 5,272,236 A | 12/1993 | Lai et al. |
| 5,278,272 A | 1/1994 | Lai et al. |
| 5,296,433 A | 3/1994 | Siedle et al. |
| 5,321,106 A | 6/1994 | LaPointe |
| 5,350,723 A | 9/1994 | Neithamer et al. |
| 5,352,749 A | 10/1994 | DeChellis et al. |
| 5,405,922 A | 4/1995 | DeChellis et al. |
| 5,425,872 A | 6/1995 | Devore et al. |
| 5,436,304 A | 7/1995 | Griffin et al. |
| 5,453,410 A | 9/1995 | Kolthammer et al. |
| 5,453,471 A | 9/1995 | Bernier et al. |
| 5,461,123 A | 10/1995 | Song et al. |
| 5,462,999 A | 10/1995 | Griffin et al. |
| 5,470,993 A | 11/1995 | Devore et al. |
| 5,473,028 A | 12/1995 | Nowlin et al. |
| 5,541,270 A | 7/1996 | Chinh et al. |
| 5,556,238 A | 9/1996 | Chinh et al. |
| 5,608,019 A | 3/1997 | Cheruvu et al. |
| 5,612,271 A | 3/1997 | Zandona |
| 5,616,661 A | 4/1997 | Eisinger et al. |
| 5,625,087 A | 4/1997 | Devore et al. |

(Continued)

FOREIGN PATENT DOCUMENTS

| | | |
|---|---|---|
| EP | 0277003 A1 | 8/1988 |
| EP | 2459598 A2 | 6/2012 |

(Continued)

OTHER PUBLICATIONS

Makio, H.; Ochiai, T.; Mohri, J.; Takeda, K.; Shimizaki, T.; Usui, Y.; Matsuura, S.; Fujita, T. J.Am.Chem.Soc. 2013, 135, 8177-8180. (Year: 2013).*
F. Freijee et al., J. Organomet. Chem. 224, 217-221, 1982.
A. Prasad et al., J. Organomet. Chem., 562, 133-139, 1998.
H. Makio et al., J. Am. Chem. Soc., 135, 8177?8180, 2013.
G. Herberich, et al., in Organometallics, 14,1, 471-480 (1995).
Kaminski, et al., J. Mol. Catal. A: Chemical, 102 (1995) 59-65.
Zambelli, et al., Macromolecules, 1988, 21, 617- 622.
Dias, et al., J. Mol. Catal. A: Chemical, 185 (2002) 57-64.
Brookhart, et al., J. Am. Chem. Soc., 1995, 117, 64145-6415.

(Continued)

*Primary Examiner* — Rip A Lee

(74) *Attorney, Agent, or Firm* — Cheney Huang

(57) ABSTRACT

The present disclosure relates to a multi- or dual-headed composition having the formula (I) or (II). The present disclosure also relates to a process for preparing the multi- or dual-headed composition having the formula (I) or (II), the process including combining 1,2,4-trivinylcyclohexane, an organometallic compound, and a catalyst precursor. The present disclosure further relates to use of the composition having the formula (I) or (II) in olefin polymerization.

9 Claims, 7 Drawing Sheets

(56) References Cited

U.S. PATENT DOCUMENTS

| | | |
|---|---|---|
| 5,648,310 A | 7/1997 | Wasserman et al. |
| 5,665,800 A | 9/1997 | Lai et al. |
| 5,672,669 A | 9/1997 | Wasserman et al. |
| 5,719,095 A | 2/1998 | Brekner et al. |
| 5,721,185 A | 2/1998 | LaPointe et al. |
| 5,783,512 A | 7/1998 | Jacobsen et al. |
| 5,849,852 A | 12/1998 | Koch et al. |
| 5,859,653 A | 1/1999 | Aoki et al. |
| 5,866,704 A | 2/1999 | Nickias et al. |
| 5,869,723 A | 2/1999 | Hinokuma et al. |
| 5,883,204 A | 3/1999 | Spencer et al. |
| 5,919,983 A | 7/1999 | Rosen et al. |
| 5,977,251 A | 11/1999 | Kao et al. |
| 6,015,868 A | 1/2000 | Nickias et al. |
| 6,034,022 A | 3/2000 | McAdon et al. |
| 6,103,657 A | 8/2000 | Murray |
| 6,140,521 A | 10/2000 | Chen et al. |
| 6,150,297 A | 11/2000 | Campbell, Jr. et al. |
| 6,160,146 A | 12/2000 | Chen et al. |
| 6,214,760 B1 | 4/2001 | Chen et al. |
| 6,268,444 B1 | 7/2001 | Klosin et al. |
| 6,319,989 B1 | 11/2001 | Anderson et al. |
| 6,320,005 B1 | 11/2001 | Murray |
| 6,395,671 B2 | 5/2002 | LaPointe |
| 6,500,908 B1 | 12/2002 | Bohnen et al. |
| 6,515,155 B1 | 2/2003 | Klosin et al. |
| 6,555,634 B1 | 4/2003 | Klosin et al. |
| 6,683,149 B2 | 1/2004 | Jain et al. |
| 6,696,379 B1 | 2/2004 | Carnahan et al. |
| 7,355,089 B2 | 4/2008 | Chang et al. |
| 7,897,698 B2 | 3/2011 | Johannsen et al. |
| 7,947,793 B2 | 5/2011 | Marchand et al. |
| 7,989,551 B2 | 8/2011 | Arriola et al. |
| 8,058,373 B2 | 11/2011 | Stevens et al. |
| 8,293,859 B2 | 10/2012 | Marchand et al. |
| 8,476,366 B2 | 7/2013 | Walton et al. |
| 8,501,885 B2 * | 8/2013 | Arriola ................. C07F 5/062 526/183 |
| 8,563,658 B2 | 10/2013 | Walton et al. |
| 8,686,087 B2 | 4/2014 | Li Pi Shan et al. |
| 8,716,400 B2 | 5/2014 | Carnahan et al. |
| 8,785,554 B2 | 7/2014 | Li Pi Shan et al. |
| 8,822,598 B2 | 9/2014 | Li Pi Shan et al. |
| 8,822,599 B2 | 9/2014 | Li Pi Shan et al. |
| 10,723,816 B2 * | 7/2020 | Sun ........................ C07F 3/06 |
| 2003/0004286 A1 | 1/2003 | Klosin et al. |
| 2004/0220050 A1 | 11/2004 | Frazier et al. |
| 2006/0199930 A1 | 9/2006 | Li Pi Shan et al. |
| 2007/0167578 A1 | 7/2007 | Arriola et al. |
| 2008/0311812 A1 | 12/2008 | Arriola et al. |
| 2012/0101289 A1 | 4/2012 | Ochiai et al. |
| 2019/0339760 A1 * | 11/2019 | Egger ................... G06F 1/3296 |
| 2020/0024380 A1 * | 1/2020 | Sun ....................... C08F 4/65908 |
| 2020/0332045 A1 * | 10/2020 | Sun ....................... C07F 7/0805 |

FOREIGN PATENT DOCUMENTS

| | | |
|---|---|---|
| WO | 2004/024740 | 3/1970 |
| WO | 1998/007515 A1 | 2/1998 |
| WO | 1998/009996 A1 | 3/1998 |
| WO | 1998/032775 A1 | 7/1998 |
| WO | 1998/050392 A1 | 11/1998 |
| WO | 1999/015534 A1 | 4/1999 |
| WO | 1999/042467 A1 | 8/1999 |
| WO | 2002/002577 | 1/2002 |
| WO | 2002/038628 | 5/2002 |
| WO | 2002/092610 A1 | 11/2002 |
| WO | 2003/010171 A1 | 2/2003 |
| WO | 2003/040195 | 5/2003 |
| WO | 2003/078480 A2 | 9/2003 |
| WO | 2003/078483 A1 | 9/2003 |
| WO | 2005/090426 A1 | 9/2005 |
| WO | 2005/090427 | 9/2005 |
| WO | 2007/035485 A1 | 3/2007 |
| WO | 2009/012215 A1 | 1/2009 |
| WO | 2010/022228 A2 | 2/2010 |
| WO | 2011/016991 A2 | 2/2011 |
| WO | 2014/105411 A1 | 7/2014 |
| WO | 2016/028957 A1 | 2/2016 |
| WO | 2016/028970 A1 | 2/2016 |
| WO | 2018064540 | 4/2018 |

OTHER PUBLICATIONS

Johnson, J. Am. Chem. Soc., 118, 267-268 (1996).
Johnson, J. Am. Chem. Soc., 117, 6414-6415 (1995).
Feldman, Organometallics, 16, 1514-1516, (1997).
Lambert, J. Chem. Soc. Chem. Comm. 1993, 383-384.
Lambert, J. B., et al., Organometallics 1994, 13, 2430-2443.
Rudin, A., Modern Methods of Polymer Characterization, John Wiley & Sons, New York (1991) pp. 103-112.
Williams and Ward, J. Polym. ScL, Polym. Let., 6, 621 (1968).
PCT/US2017/054458, International Preliminary Report on Patentability dated Nov. 4, 2019.
PCT/US2017/054458, International Search Report and Written Opinion dated Jul. 12, 2017.

* cited by examiner

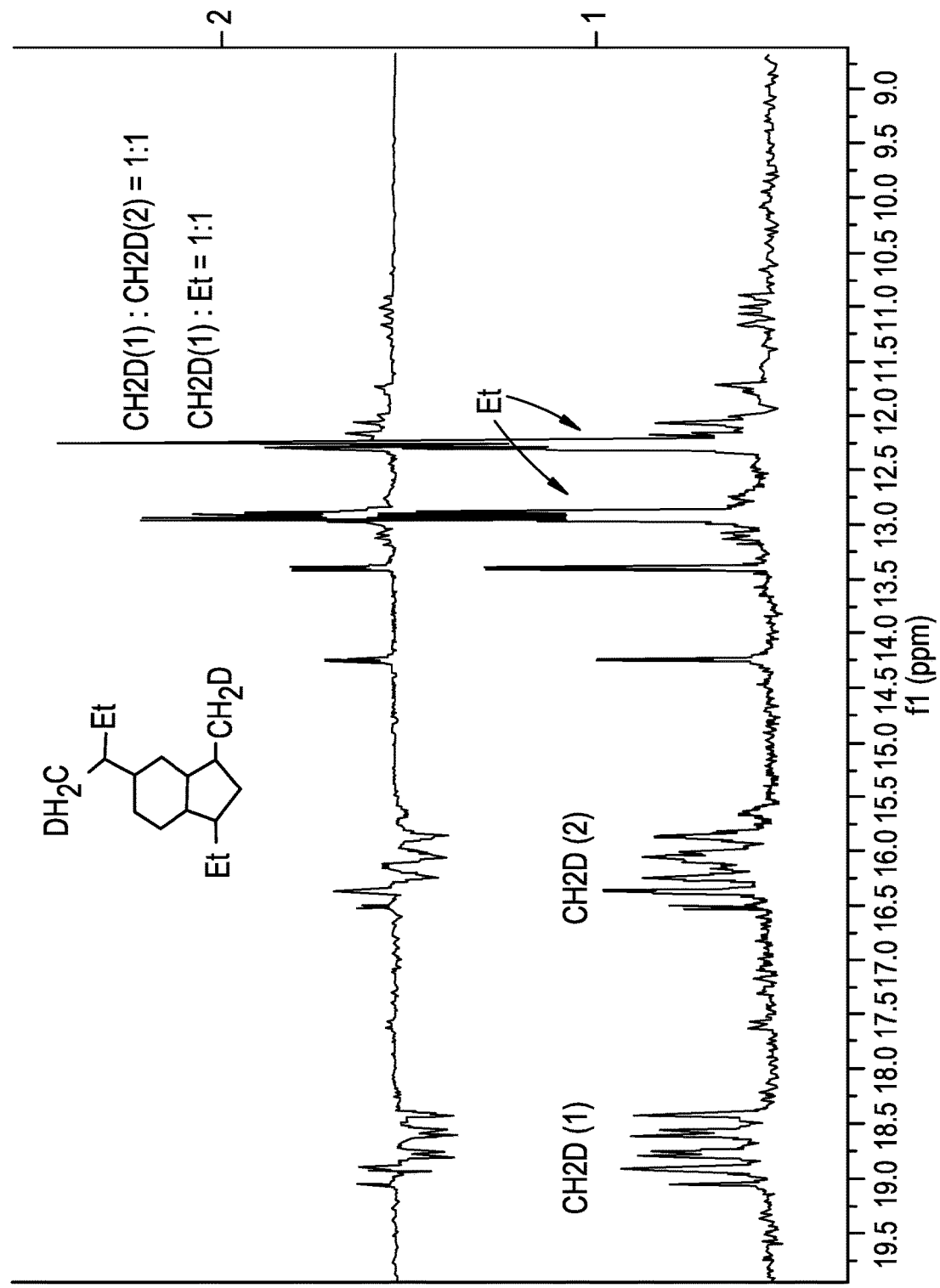

MULTI- OR DUAL-HEADED COMPOSITIONS USEFUL FOR CHAIN SHUTTLING AND PROCESS TO PREPARE THE SAME

FIELD

Embodiments relate to multi- or dual-headed compositions useful for chain shuttling and a process to prepare the same. In one aspect, the compositions can be used in olefin polymerization.

INTRODUCTION

The properties and applications of polyolefins depend to varying degrees upon the specific features of the catalysts used in their preparation. Specific catalyst compositions, activation conditions, steric and electronic features, and the like all can factor into the characteristics of the resulting polymer product. Indeed, a multitude of polymer features such as co-monomer incorporation, molecular weight, polydispersity, and long-chain branching, and the related physical properties, such as density, modulus, melt properties, tensile features, and optical properties, can all be affected by catalyst design.

In recent years, advances in polymer design have been seen with the use of compositions useful for chain shuttling. Such compositions have reversible chain transfer ability which can exchange a growing polymer chain between different catalytic sites such that portions of a single polymer molecule are synthesized by at least two different catalysts. These compositions also can extend the lifetime of a growing polymer chain such that sections of the polymer chain can be made in more than one zone or reactor under different process conditions. Currently, the best known compositions useful for chain shuttling are simple metal alkyls that typically contain only a single point of attachment to the metal for each polymer chain, such as diethyl zinc which produces polymer chains terminated with zinc metal at one end. More sophisticated compositions useful for chain shuttling, such as multi- or dual-headed chain shuttling agents (CSAs), with the alkane moiety attached to two metals, are also known. Indeed, multi- or dual-headed CSAs are of great interest since they can enable the production of new polyolefins, such as telechelic functional polymers.

While feasible methods to synthesize multi- or dual-headed CSAs have been reported, there is still a need for a commercially viable process for producing such compositions that is not hindered by high costs and tedious, complex procedures.

SUMMARY

In certain embodiments, the present disclosure relates to a composition having the formula (I) or (II):

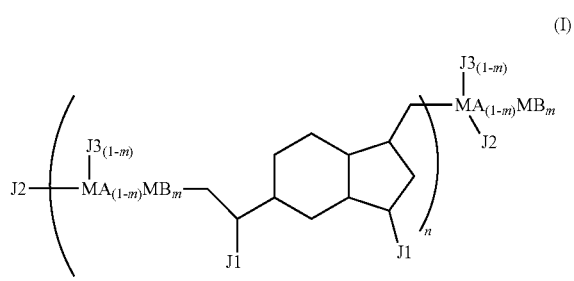

(I)

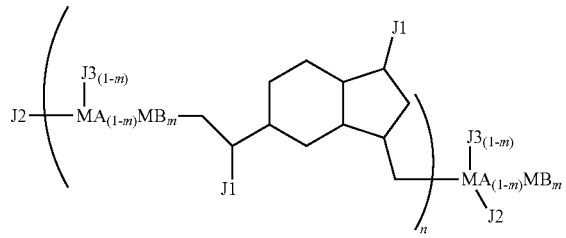

(II)

wherein:
each MA is Al, B, or Ga;
each MB is Zn or Mg;
m is a number from 0 to 1;
n is a number from 1 to 100; and
each J1, J2, and J3 is hydrogen or a $C_{1-20}$ alkyl group, and wherein J1, J2, and J3 may be the same or different, or mixtures thereof.

In certain embodiments, the present disclosure relates to a process for preparing the composition having the formula (I) or (II) by combining 1,2,4-trivinylcyclohexane (TVCH) and an organometallic compound in the presence of a catalyst precursor. In certain embodiments, the present disclosure relates to a process for preparing the composition having the formula (I) or (II) comprising: (a) combining TVCH, an organometallic compound, a co-catalyst, a solvent, and a first catalyst precursor; and (b) obtaining a final solution comprising the composition having the formula (I) or (II).

In certain embodiments, the present disclosure relates to a polymerization process for preparing a polymer composition, the process comprising: contacting at least one olefin monomer with a catalyst composition; wherein the catalyst composition comprises the reaction product of a second catalyst precursor, a co-catalyst, and the composition having the formula (I) or (II).

In certain embodiments, the present disclosure relates to a polymerization process for preparing a polymer composition, the process comprising: contacting at least one olefin monomer with a catalyst composition; wherein the catalyst composition comprises the reaction product of a second catalyst precursor, a co-catalyst, and the composition having the formula (I) or (II), and wherein the second catalyst precursor may be the same compound as the first catalyst precursor used for preparing the composition having the formula (I) or (II).

In certain embodiments, the present disclosure relates to a catalyst composition comprising the reaction product of at least one catalyst precursor, at least one co-catalyst, and the composition having the formula (I) or (II).

BRIEF DESCRIPTION OF THE DRAWINGS

FIG. 2 provides the $^{13}$C NMR spectra of the composition of Working Example 1.

DETAILED DESCRIPTION

Figure 1:
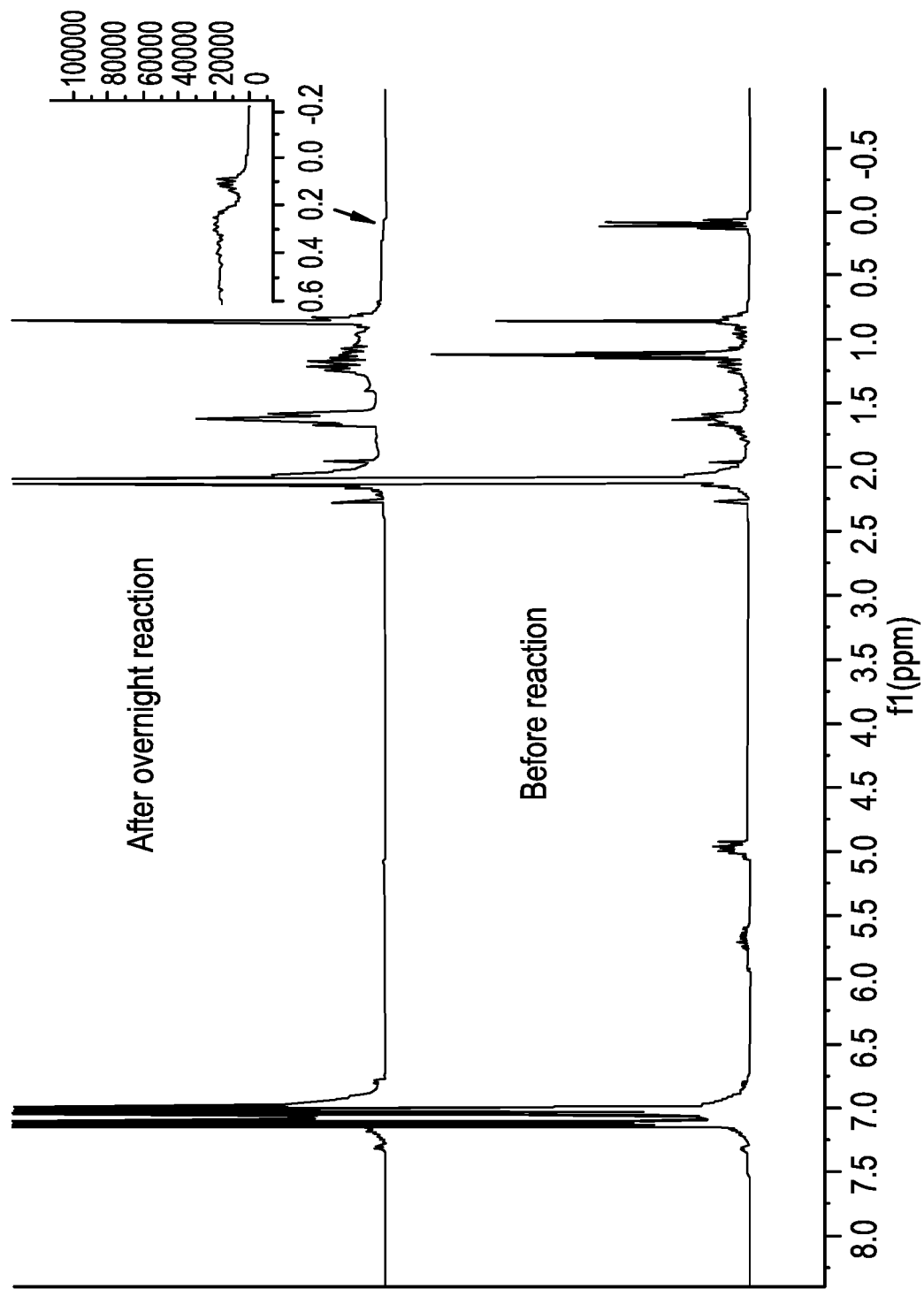
FIG. 1 provides the $^1$H NMR spectra of the composition of Working Example 1.

Embodiments of the present disclosure relate to a multi- or dual-headed composition (i.e., the composition having the formula (I) or (II)) as well as a process to prepare the same. In certain embodiments, the composition having the formula (I) or (II) may be a multi- or dual-headed chain shuttling agent. In further embodiments, the composition having the formula (I) or (II) may be a multi- or dual-headed chain transfer agent. In certain embodiments, the composition having the formula (I) or (II) may be capable of producing a telechelic functional polymer.

Definitions

All references to the Periodic Table of the Elements refer to the Periodic Table of the Elements published and copyrighted by CRC Press, Inc., 1990. Also, any references to a Group or Groups shall be to the Group or Groups reflected in this Periodic Table of the Elements using the IUPAC system for numbering groups. Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent U.S. version is so incorporated by reference in its entirety), especially with respect to the disclosure of synthetic techniques, product and processing designs, polymers, catalysts, definitions (to the extent not inconsistent with any definitions specifically provided in this disclosure), and general knowledge in the art.

Number ranges in this disclosure and as they relate to the composition having the formula (I) are approximate, and thus may include values outside of the range unless otherwise indicated. Number ranges include all values from and including the lower and the upper values, including fractional numbers or decimals.

The terms "chain shuttling agent" and "chain transfer agent" refer to those known to one of ordinary skill in the art. Specifically, the term "shuttling agent" or "chain shuttling agent" refers to a compound or mixture of compounds that is capable of causing polymeryl transfer between various active catalyst sites under conditions of polymerization. That is, transfer of a polymer fragment occurs both to and from an active catalyst site in a facile and reversible manner. In contrast to a shuttling agent or chain shuttling agent, an agent that acts merely as a "chain transfer agent," such as some main-group alkyl compounds, may exchange, for example, an alkyl group on the chain transfer agent with the growing polymer chain on the catalyst, which generally results in termination of the polymer chain growth. In this event, the main-group center may act as a repository for a dead polymer chain, rather than engaging in reversible transfer with a catalyst site in the manner in which a chain shuttling agent does. Desirably, the intermediate formed between the chain shuttling agent and the polymeryl chain is not sufficiently stable relative to exchange between this intermediate and any other growing polymeryl chain, such that chain termination is relatively rare.

"Multi- or dual-headed chain shuttling agents," such as those disclosed in U.S. Pat. No. 8,501,885 B2 and those known in the art, include species with metal-alkyl bonds that engage in chain transfer during a transition-metal catalyzed polymerization. Because these chain shuttling agents can be oligomeric, can consist of blends of species, or both, it is difficult to precisely describe these agents because, as they are used in solution, the CSA solution typically comprises a complex mixture of different species. Therefore, the useful CSAs disclosed here are typically described using average compositions, average numbers of multi-headed site valencies, average numbers of single-headed site valencies, and ratios of these numbers.

The terms "dual-headed" or "multi-headed" refer to a compound or molecule containing more than one chain shuttling moiety joined by a polyvalent linking group. By way of illustration only, one example of a dual-headed CSA is provided in the compounds of the general formulas $R^1[Zn-R^2-]_N Zn-R^1$ or $R^1-[AlR^1-R^2-]_N AlR^1{}_2$, in which $R^1$ is a monovalent hydrocarbyl group and $R^2$ is a divalent hydrocarbadiyl group. In practice, suitable chain shuttling moieties typically include metal centers derived from a metal selected from Groups 2-14 of the Periodic Table of the Elements and having one or more available valencies capable of reversibly binding a growing polymer chain prepared by a coordination polymerization catalyst. At the same time that the chain shuttling moiety binds to the growing polymer chain, the remnant of the polyvalent linking group remaining after loss of the chain shuttling moiety or moieties incorporates or otherwise bonds to one or more active catalyst sites, thereby forming a catalyst composition containing an active coordination polymerization site capable of polymer insertion at one terminus of what was originally the polyvalent linking group. Shuttling of the new polymer chain attached to the linking group back to the chain shuttling moiety effectively grows a fraction of polymer chains containing a linking group and attached to a main group metal CSA at both ends.

The term "derivative" used herein refers to the reaction product of a chemical group after the insertion reaction of said chemical group into metal alkyl bonds. For example, the "$R^2$" in $R^1-[Zn-R^2-]_N Zn-R^1$ can define the derivative (i.e., reaction product) of the linking group $CH_2=CH(CH_2)_6 CH=CH_2$ and $Zn(Et)_2$ to form $EtZn[(CH_2 C(Et)H(CH_2)_6 C(Et)HCH_2)Zn]_N Et$. In this example, $R^2$ is $-CH_2 C(Et)H(CH_2)_6 C(Et)HCH_2-$, a derivative of the insertion of linking group $CH_2=CH(CH_2)_6 CH=CH_2$ into Zn-Et bonds.

The term "linking group" is a chemical species whose derivative links multiple metal species together in a molecule by inserting into a metal alkyl bond of each metal. In the above example, $CH_2=CH(CH_2)_6 CH=CH$ is a "linking group" which joins N+1 zinc species to form the species $EtZn[(CH_2 C(Et)H(CH_2)_6 C(Et)HCH_2)Zn]_N Et$.

As a further non-limiting example of the terms "derivative" and "linking group" used herein, the "Y" in $R-[Zn-Y-]_n Zn-R$ can define the derivative (i.e., reaction product) of the linking group 1,2,4-trivinylcyclohexane (TVCH) to form the exemplary, non-limiting structure shown below. In this example, Y is the structure sandwiched between zinc atoms; said structure is a derivative of the insertion of linking group TVCH into Zn-R bonds.

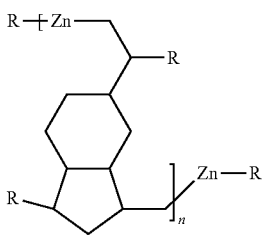

The term "precursor" or "catalyst precursor" used herein refers to a transition metal species that, once combined with an activator co-catalyst, is capable of polymerization of unsaturated monomers. For example, $Cp_2Zr(CH_3)_2$ is a catalyst precursor, which, when combined with an activating cocatalyst, becomes the active catalyst species "$Cp_2Zr(CH_3)^+$" which is capable of polymerization of unsaturated monomers.

"Catalyst precursors" include those known in the art and those disclosed in WO 2005/090426, WO 2005/090427, WO 2007/035485, WO 2009/012215, WO 2014/105411, U.S. Patent Publication Nos. 2006/0199930, 2007/0167578, 2008/0311812, and U.S. Pat. Nos. 7,355,089 B2, 8,058,373 B2, and 8,785,554 B2, all of which are incorporated herein by reference in their entirety. The terms "transition metal catalysts," "transition metal catalyst precursors," "catalysts," "catalyst precursors," "polymerization catalysts or catalyst precursors," "procatalysts," "metal complexes," "complexes," "metal-ligand complexes," and like terms are to be interchangeable in the present disclosure.

"Organometallic compound" refers to any compound that contains a metal-carbon bond, R-M, and includes those known in the art as it relates to the present disclosure.

"Co-catalyst" refers to those known in the art, e.g., those disclosed in WO 2005/090427 and U.S. Pat. No. 8,501,885 B2, that can activate the catalyst precursor to form an active catalyst composition. "Activator" and like terms are used interchangeably with "co-catalyst."

The term "catalyst system," "active catalyst," "activated catalyst," "active catalyst composition," "olefin polymerization catalyst," and like terms are interchangeable and refer to a catalyst precursor/co-catalyst pair. Such terms can also include more than one catalyst precursor and/or more than one activator and optionally a co-activator. Likewise, these terms can also include more than one activated catalyst and one or more activator or other charge-balancing moiety, and optionally a co-activator.

"Solvent" refers to those known in the art and those known as appropriate by one of ordinary skill in the art for the present disclosures. Suitable solvents include aromatic hydrocarbons, such as toluene, and aliphatic hydrocarbons, such as Isopar™ and heptane.

"Polymer" refers to a compound prepared by polymerizing monomers, whether of the same or a different type. The generic term polymer thus embraces the term homopolymer, usually employed to refer to polymers prepared from only one type of monomer, and the term interpolymer as defined below. It also embraces all forms of interpolymers, e.g., random, block, homogeneous, heterogeneous, etc.

"Interpolymer" and "copolymer" refer to a polymer prepared by the polymerization of at least two different types of monomers. These generic terms include both classical copolymers, i.e., polymers prepared from two different types of monomers, and polymers prepared from more than two different types of monomers, e.g., terpolymers, tetrapolymers, etc.

The term "block copolymer" or "segmented copolymer" refers to a polymer comprising two or more chemically distinct regions or segments (referred to as "blocks") joined in a linear manner, that is, a polymer comprising chemically differentiated units which are joined (covalently bonded) end-to-end with respect to polymerized functionality, rather than in pendent or grafted fashion. The blocks differ in the amount or type of comonomer incorporated therein, the density, the amount of crystallinity, the type of crystallinity (e.g., polyethylene versus polypropylene), the crystallite size attributable to a polymer of such composition, the type or degree of tacticity (isotactic or syndiotactic), regio-regularity or regio-irregularity, the amount of branching, including long chain branching or hyper-branching, the homogeneity, and/or any other chemical or physical property. The block copolymers are characterized by unique distributions of both polymer polydispersity (PDI or Mw/Mn) and block length distribution, e.g., based on the effect of the use of a shuttling agent(s) in combination with catalysts.

Compositions Having the Formula (I) or (II)

All schemes and discussions below are by way of example only and are not meant to be limiting in any way. In the event the name of a compound herein does not conform to the structural representation thereof, the structural representation shall control.

Embodiments of the present disclosure relate to a composition having the formula (I) or (II) or aggregates thereof, Lewis base-containing derivatives thereof, or any combination thereof:

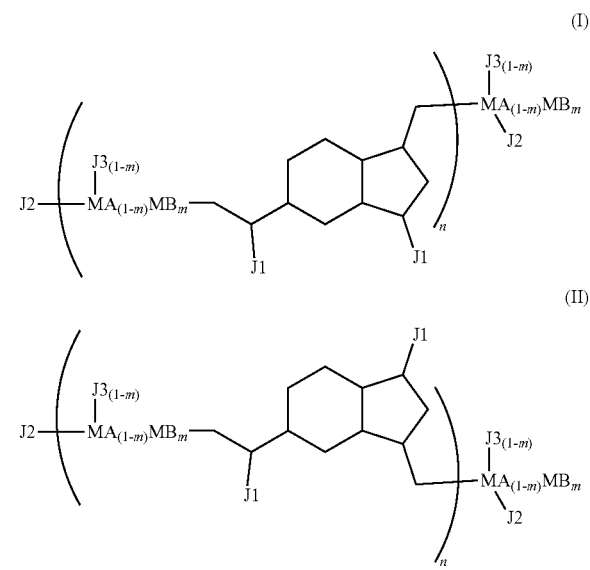

wherein:
each MA is Al, B, or Ga;
each MB is Zn or Mg;
m is a number from 0 to 1;
n is a number from 1 to 100; and
each J1, J2, and J3 is hydrogen or a hydrocarbyl group, and
wherein J1, J2, and J3 may be the same or different, or mixtures thereof.

As one of ordinary skill in the art would understand, should m be the number 1, J3 and MA would be excluded from (and MB would be included in) the composition having the formula (I) or (II). Likewise, should m be the number 0, MB would be excluded from (and J3 and MA would be included in) the composition having the formula (I) or (II).

With reference to J1, J2, and J3, examples of the hydrocarbyl group include $C_{1-20}$ alkyl groups (branched or unbranched), aryl groups, and aryl alkyl groups. Specific examples of the hydrocarbyl group include but are not limited to methyl, ethyl, n-propyl, n-butyl, isobutyl, n-hexyl, isohexyl, n-octyl, isooctyl, or isomers thereof. In certain embodiments, the hydrocarbyl group may be a substituted hydrocarbyl group with at least one substituent containing a heteroatom. Heteroatom as used herein includes all atoms with the exception of hydrogen and carbon.

The present compositions having the formula (I) or (II) may be used a chain shuttling agent or a chain transfer agent in polymerization reactions of olefin monomers. The present compositions may also be used to produce telechelic functional polymers (i.e., polymers with both terminal ends being functionalized).

The present disclosure further relates to the process for preparing the composition having the formula (I) or (II). In certain embodiments, the process for preparing the composition having the formula (I) or (II) comprises: (a) combining TVCH, an organometallic compound, a co-catalyst, a solvent, and a catalyst precursor, and (b) obtaining a final solution comprising the composition having the formula (I) or (II). In further embodiments, the process for preparing the composition having the formula (I) or (II) comprises: (a) combining TVCH, an organometallic compound, a co-catalyst, and a solvent to form a first solution; and (b) combining a catalyst precursor with the first solution to form a final solution comprising the composition having the formula (I) or (II).

In certain embodiments, the composition having the formula (I) or (II) prepared by the process of the present disclosure is formed via the plausible, non-limiting mechanism illustrated below in Scheme 1. With reference to exemplary, non-limiting Scheme 1, the vinyl double bond on the top and one of the vinyl groups on the bottom of the TVCH ring coordinate with the catalyst precursor and insert into the metal-carbon bond to form (1). The remaining neighboring vinyl inserts to form (2), a 5-member ring, which then transfers to zinc to form a dual-headed zinc species (3). The recovered catalyst precursor goes back to the catalyst cycle to react with another TVCH molecule. The dual headed zinc species (3) undergoes further chain transfer with (2) using the remaining terminal ZnR2, resulting in "polymeric" dual headed zinc species. This catalyst process continues until TVCH is exhausted. The length of the dual headed zinc chain is primarily determined by the metal/TVCH ratio. The closer the ratio to unity, the greater is the n value.

Scheme 1.

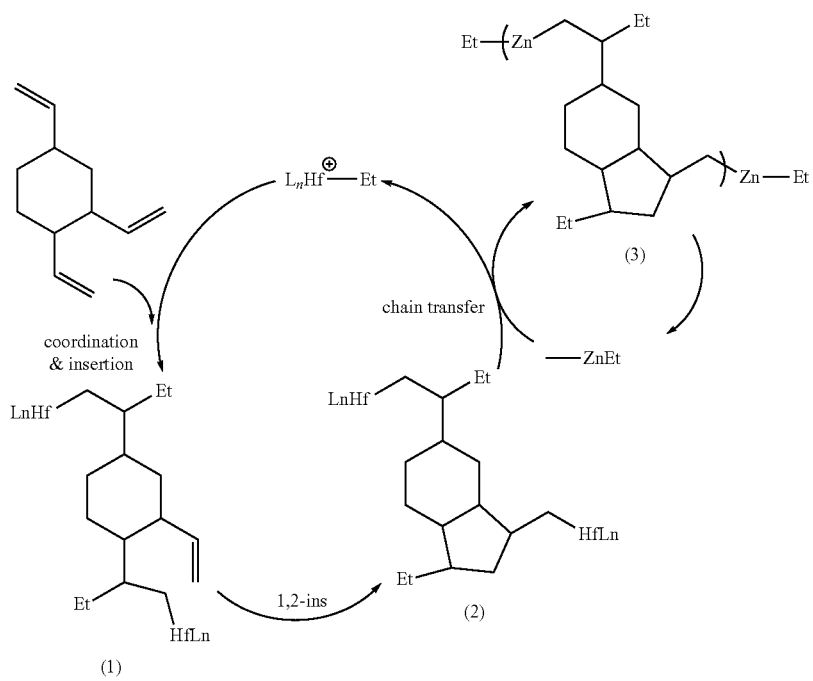

In certain embodiments, the process for preparing the composition having the formula (I) or (II) is a one-pot process without any isolation, purification, or separation requirements. In further embodiments, the process for preparing the composition having the formula (I) or (II) is a one-pot process; the catalyst precursor (in combination with the co-catalyst) remains as an active catalyst in the final solution, can further function as an active catalyst for subsequent olefin polymerization, and need not be removed prior to subsequent olefin polymerization. In certain embodiments, the catalyst precursor has no detrimental effect on subsequent olefin polymerization and is a good higher alpha-olefin incorporating (i.e., good comonomer incorporating) catalyst.

In certain embodiments, the composition having the formula (I) or (II) remains active in the final solution and can further function as a chain shuttling agent or chain transfer agent during olefin polymerization. Thus, in certain embodiments, the process of the present disclosure is a one-pot process, and the final solution of the process (containing the active catalyst and the composition having the formula (I) or (II)) can be directly used in olefin polymerization reactions without any isolation, purification, or separation requirements and without the requirement of having a removable supported catalyst.

Accordingly, in certain embodiments, the present disclosure relates to a polymerization process for preparing a polymer composition, the process comprising: contacting at least one addition polymerizable monomer (i.e., olefin monomer) with a catalyst composition under polymerization conditions; wherein the catalyst composition comprises the contact product (i.e., reaction product) of at least one catalyst precursor, at least one co-catalyst, and the composition having the formula (I) or (II). In further embodiments, the present disclosure relates to a polymerization process for preparing a polymer composition, the process comprising: contacting at least one addition polymerizable monomer (i.e., olefin monomer) with a catalyst composition under polymerization conditions; wherein the catalyst composition comprises the contact product (i.e., reaction product) of at least one catalyst precursor, at least one co-catalyst, and the composition having the formula (I) or (II), and wherein the catalyst precursor for the polymerization process is also the catalyst precursor used for preparing the composition having the formula (I) or (II). In other words, the catalyst precursor used to form the composition having the formula (I) or (II) is the same compound as the catalyst precursor used for olefin polymerization reactions.

While the catalyst remaining in the final solution can be directly used for polymerization, in certain embodiments, the catalyst in the final solution may optionally be removed from the final solution prior to polymerization by means known to those of ordinary skill in the art, such as passing the final solution through a plug of silica, alumina, or other bed media that will remove the active catalyst without reaction with or removal of more than a small percentage of the composition having the formula (I) or (II). Preferably, the removal process uses dehydrated amorphous silica.

As noted herein, multi- or dual-headed compositions (e.g., multi- or dual-headed CSAs) are of great interest since they can enable production of telechelic functional polymers. Specifically, with reference to the composition having the formula (I) or (II), the derivative of the linking group, TVCH, sandwiched between the two $MA_{(1-m)}MB_m$ groups can grow into a polymer chain with both terminal ends of the chain bonded to the $MA_{(1-m)}MB_m$ groups via terminal polymeryl-metal bonds. Subsequently, the terminal polymeryl-metal bonds may be transformed to desired functional groups via functionalization chemistry, thereby resulting in a desired di-functional polymer chain.

Organometallic Compound

In certain embodiments of the process of the present disclosure, the organometallic compound is a metal alkyl. In certain embodiments of the process of the present disclosure, the organometallic compound is a metal alkyl containing a divalent metal (e.g., Zn or Mg), a trivalent metal (e.g., Al, B, or Ga), or a mixture of divalent metal and trivalent metal. In certain embodiments of the process of the present disclosure, the organometallic compound is a divalent metal alkyl, such as dialkylzinc. In certain embodiments of the process of the present disclosure, the organometallic compound is a trivalent metal alkyl, such as trialkylaluminum. In certain embodiments of the process of the present disclosure, the organometallic compound is a mixture of divalent metal alkyl (e.g., dialkylzinc) and trivalent metal alkyl (e.g., trialkylaluminum).

Exemplary divalent metals suitable for the organometallic compound of the present disclosure include but are not limited to dimethyl zinc, diethyl zinc, dipropyl zinc, dibutyl zinc, diisobutyl zinc, dihexyl zinc, diisohexyl zinc, dioctyl zinc, and diisooctyl zinc. Exemplary divalent metals suitable for the organometallic compound of the present disclosure further include but are not limited to organomagnesium compounds, such as dimethyl magnesium, diethyl magnesium, dipropyl magnesium, dibutyl magnesium, diisobutyl magnesium, dihexyl magnesium, diisohexyl magnesium, dioctyl magnesium, and diisooctyl magnesium.

Exemplary trivalent metals suitable for the organometallic compound of the present disclosure include but are not limited to trimethyl aluminum, triethyl aluminum, tripropyl aluminum, tributyl aluminum, triisobutyl aluminum, trihexyl aluminum, triisohexyl aluminum, trioctyl aluminum, triisooctyl aluminum, tripentyl aluminum, tridecyl aluminum, tribranched alkyl aluminums, tricycloalkyl aluminums, triphenyl aluminum, tritolyl aluminum, dialkyl and aluminum hydrides. Further trivalent metals include but are not limited to organogallium compounds, such as trimethyl gallium, triethyl gallium, tripropyl gallium, tributyl gallium, triisobutyl gallium, trihexyl gallium, triisohexyl gallium, trioctyl gallium, and triisooctyl gallium.

In certain embodiments, J1, J2, and J3, as they relate to the composition having the formula (I) or (II), correspond to the alkyl group of the organometallic compound of the process of the present disclosure.

In certain embodiments of the process of the present disclosure, the organometallic compound, as it relates to "m" of the composition having the formula (I) or (II), is a metal alkyl containing a mixture of trivalent metal and divalent metal at a trivalent metal/divalent metal ratio from 99:1 to 1:99 (e.g., from 95:5 to 50:50, from 90:10 to 80:20, from 90:10 to 70:30, etc.). In certain embodiments of the process of the present disclosure, the organometallic compound is a metal alkyl containing a mixture of aluminum and zinc metals at an aluminum/zinc ratio from 99:1 to 1:99 (e.g., from 95:5 to 50:50, from 90:10 to 80:20, from 90:10 to 70:30, etc.).

In certain embodiments of the present disclosure, methods are considered to control the formation of insoluble gel that can easily form due to trivalent metals. In certain embodiments of the process of the present disclosure, the formation of the insoluble gel with trivalent metals is prevented by controlling the ratio ("the metal/TVCH ratio") of metal to linking group (i.e., TVCH). The higher the metal/TVCH ratio, the smaller the size of the oligomer and, thus, the lower the chance is for the formation of insoluble gel. In further embodiments, the structure and size of the composition of having the formula (I) or (II) may be tailored as desired via selection of the organometallic compound and the metal/TVCH ratio. Indeed, the length (n) of the composition having the formula (I) or (II) may be controlled by the metal/TVCH ratio, where metal/TVCH=(n+1)/n. Thus, for example, the metal/TVCH ratio is 2 for n=1, the metal/TVCH ratio is 1.5 for n=2, the metal/TVCH ratio is 1.33333 for n=3, etc. At very large "n" values, the metal/TVCH ratio approaches 1.

In certain embodiments, the metal/TVCH ratio is from 2:1 to 1:1 (where the length (n) of the composition having the formula (I) or (II) is a number from 1 to infinity). In further embodiments, the metal/TVCH ratio is from 3:2 to 11:10 (where the length (n) of the composition having the formula (I) or (II) is a number from 2 to 10).

Catalyst or Catalyst Precursor

Suitable catalyst precursors for use herein include any compound or combination of compounds that is adapted for preparing polymers of the desired composition or type and capable of reversible chain transfer with a chain shuttling agent. Both heterogeneous and homogeneous catalysts may be employed. Examples of heterogeneous catalysts include the well known Ziegler-Natta compositions, especially Group 4 metal halides supported on Group 2 metal halides or mixed halides and alkoxides and the well known chromium or vanadium based catalysts. Preferably, the catalysts for use herein are homogeneous catalysts comprising a relatively pure organometallic compound or metal complex, especially compounds or complexes based on metals selected from Groups 3-10 or the Lanthanide series of the Periodic Table of the Elements.

Metal complexes for use herein may be selected from Groups 3 to 15 of the Periodic Table of the Elements containing one or more delocalized, π-bonded ligands or polyvalent Lewis base ligands. Examples include metallocene, half-metallocene, constrained geometry, and polyvalent pyridylamine, or other polychelating base complexes. The complexes are generically depicted by the formula: $MK_kX_xZ_z$, or a dimer thereof, wherein M is a metal selected from Groups 3-15, preferably 3-10, more preferably 4-10, and most preferably Group 4 of the Periodic Table of the Elements;

K independently at each occurrence is a group containing delocalized π-electrons or one or more electron pairs through which K is bound to M, said K group containing up to 50 atoms not counting hydrogen atoms, optionally two or more K groups may be joined together forming a bridged structure, and further optionally one or more K groups may be bound to Z, to X or to both Z and X;

X independently at each occurrence is a monovalent, anionic moiety having up to 40 non-hydrogen atoms, optionally one or more X groups may be bonded together thereby forming a divalent or polyvalent anionic group, and, further optionally, one or more X groups and one or more Z groups may be bonded together thereby forming a moiety that is both covalently bound to M and coordinated thereto; or two X groups together form a divalent anionic ligand group of up to 40 non-hydrogen atoms or together are a conjugated diene having from 4 to 30 non-hydrogen atoms bound by means of delocalized i-electrons to M, whereupon M is in the +2 formal oxidation state, and Z independently at each occurrence is a neutral, Lewis base donor ligand of up to 50 non-hydrogen atoms containing at least one unshared electron pair through which Z is coordinated to M;

k is an integer from 0 to 3; x is an integer from 1 to 4; z is a number from 0 to 3; and the sum, k+x, is equal to the formal oxidation state of M.

Suitable metal complexes include those containing from 1 to 3 π-bonded anionic or neutral ligand groups, which may be cyclic or non-cyclic delocalized π-bonded anionic ligand groups. Exemplary of such π-bonded groups are conjugated or nonconjugated, cyclic or non-cyclic diene and dienyl groups, allyl groups, boratabenzene groups, phosphole, and arene groups. By the term "π-bonded" is meant that the ligand group is bonded to the transition metal by a sharing of electrons from a partially delocalized π-bond.

Each atom in the delocalized π-bonded group may independently be substituted with a radical selected from the group consisting of hydrogen, halogen, hydrocarbyl, halohydrocarbyl, hydrocarbyl-substituted heteroatoms wherein the heteroatom is selected from Group 14-16 of the Periodic Table of the Elements, and such hydrocarbyl-substituted heteroatom radicals further substituted with a Group 15 or 16 hetero atom containing moiety. In addition two or more such radicals may together form a fused ring system, including partially or fully hydrogenated fused ring systems, or they may form a metallocycle with the metal. Included within the term "hydrocarbyl" are $C_{1-20}$ straight, branched and cyclic alkyl radicals, $C_{6-20}$ aromatic radicals, $C_{7-20}$ alkyl-substituted aromatic radicals, and $C_{7-20}$ aryl-substituted alkyl radicals. Suitable hydrocarbyl-substituted heteroatom radicals include mono-, di- and tri-substituted radicals of boron, silicon, germanium, nitrogen, phosphorus or oxygen wherein each of the hydrocarbyl groups contains from 1 to 20 carbon atoms. Examples include N,N-dimethylamino, pyrrolidinyl, trimethylsilyl, triethylsilyl, t-butyldimethylsilyl, methyldi(t-butyl)silyl, triphenylgermyl, and trimethylgermyl groups. Examples of Group 15 or 16 hetero atom containing moieties include amino, phosphino, alkoxy, or alkylthio moieties or divalent derivatives thereof, for example, amide, phosphide, alkyleneoxy or alkylenethio groups bonded to the transition metal or Lanthanide metal, and bonded to the hydrocarbyl group, π-bonded group, or hydrocarbyl-substituted heteroatom.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, phosphole, and boratabenzyl groups, as well as inertly substituted derivatives thereof, especially $C_{1-10}$ hydrocarbyl-substituted or tris($C_{1-10}$ hydrocarbyl)silyl-substituted derivatives thereof. Preferred anionic delocalized π-bonded groups are cyclopentadienyl, pentamethylcyclopentadienyl, tetramethylcyclopentadienyl, tetramethylsilylcyclopentadienyl, indenyl, 2,3-dimethylindenyl, fluorenyl, 2-methylindenyl, 2-methyl-4-phenylindenyl, tetrahydrofluorenyl, octahydrofluorenyl, 1-indacenyl, 3-pyrrolidinoinden-1-yl, 3,4-(cyclopenta(l)phenanthren-1-yl, and tetrahydroindenyl.

The boratabenzenyl ligands are anionic ligands which are boron containing analogues to benzene. They are previously known in the art having been described by G. Herberich, et al., in *Organometallics*, 14,1, 471-480 (1995). Preferred boratabenzenyl ligands correspond to the formula:

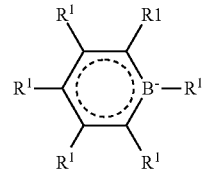

wherein $R^1$ is an inert substituent, preferably selected from the group consisting of hydrogen, hydrocarbyl, silyl, halo or germyl, said $R^1$ having up to 20 atoms not counting hydrogen, and optionally two adjacent $R^1$ groups may be joined together. In complexes involving divalent derivatives of such delocalized π-bonded groups one atom thereof is bonded by means of a covalent bond or a covalently bonded divalent group to another atom of the complex thereby forming a bridged system.

Phospholes are anionic ligands that are phosphorus containing analogues to a cyclopentadienyl group. They are previously known in the art having been described by WO 98/50392, and elsewhere. Preferred phosphole ligands correspond to the formula:

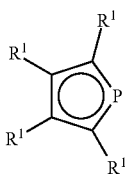

wherein $R^1$ is as previously defined.

Suitable transition metal complexes for use herein correspond to the formula: $MK_kX_xZ_z$, or a dimer thereof, wherein:

M is a Group 4 metal;

K is a group containing delocalized π-electrons through which K is bound to M, said K group containing up to 50 atoms not counting hydrogen atoms, optionally two K groups may be joined together forming a bridged structure, and further optionally one K may be bound to X or Z;

X at each occurrence is a monovalent, anionic moiety having up to 40 non-hydrogen atoms, optionally one or more X and one or more K groups are bonded together to form a metallocycle, and further optionally one or more X and one or more Z groups are bonded together thereby forming a moiety that is both covalently bound to M and coordinated thereto;

Z independently at each occurrence is a neutral, Lewis base donor ligand of up to 50 non-hydrogen atoms containing at least one unshared electron pair through which Z is coordinated to M;

k is an integer from 0 to 3; x is an integer from 1 to 4; z is a number from 0 to 3; and the sum, k+x, is equal to the formal oxidation state of M.

Suitable complexes include those containing either one or two K groups. The latter complexes include those containing a bridging group linking the two K groups. Suitable bridging groups are those corresponding to the formula $(ER'_2)_e$ wherein E is silicon, germanium, tin, or carbon, R' independently at each occurrence is hydrogen or a group selected from silyl, hydrocarbyl, hydrocarbyloxy and combinations thereof, said R' having up to 30 carbon or silicon atoms, and e is 1 to 8. Illustratively, R' independently at each occurrence is methyl, ethyl, propyl, benzyl, tert-butyl, phenyl, methoxy, ethoxy or phenoxy.

Examples of the complexes containing two K groups are compounds corresponding to the formula:

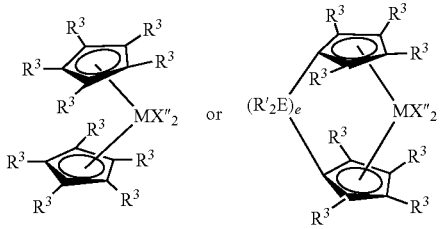

wherein:

M is titanium, zirconium or hafnium, preferably zirconium or hafnium, in the +2 or +4 formal oxidation state; $R^3$ at each occurrence independently is selected from the group consisting of hydrogen, hydrocarbyl, silyl, germyl, cyano, halo and combinations thereof, said $R^3$ having up to 20 non-hydrogen atoms, or adjacent $R^3$ groups together form a divalent derivative (that is, a hydrocarbadiyl, siladiyl or germadiyl group) thereby forming a fused ring system, and X" independently at each occurrence is an anionic ligand group of up to 40 non-hydrogen atoms, or two X" groups together form a divalent anionic ligand group of up to 40 non-hydrogen atoms or together are a conjugated diene having from 4 to 30 non-hydrogen atoms bound by means of delocalized i-electrons to M, whereupon M is in the +2 formal oxidation state, and R', E and e are as previously defined.

Exemplary bridged ligands containing two π-bonded groups are: dimethylbis(cyclopentadienyl)silane, dimethylbis(tetramethylcyclopentadienyl)silane, dimethylbis(2-ethylcyclopentadien-1-yl)silane, dimethylbis(2-t-butylcyclopentadien-1-yl)silane, 2,2-bis(tetramethylcyclopentadienyl) propane, dimethylbis(inden-1-yl)silane, dimethylbis (tetrahydroinden-1-yl)silane, dimethylbis(fluoren-1-yl) silane, dimethylbis(tetrahydrofluoren-1-yl)silane, dimethylbis(2-methyl-4-phenylinden-1-yl)-silane, dimethylbis(2-methylinden-1-yl)silane, dimethyl(cyclopentadienyl)(fluoren-1-yl)silane, dimethyl(cyclopentadienyl)(octahydrofluoren-1-yl)silane, dimethyl(cyclopentadienyl) (tetrahydrofluoren-1-yl)silane, (1,1,2,2-tetramethyl)-1,2-bis (cyclopentadienyl)disilane, (1,2-bis(cyclopentadienyl) ethane, and dimethyl(cyclopentadienyl)-1-(fluoren-1-yl) methane.

Suitable X" groups are selected from hydride, hydrocarbyl, silyl, germyl, halohydrocarbyl, halosilyl, silylhydrocarbyl and aminohydrocarbyl groups, or two X" groups together form a divalent derivative of a conjugated diene or else together they form a neutral, π-bonded, conjugated diene. Exemplary X" groups are C1-20 hydrocarbyl groups.

Examples of metal complexes of the foregoing formula suitable for use in the present disclosure include:

bis(cyclopentadienyl)zirconiumdimethyl,
bis(cyclopentadienyl)zirconium dibenzyl,
bis(cyclopentadienyl)zirconium methyl benzyl,
bis(cyclopentadienyl)zirconium methyl phenyl,
bis(cyclopentadienyl)zirconiumdiphenyl,
bis(cyclopentadienyl)titanium-allyl,
bis(cyclopentadienyl)zirconiummethylmethoxide,
bis(cyclopentadienyl)zirconiummethylchloride,
bis(pentamethylcyclopentadienyl)zirconiumdimethyl,
bis(pentamethylcyclopentadienyl)titaniumdimethyl,
bis(indenyl)zirconiumdimethyl,
indenylfluorenylzirconiumdimethyl,
bis(indenyl)zirconiummethyl(2-(dimethylamino)benzyl),
bis(indenyl)zirconiummethyltrimethylsilyl,
bis(tetrahydroindenyl)zirconiummethyltrimethylsilyl,
bis(pentamethylcyclopentadienyl)zirconiummethylbenzyl,
bis(pentamethylcyclopentadienyl)zirconiumdibenzyl,
bis(pentamethylcyclopentadienyl)zirconiummethylmethoxide,
bis(pentamethylcyclopentadienyl)zirconiummethylchloride,
bis(methylethylcyclopentadienyl)zirconiumdimethyl,
bis(butylcyclopentadienyl)zirconiumdibenzyl,
bis(t-butylcyclopentadienyl)zirconiumdimethyl,
bis(ethyltetramethylcyclopentadienyl)zirconiumdimethyl,
bis(methylpropylcyclopentadienyl)zirconiumdibenzyl,
bis(trimethylsilylcyclopentadienyl)zirconiumdibenzyl,
dimethylsilylbis(cyclopentadienyl)zirconiumdichloride,
dimethylsilylbis(cyclopentadienyl)zirconiumdimethyl,
dimethylsilylbis(tetramethylcyclopentadienyl)titanium (III) allyl
dimethylsilylbis(t-butylcyclopentadienyl)zirconiumdichloride, dimethylsilylbis(n-butylcyclopentadienyl)zirconiumdichloride,
(dimethylsilylbis(tetramethylcyclopentadienyl)titanium (III) 2-(dimethylamino)benzyl,
(dimethylsilylbis(n-butylcyclopentadienyl)titanium(III) 2-(dimethylamino)benzyl, dimethylsilylbis(indenyl)zirconiumdichloride,
dimethylsilylbis(indenyl)zirconiumdimethyl,
dimethylsilylbis(2-methylindenyl)zirconiumdimethyl,
dimethylsilylbis(2-methyl-4-phenylindenyl)zirconiumdimethyl,
dimethylsilylbis(2-methylindenyl)zirconium-1,4-diphenyl-1,3-butadiene,
dimethylsilylbis(2-methyl-4-phenylindenyl)zirconium (II) 1,4-diphenyl-1,3-butadiene, dimethylsilylbis(4,5,6,7-tetrahydroinden-1-yl)zirconiumdichloride,
dimethylsilylbis(4,5,6,7-tetrahydroinden-1-yl)zirconiumdimethyl,
dimethylsilylbis(tetrahydroindenyl)zirconium(II) 1,4-diphenyl-1,3-butadiene,
dimethylsilylbis(tetramethylcyclopentadienyl)zirconium dimethyl,
dimethylsilylbis(fluorenyl)zirconiumdimethyl,
dimethylsilylbis(tetrahydrofluorenyl)zirconium bis(trimethylsilyl),
ethylenebis(indbnyl)zirconiumdichloride,
ethylenebis(indenyl)zirconiumdimethyl,
ethylenebis(4,5,6,7-tetrahydroindenyl)zirconiumdichloride,
ethylenebis(4,5,6,7-tetrahydroindenyl)zirconiumdimethyl,
(isopropylidene)(cyclopentadienyl)(fluorenyl)zirconiumdibenzyl, and
dimethylsilyl(tetramethylcyclopentadienyl)(fluorenyl)zirconium dimethyl.

A further class of metal complexes utilized in the present disclosure corresponds to the preceding formula: $MKZ_zX_x$, or a dimer thereof, wherein M, K, X, x and z are as previously defined, and Z is a substituent of up to 50 non-hydrogen atoms that together with K forms a metallocycle with M.

Suitable Z substituents include groups containing up to 30 non-hydrogen atoms comprising at least one atom that is oxygen, sulfur, boron or a member of Group 14 of the Periodic Table of the Elements directly attached to K, and a different atom, selected from the group consisting of nitrogen, phosphorus, oxygen or sulfur that is covalently bonded to M.

More specifically this class of Group 4 metal complexes used according to the present invention includes "constrained geometry catalysts" corresponding to the formula:

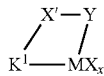

wherein: M is titanium or zirconium, preferably titanium in the +2, +3, or +4 formal oxidation state;
$K^1$ is a delocalized, π-bonded ligand group optionally substituted with from 1 to 5 $R^2$ groups,
$R^2$ at each occurrence independently is selected from the group consisting of hydrogen, hydrocarbyl, silyl, germyl, cyano, halo and combinations thereof, said $R^2$ having up to 20 non-hydrogen atoms, or adjacent $R^2$ groups together form a divalent derivative (that is, a hydrocarbadiyl, siladiyl or germadiyl group) thereby forming a fused ring system,
each X is a halo, hydrocarbyl, heterohydrocarbyl, hydrocarbyloxy or silyl group, said group having up to 20 non-hydrogen atoms, or two X groups together form a neutral C5-30 conjugated diene or a divalent derivative thereof;
x is 1 or 2;
Y is —O—, -S-, —NR'—, —PR'—;
and X' is $SiR'_2$, $CR'_2$, $SiR'_2SiR'_2$, $CR'_2CR'_2$, $CR'=CR'$, $CR'_2SiR'_2$, or $GeR'_2$, wherein
R' independently at each occurrence is hydrogen or a group selected from silyl, hydrocarbyl, hydrocarbyloxy and combinations thereof, said R' having up to 30 carbon or silicon atoms.

Specific examples of the foregoing constrained geometry metal complexes include compounds corresponding to the formula:

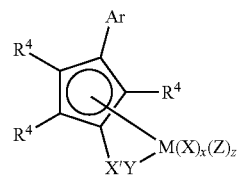

wherein,
Ar is an aryl group of from 6 to 30 atoms not counting hydrogen;
$R^4$ independently at each occurrence is hydrogen, Ar, or a group other than Ar selected from hydrocarbyl, trihydrocarbylsilyl, trihydrocarbylgermyl, halide, hydrocarbyloxy, trihydrocarbylsiloxy, bis(trihydrocarbylsilyl)amino, di(hydrocarbyl)amino, hydrocarbadiylamino, hydrocarbylimino, di(hydrocarbyl)phosphino, hydrocarbadiylphosphino, hydrocarbylsulfido, halo-substituted hydrocarbyl, hydrocarbyloxy-substituted hydrocarbyl, trihydrocarbylsilyl-substituted hydrocarbyl, trihydrocarbylsiloxy-substituted hydrocarbyl, bis(trihydrocarbylsilyl)amino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R group having up to 40 atoms not counting hydrogen atoms, and optionally two adjacent $R^4$ groups may be joined together forming a polycyclic fused ring group;
M is titanium;
X' is $SiR^6_2$, $CR^6_2$, $SiR^6_2$, $SiR^6_2$, $CR^6_2CR^6_2$, $CR^6=CR^6$, $CR^6_2SiR^6_2$, $BR^6$, $BR^EL"$, or $GeR^6_2$;
Y is —O—, —S—, —PRS—; —$NR^5_2$, or —$PR^5_2$;
$R^5$, independently at each occurrence is hydrocarbyl, trihydrocarbylsilyl, or trihydrocarbylsilylhydrocarbyl, said $R^5$ having up to 20 atoms other than hydrogen, and optionally two $R^5$ groups or $R^5$ together with Y or Z form a ring system;
$R^6$, independently at each occurrence, is hydrogen, or a member selected from hydrocarbyl, hydrocarbyloxy, silyl, halogenated alkyl, halogenated aryl, —$NR^5_2$, and combinations thereof, said $R^6$ having up to 20 non-hydrogen atoms, and optionally, two $R^6$ groups or $R^6$ together with Z forms a ring system;
Z is a neutral diene or a monodentate or polydentate Lewis base optionally bonded to $R^5$, $R^6$, or X;

X is hydrogen, a monovalent anionic ligand group having up to 60 atoms not counting hydrogen, or two X groups are joined together thereby forming a divalent ligand group;

x is 1 or 2; and z is 0, 1 or 2.

Suitable examples of the foregoing metal complexes are substituted at both the 3- and 4-positions of a cyclopentadienyl or indenyl group with an Ar group. Examples of the foregoing metal complexes include:

- (3-phenylcyclopentadien-1-yl)dimethyl(t-butylamido)silanetitanium dichloride,
- (3-phenylcyclopentadien-1-yl)dimethyl(t-butylamido)silanetitanium dimethyl,
- (3-phenylcyclopentadien-1-yl)dimethyl(t-butylamido)silanetitanium (II) 1,3-diphenyl-1,3-butadiene;
- (3-(pyrrol-1-yl)cyclopentadien-1-yl)dimethyl(t-butylamido)silanetitanium dichloride,
- (3-(pyrrol-1-yl)cyclopentadien-1-yl)dimethyl(t-butylamido)silanetitanium dimethyl,
- (3-(pyrrol-1-yl)cyclopentadien-1-yl))dimethyl(t-butylamido)silanetitanium (II) 1,4-diphenyl-1,3-butadiene;
- (3-(1-methylpyrrol-3-yl)cyclopentadien-1-yl)dimethyl(t-butylamido)silanetitanium dichloride,
- (3-(1-methylpyrrol-3-yl)cyclopentadien-1-yl)dimethyl(t-butylamido)silanetitanium dimethyl,
- (3-(1-methylpyrrol-3-yl)cyclopentadien-1-yl)dimethyl(t-butylamido)silanetitanium (II) 1,4-diphenyl-1,3-butadiene;
- (3,4-diphenylcyclopentadien-1-yl)dimethyl(t-butylamido)silanetitanium dichloride,
- (3,4-diphenylcyclopentadien-1-yl)dimethyl(t-butylamido)silanetitanium dimethyl,
- (3,4-diphenylcyclopentadien-1-yl)dimethyl(t-butylamido)silanetitanium (II) 1,3-pentadiene;
- (3-(3-N,N-dimethylamino)phenyl)cyclopentadien-1-yl)dimethyl(t-butylamido)silanetitanium dichloride,
- (3-(3-N,N-dimethylamino)phenylcyclopentadien-1-yl)dimethyl(t-butylamido)silanetitanium dimethyl,
- (3-(3-N,N-dimethylamino)phenylcyclopentadien-1-yl)dimethyl(t-butylamido)silanetitanium (II) 1,4-diphenyl-1,3-butadiene;
- (3-(4-methoxyphenyl)-4-methylcyclopentadien-1-yl)dimethyl(t-butylamido)silanetitanium dichloride,
- (3-(4-methoxyphenyl)-4-phenylcyclopentadien-1-yl)dimethyl(t-butylamido)silanetitanium dimethyl,
- (3-4-methoxyphenyl)-4-phenylcyclopentadien-1-yl)dimethyl(t-butylamido)silanetitanium (II) 1,4-diphenyl-1,3-butadiene;
- (3-phenyl-4-methoxycyclopentadien-1-yl)dimethyl(t-butylamido)silanetitanium dichloride,
- (3-phenyl-4-methoxycyclopentadien-1-yl)dimethyl(t-butylamido)silanetitanium dimethyl,
- (3-phenyl-4-methoxycyclopentadien-1-yl)dimethyl(t-butylamido)silanetitanium (II) 1,4-diphenyl-1,3-butadiene;
- (3-phenyl-4-(N,N-dimethylamino)cyclopentadien-1-yl)dimethyl(t-butylamido)silanetitanium dichloride,
- (3-phenyl-4-(N,N-dimethylamino)cyclopentadien-1-yl)dimethyl(t-butylamido)silanetitanium dimethyl,
- (3-phenyl-4-(N,N-dimethylamino)cyclopentadien-1-yl)dimethyl(t-butylamido)silanetitanium (II) 1,4-diphenyl-1,3-butadiene;
- 2-methyl-(3,4-di(4-methylphenyl)cyclopentadien-1-yl)dimethyl(t-butylamido)silanetitanium dichloride,
- 2-methyl-(3,4-di(4-methylphenyl)cyclopentadien-1-yl)dimethyl(t-butylamido)silanetitanium dimethyl,
- 2-methyl-(3,4-di(4-methylphenyl)cyclopentadien-1-yl)dimethyl(t-butylamido)silanetitanium (II) 1,4-diphenyl-1,3-butadiene;
- ((2,3-diphenyl)-4-(N,N-dimethylamino)cyclopentadien-1-yl)dimethyl(t-butylamido)silane titanium dichloride,
- ((2,3-diphenyl)-4-(N,N-dimethylamino)cyclopentadien-1-yl)dimethyl(t-butylamido)silane titanium dimethyl,
- ((2,3-diphenyl)-4-(N,N-dimethylamino)cyclopentadien-1-yl)dimethyl(t-butylamido)silanetitanium (II) 1,4-diphenyl-1,3-butadiene;
- (2,3,4-triphenyl-5-methylcyclopentadien-1-yl)dimethyl(t-butylamido)silanetitanium dichloride,
- (2,3,4-triphenyl-5-methylcyclopentadien-1-yl)dimethyl(t-butylamido)silanetitanium dimethyl,
- (2,3,4-triphenyl-5-methylcyclopentadien-1-yl)dimethyl(t-butylamido)silanetitanium (II) 1,4-diphenyl-1,3-butadiene;
- (3-phenyl-4-methoxycyclopentadien-1-yl)dimethyl(t-butylamido)silanetitanium dichloride,
- (3-phenyl-4-methoxycyclopentadien-1-yl)dimethyl(t-butylamido)silanetitanium dimethyl,
- (3-phenyl-4-methoxycyclopentadien-1-yl)dimethyl(t-butylamido)silanetitanium (II) 1,4-diphenyl-1,3-butadiene;
- (2,3-diphenyl-4-(n-butyl)cyclopentadien-1-yl)dimethyl(t-butylamido)silanetitanium dichloride,
- (2,3-diphenyl-4-(n-butyl)cyclopentadien-1-yl)dimethyl(t-butylamido)silanetitanium dimethyl,
- (2,3-diphenyl-4-(n-butyl)cyclopentadien-1-yl)dimethyl(t-butylamido)silanetitanium (II) 1,4-diphenyl-1,3-butadiene;
- (2,3,4,5-tetraphenylcyclopentadien-1-yl)dimethyl(t-butylamido)silanetitanium dichloride,
- (2,3,4,5-tetraphenylcyclopentadien-1-yl)dimethyl(t-butylamido)silanetitanium dimethyl, and (2,3,4,5-tetraphenylcyclopentadien-1-yl)dimethyl(t-butylamido)silanetitanium (II) 1,4-diphenyl-1,3-butadiene.

Additional examples of suitable metal complexes herein are polycyclic complexes corresponding to the formula:

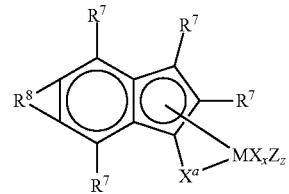

where M is titanium in the +2, +3 or +4 formal oxidation state;

$R^7$ independently at each occurrence is hydride, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl) phosphino-substituted hydrocarbyl, hydrocarbylenephosphino-substituted hydrocarbyl, or hydrocarbylsulfido-substituted hydrocarbyl, said $R^7$ group having up to 40 atoms not counting hydrogen, and optionally two or more of the foregoing groups may together form a divalent derivative;

R⁸ is a divalent hydrocarbylene- or substituted hydrocarbylene group forming a fused system with the remainder of the metal complex, said R⁸ containing from 1 to 30 atoms not counting hydrogen;

X$^a$ is a divalent moiety, or a moiety comprising one 6-bond and a neutral two electron pair able to form a coordinate-covalent bond to M, said X$^a$ comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic, delocalized, π-bound ligand groups and optionally two X groups together form a divalent ligand group;

Z independently at each occurrence is a neutral ligating compound having up to 20 atoms;

x is 0, 1 or 2; and z is zero or 1.

Suitable examples of such complexes are 3-phenyl-substituted s-indecenyl complexes corresponding to the formula:

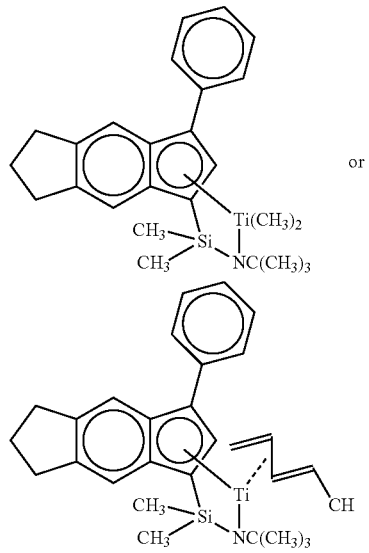

2,3-dimethyl-substituted s-indecenyl complexes corresponding to the formulas:

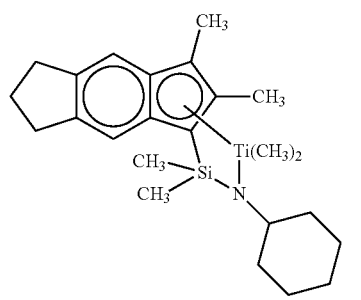

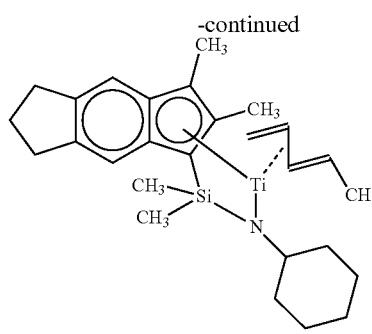

or 2-methyl-substituted s-indecenyl complexes corresponding to the formula:

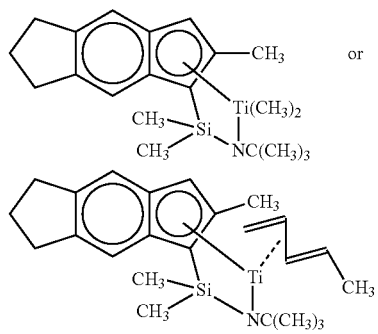

Additional examples of metal complexes that are usefully employed as catalysts according to the present invention include those of the formula:

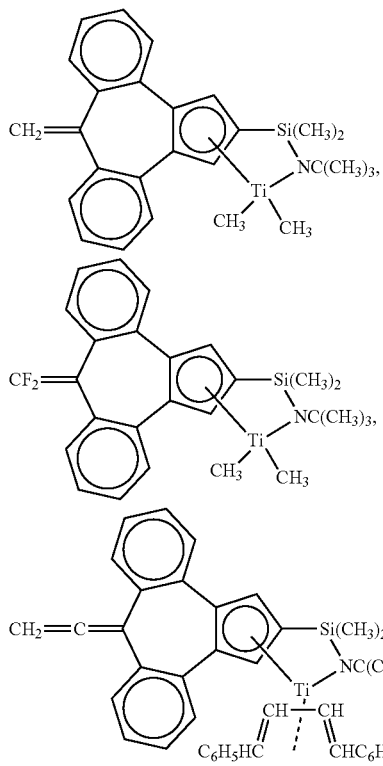

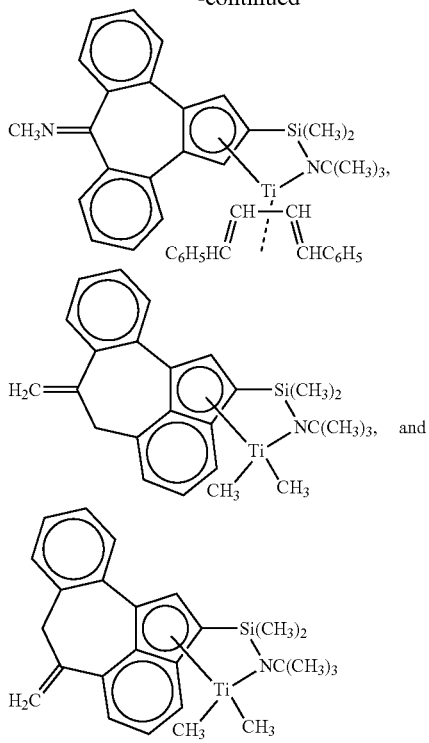

Specific metal complexes include:
(8-methylene-1,8-dihydrodibenzo[e,h]azulen-1-yl)-N-(1,1-dimethylethyl)dimethylsilanamide titanium (II) 1,4-diphenyl-1,3-butadiene,
(8-methylene-1,8-dihydrodibenzo[e,h]azulen-1-yl)-N-(1,1-dimethylethyl)dimethylsilanamide titanium (II) 1,3-pentadiene,
(8-methylene-1,8-dihydrodibenzo[e,h]azulen-1-yl)-N-(1,1-dimethylethyl)dimethylsilanamide titanium (III) 2-(N,N-dimethylamino)benzyl,
(8-methylene-1,8-dihydrodibenzo[e,h]azulen-1-yl)-N-(1,1-dimethylethyl)dimethylsilanamide titanium (IV) dichloride,
(8-methylene-1,8-dihydrodibenzo[e,h]azulen-1-yl)-N-(1,1-dimethylethyl)dimethylsilanamide titanium (IV) dimethyl,
(8-methylene-1,8-dihydrodibenzo[e,h]azulen-1-yl)-N-(1,1-dimethylethyl)dimethylsilanamide titanium (IV) dibenzyl,
(8-difluoromethylene-1,8-dihydrodibenzo[e,h]azulen-1-yl)-N-(1,1-dimethylethyl)dimethylsilanamide titanium (II) 1,4-diphenyl-1,3-butadiene,
(8-difluoromethylene-1,8-dihydrodibenzo[e,h]azulen-1-yl)-N-(1,1-dimethylethyl)dimethylsilanamide titanium (II) 1,3-pentadiene,
(8-difluoromethylene-1,8-dihydrodibenzo[e,h]azulen-1-yl)-N-(1,1-dimethylethyl)dimethylsilanamide titanium (III) 2-(N,N-dimethylamino)benzyl,
(8-difluoromethylene-1,8-dihydrodibenzo[e,h]azulen-1-yl)-N-(1,1-dimethylethyl)dimethylsilanamide titanium (IV) dichloride,
(8-difluoromethylene-1,8-dihydrodibenzo[e,h]azulen-1-yl)-N-(1,1-dimethylethyl)dimethylsilanamide titanium (IV) dimethyl,
(8-difluoromethylene-1,8-dihydrodibenzo[e,h]azulen-1-yl)-N-(1,1-dimethylethyl)dimethylsilanamide titanium (IV) dibenzyl,
(8-methylene-1,8-dihydrodibenzo[e,h]azulen-2-yl)-N-(1,1-dimethylethyl)dimethylsilanamide titanium (II) 1,4-diphenyl-1,3-butadiene,
(8-methylene-1,8-dihydrodibenzo[e,h]azulen-2-yl)-N-(1,1-dimethylethyl)dimethylsilanamide titanium (II) 1,3-pentadiene,
(8-methylene-1,8-dihydrodibenzo[e,h]azulen-2-yl)-N-(1,1-dimethylethyl)dimethylsilanamide titanium (III) 2-(N,N-dimethylamino)benzyl,
(8-methylene-1,8-dihydrodibenzo[e,h]azulen-2-yl)-N-(1,1-dimethylethyl)dimethylsilanamide titanium (IV) dichloride,
(8-methylene-1,8-dihydrodibenzo[e,h]azulen-2-yl)-N-(1,1-dimethylethyl)dimethylsilanamide titanium (IV) dimethyl,
(8-methylene-1,8-dihydrodibenzo[e,h]azulen-2-yl)-N-(1,1-dimethylethyl)dimethylsilanamide titanium (IV) dibenzyl,
(8-difluoromethylene-1,8-dihydrodibenzo[e,h]azulen-2-yl)-N-(1,1-dimethylethyl)dimethylsilanamide titanium (II) 1,4-diphenyl-1,3-butadiene,
(8-difluoromethylene-1,8-dihydrodibenzo[e,h]azulen-2-yl)-N-(1,1-dimethylethyl)dimethylsilanamide titanium (II) 1,3-pentadiene,
(8-difluoromethylene-1,8-dihydrodibenzo[e,h]azulen-2-yl)-N-(1,1-dimethylethyl)dimethylsilanamide titanium (III) 2-(N,N-dimethylamino)benzyl,
(8-difluoromethylene-1,8-dihydrodibenzo[e,h]azulen-2-yl)-N-(1,1-dimethylethyl)dimethylsilanamide titanium (IV) dichloride,
(8-difluoromethylene-1,8-dihydrodibenzo[e,h]azulen-2-yl)-N-(1,1-dimethylethyl)dimethylsilanamide titanium (IV) dimethyl,
(8-difluoromethylene-1,8-dihydrodibenzo[e,h]azulen-2-yl)-N-(1,1-dimethylethyl)dimethylsilanamide titanium (IV) dibenzyl, and mixtures thereof, especially mixtures of positional isomers.

Further illustrative examples of metal complexes for use according to the present invention correspond to the formula:

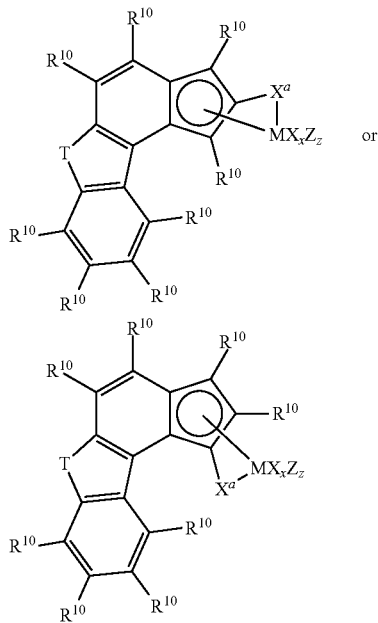

where M is titanium in the +2, +3 or +4 formal oxidation state;

T is —NR$^9$— or —O—;

R$^9$ is hydrocarbyl, silyl, germyl, dihydrocarbylboryl, or halohydrocarbyl or up to 10 atoms not counting hydrogen;

R$^{10}$ independently at each occurrence is hydrogen, hydrocarbyl, trihydrocarbylsilyl, trihydrocarbylsilylhydrocarbyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo-substituted hydrocarbyl, hydrocarbyloxy-substituted hydrocarbyl, silyl-substituted hydrocarbyl, hydrocarbylsiloxy-substituted hydrocarbyl, hydrocarbylsilylamino-substituted hydrocarbyl, di(hydrocarbyl)amino-substituted hydrocarbyl, hydrocarbyleneamino-substituted hydrocarbyl, di(hydrocarbyl)phosphino-substituted hydrocarbyl, hydrocarbylenephosphino-substituted hydrocarbyl, or hydrocarbylsulfido-substituted hydrocarbyl, said R$^{10}$ group having up to 40 atoms not counting hydrogen atoms, and optionally two or more of the foregoing adjacent R$^{10}$ groups may together form a divalent derivative thereby forming a saturated or unsaturated fused ring;

X$^a$ is a divalent moiety lacking in delocalized i-electrons, or such a moiety comprising one σ-bond and a neutral two electron pair able to form a coordinate-covalent bond to M, said X$^a$ comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons or two X groups together are a divalent anionic ligand group;

Z independently at each occurrence is a neutral ligating compound having up to 20 atoms;

x is 0, 1, 2, or 3;

and z is 0 or 1.

Illustratively, T is =N(CH$_3$), X is halo or hydrocarbyl, x is 2, X$^a$ is dimethylsilane, z is 0, and R$^{10}$ at each occurrence is hydrogen, a hydrocarbyl, hydrocarbyloxy, dihydrocarbylamino, hydrocarbyleneamino, dihydrocarbylamino-substituted hydrocarbyl group, or hydrocarbyleneamino-substituted hydrocarbyl group of up to 20 atoms not counting hydrogen, and optionally two R$^{10}$ groups may be joined together.

Illustrative metal complexes of the foregoing formula that may be employed in the practice of the present invention further include the following compounds:

(t-butylamido)dimethyl-[6,7]benzo-[4,5:2',3'](1-methylisoindol)-(3H)-indene-2-yl)silanetitanium (II) 1,4-diphenyl-1,3-butadiene, (t-butylamido)dimethyl-[6,7]benzo-[4,5:2',3'](1-methylisoindol)-(3H)-indene-2-yl)silanetitanium (II) 1,3-pentadiene, (t-butylamido)dimethyl-[6,7]benzo-[4,5:2',3'](1-methylisoindol)-(3H)-indene-2-yl)silanetitanium (III) 2-(N,N-dimethylamino)benzyl, (t-butylamido)dimethyl-[6,7]benzo-[4,5:2',3'](1-methylisoindol)-(3H)-indene-2-yl)silanetitanium (IV) dichloride, (t-butylamido)dimethyl-[6,7]benzo-[4,5:2',3'](1-methylisoindol)-(3H)-indene-2-yl)silanetitanium (IV) dimethyl, (t-butylamido)dimethyl-[6,7]benzo-[4,5:2',3'](1-methylisoindol)-(3H)-indene-2-yl)silanetitanium (IV) dibenzyl, (t-butylamido)dimethyl-[6,7]benzo-[4,5:2',3'](1-methylisoindol)-(3H)-indene-2-yl)silanetitanium (IV) bis(trimethylsilyl), (cyclohexylamido)dimethyl-[6,7]benzo-[4,5:2',3'](1-methylisoindol)-(3H)-indene-2-yl)silanetitanium (II) 1,4-diphenyl-1,3-butadiene, (cyclohexylamido)dimethyl-[6,7]benzo-[4,5:2',3'](1-methylisoindol)-(3H)-indene-2-yl)silanetitanium (II) 1,3-pentadiene, (cyclohexylamido)dimethyl-[6,7]benzo-[4,5:2',3'](1-methylisoindol)-(3H)-indene-2-yl)silanetitanium (III) 2-(N,N-dimethylamino)benzyl, (cyclohexylamido)dimethyl-[6,7]benzo-[4,5:2',3'](1-methylisoindol)-(3H)-indene-2-yl)silanetitanium (IV) dichloride, (cyclohexylamido)dimethyl-[6,7]benzo-[4,5:2',3'](1-methylisoindol)-(3H)-indene-2-yl)silanetitanium (IV) dimethyl, (cyclohexylamido)dimethyl-[6,7]benzo-[4,5:2',3'](1-methylisoindol)-(3H)-indene-2-yl)silanetitanium (IV) dibenzyl, (cyclohexylamido)dimethyl-[6,7]benzo-[4,5:2',3'](1-methylisoindol)-(3H)-indene-2-yl)silanetitanium (IV) bis(trimethylsilyl), (t-butylamido)di(p-methylphenyl)-[6,7]benzo-[4,5:2',3'](1-methylisoindol)-(3H)-indene-2-yl)silanetitanium (II) 1,4-diphenyl-1,3-butadiene, (t-butylamido)di(p-methylphenyl)-[6,7]benzo-[4,5:2',3'](1-methylisoindol)-(3H)-indene-2-yl)silanetitanium (II) 1,3-pentadiene, (t-butylamido)di(p-methylphenyl)-[6,7]benzo-[4,5:2',3'](1-methylisoindol)-(3H)-indene-2-yl)silanetitanium (III) 2-(N,N-dimethylamino)benzyl, (t-butylamido)di(p-methylphenyl)-[6,7]benzo-[4,5:2',3'](1-methylisoindol)-(3H)-indene-2-yl)silanetitanium (IV) dichloride, (t-butylamido)di(p-methylphenyl)-[6,7]benzo-[4,5:2',3'](1-methylisoindol)-(3H)-indene-2-yl)silanetitanium (IV) dimethyl, (t-butylamido)di(p-methylphenyl)-[6,7]benzo-[4,5:2',3'](1-methylisoindol)-(3H)-indene-2-yl)silanetitanium (IV) dibenzyl, (t-butylamido)di(p-methylphenyl)-[6,7]benzo-[4,5:2',3'](1-methylisoindol)-(3H)-indene-2-yl)silanetitanium (IV) bis(trimethylsilyl), (cyclohexylamido)di(p-methylphenyl)-[6,7]benzo-[4,5:2',3'](1-methylisoindol)-(3H)-indene-2-yl)silanetitanium (II) 1,4-diphenyl-1,3-butadiene, (cyclohexylamido)di(p-methylphenyl)-[6,7]benzo-[4,5:2',3'](1-methylisoindol)-(3H)-indene-2-yl)silanetitanium (II) 1,3-pentadiene, (cyclohexylamido)di(p-methylphenyl)-[6,7]benzo-[4,5:2',3'](1-methylisoindol)-(3H)-indene-2-yl)silanetitanium (III) 2-(N,N-dimethylamino)benzyl, (cyclohexylamido)di(p-methylphenyl)-[6,7]benzo-[4,5:2',3'](1-methylisoindol)-(3H)-indene-2-yl)silanetitanium (IV) dichloride, (cyclohexylamido)di(p-methylphenyl)-[6,7]benzo-[4,5:2',3'](1-methylisoindol)-(3H)-indene-2-yl)silanetitanium (IV) dimethyl, (cyclohexylamido)di(p-methylphenyl)-[6,7]benzo-[4,5:2',3'](1-methylisoindol)-(3H)-indene-2-yl)silanetitanium (IV) dibenzyl; and (cyclohexylamido)di(p-methylphenyl)-[6,7]benzo-[4,5:2',3'](1-methylisoindol)-(3H)-indene-2-yl)silanetitanium (IV) bis(trimethylsilyl).

Illustrative Group 4 metal complexes that may be employed in the practice of the present disclosure further include:

(tert-butylamido)(1,1-dimethyl-2,3,4,9,10,$\eta$-1,4,5,6,7,8-hexahydronaphthalenyl)dimethylsilanetitaniumdimethyl (tert-butylamido)(1,1,2,3-tetramethyl-2,3,4,9,10-$\eta$-1,4,5,6,7,8-hexahydronaphthalenyl)dimethylsilanetitaniumdimethyl, (tert-butylamido)(tetramethyl-$\eta^5$-cyclopentadienyl) dimethylsilanetitanium dibenzyl, (tert-butylamido)(tetramethyl-$\eta^5$-cyclopentadienyl)dimethylsilanetitanium dimethyl, (tert-butylamido)(tetramethyl-$\eta^5$-cyclopentadienyl)-1,2-ethanediyltitanium dimethyl, (tert-butylamido)(tetramethyl-$\eta^5$-indenyl)dimethylsilanetitanium dimethyl, (tert-butylamido)(tetramethyl-$\eta^5$-cyclopentadienyl)dimethylsilane titanium (III) 2-(dimethylamino)benzyl;

(tert-butylamido)(tetramethyl-$\eta^5$-cyclopentadienyl)dimethylsilanetitanium (III) allyl, (tert-butylamido)(tetramethyl-$\eta^5$-cyclopentadienyl)dimethylsilanetitanium (III) 2,4-dimethylpentadienyl, (tert-butylamido)(tetramethyl-$\eta^5$-cyclopentadienyl)dimethylsilanetitanium (II) 1,4-diphenyl-1,3-butadiene, (tert-butylamido)(tetramethyl-$\eta^5$-cyclopentadienyl)dimethylsilanetitanium (II) 1,3-pentadiene, (tert-butylamido)(2-methylindenyl)dimethylsilanetitanium (II) 1,4-diphenyl-1,3-butadiene, (tert-butylamido)(2-methylindenyl)dimethylsilanetitanium (II) 2,4-hexadiene, (tert-butylamido)(2-methylindenyl)dimethylsilanetitanium (IV) 2,3-dimethyl-1,3-butadiene, (tert-butylamido)(2-methylindenyl)dimethylsilanetitanium (IV) isoprene, (tert-butylamido)(2-methylindenyl)dimethylsilanetitanium (IV) 1,3-butadiene, (tert-butylamido)(2,3-dimethylindenyl)dimethylsilanetitanium (IV) 2,3-dimethyl-1,3-butadiene, (tert-butylamido)(2,3-dimethylindenyl)dimethylsilanetitanium (IV) isoprene, (tert-butylamido)(2,3-dimethylindenyl)dimethylsilanetitanium (IV) dimethyl, (tert-butylamido)(2,3-dimethylindenyl)dimethylsilanetitanium (IV) dibenzyl, (tert-butylamido)(2,3-dimethylindenyl)dimethylsilanetitanium (IV) 1,3-butadiene, (tert-butylamido)(2,3-dimethylindenyl)dimethylsilanetitanium (II) 1,3-pentadiene, (tert-butylamido)(2,3-dimethylindenyl)dimethylsilanetitanium (II) 1,4-diphenyl-1,3-butadiene, (tert-butylamido)(2-methylindenyl)dimethylsilanetitanium (II) 1,3-pentadiene, (tert-butylamido)(2-methylindenyl)dimethylsilanetitanium (IV) dimethyl, (tert-butylamido)(2-methylindenyl)dimethylsilanetitanium (IV) dibenzyl, (tert-butylamido)(2-methyl-4-phenylindenyl)dimethylsilanetitanium (II) 1,4-diphenyl-1,3-butadiene, (tert-butylamido)(2-methyl-4-phenylindenyl)dimethylsilanetitanium (II) 1,3-pentadiene, (tert-butylamido)(2-methyl-4-phenylindenyl)dimethylsilanetitanium (II) 2,4-hexadiene, (tert-butylamido)(tetramethyl-$\eta^5$-cyclopentadienyl)dimethyl-silanetitanium (IV) 1,3-butadiene, (tert-butylamido)(tetramethyl-$\eta^5$-cyclopentadienyl)dimethylsilanetitanium (IV) 2,3-dimethyl-1,3-butadiene, (tert-butylamido)(tetramethyl-$\eta^5$-cyclopentadienyl)dimethylsilanetitanium (IV) isoprene, (tert-butylamido)(tetramethyl-$\eta^5$-cyclopentadienyl)dimethyl-silanetitanium (II) 1,4-dibenzyl-1,3-butadiene, (tert-butylamido)(tetramethyl-$\eta^5$-cyclopentadienyl)dimethylsilanetitanium (II) 2,4-hexadiene, (tert-butylamido)(tetramethyl-$\eta^5$-cyclopentadienyl)dimethyl-silanetitanium (II) 3-methyl-1,3-pentadiene, (tert-butylamido)(2,4-dimethylpentadien-3-yl)dimethyl-silanetitaniumdimethyl, (tert-butylamido)(6,6-dimethylcyclohexadienyl)dimethylsilanetitaniumdimethyl, (tert-butylamido)(1,1-dimethyl-2,3,4,9,10-$\eta$-1,4,5,6,7,8-hexahydronaphthalen-4-yl)dimethylsilanetitaniumdimethyl, (tert-butylamido)(1,1,2,3-tetramethyl-2,3,4,9,10-$\eta$-1,4,5,6,7,8-hexahydronaphthalen-4-yl)dimethylsilanetitaniumdimethyl, (tert-butylamido)(tetramethyl-$\eta^5$-cyclopentadienyl methylphenylsilanetitanium (IV) dimethyl, (tert-butylamido)(tetramethyl-$\eta^5$-cyclopentadienyl methylphenylsilanetitanium (II) 1,4-diphenyl-1,3-butadiene, 1-(tert-butylamido)-2-(tetramethyl-$\eta^5$-cyclopentadienyl) ethanediyltitanium (IV) dimethyl, and 1-(tert-butylamido)-2-(tetramethyl-$\eta^5$-cyclopentadienyl) ethanediyl-titanium (II) 1,4-diphenyl-1,3-butadiene.

Other delocalized, $\pi$-bonded complexes, especially those containing other Group 4 metals, will, of course, be apparent to those skilled in the art, and are disclosed among other places in: WO 03/78480, WO 03/78483, WO 02/92610, WO 02/02577, US 2003/0004286 and U.S. Pat. Nos. 6,515,155, 6,555,634, 6,150,297, 6,034,022, 6,268,444, 6,015,868, 5,866,704, and 5,470,993.

Additional examples of metal complexes that are usefully employed as catalysts are complexes of polyvalent Lewis bases, such as compounds corresponding to the formula:

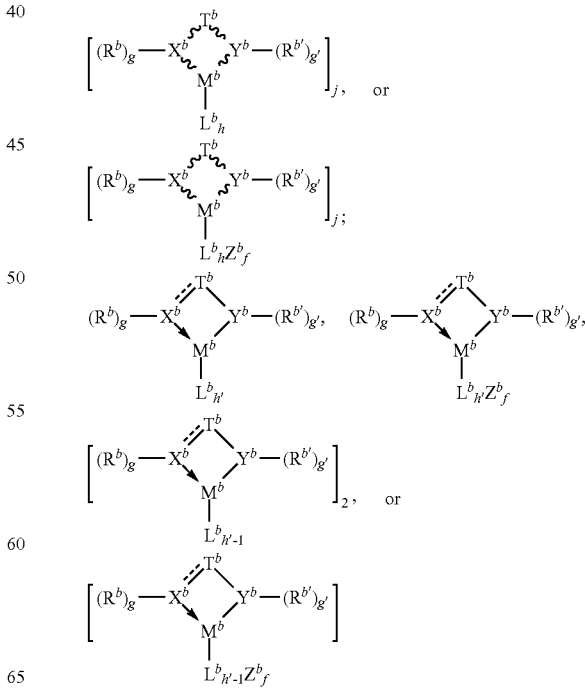

wherein $T^b$ is a bridging group, preferably containing 2 or more atoms other than hydrogen, $X^b$ and $Y^b$ are each independently selected from the group consisting of nitrogen, sulfur, oxygen and phosphorus; more preferably both $X^b$ and $Y^b$ are nitrogen, $R^b$ and $R^{b'}$ independently each occurrence are hydrogen or $C_{1-50}$ hydrocarbyl groups optionally containing one or more heteroatoms or inertly substituted derivative thereof. Non-limiting examples of suitable $R^b$ and $R^{b'}$ groups include alkyl, alkenyl, aryl, aralkyl, (poly)alkylaryl and cycloalkyl groups, as well as nitrogen, phosphorus, oxygen and halogen substituted derivatives thereof. Specific examples of suitable Rb and Rb' groups include methyl, ethyl, isopropyl, octyl, phenyl, 2,6-dimethylphenyl, 2,6-di(isopropyl)phenyl, 2,4,6-trimethylphenyl, pentafluorophenyl, 3,5-trifluoromethylphenyl, and benzyl;

g and g' are each independently 0 or 1;

$M^b$ is a metallic element selected from Groups 3 to 15, or the Lanthanide series of the Periodic Table of the Elements. Preferably, $M^b$ is a Group 3-13 metal, more preferably $M^b$ is a Group 4-10 metal;

$L^b$ is a monovalent, divalent, or trivalent anionic ligand containing from 1 to 50 atoms, not counting hydrogen. Examples of suitable $L^b$ groups include halide; hydride; hydrocarbyl, hydrocarbyloxy; di(hydrocarbyl)amido, hydrocarbyleneamido, di(hydrocarbyl)phosphido; hydrocarbylsulfido; hydrocarbyloxy, tri(hydrocarbylsilyl)alkyl; and carboxylates. More preferred $L^b$ groups are C1-20 alkyl, $C_{7-20}$ aralkyl, and chloride;

h and h' are each independently an integer from 1 to 6, preferably from 1 to 4, more preferably from 1 to 3, and j is 1 or 2, with the value h×j selected to provide charge balance;

$Z^b$ is a neutral ligand group coordinated to $M^b$, and containing up to 50 atoms not counting hydrogen. Preferred $Z^b$ groups include aliphatic and aromatic amines, phosphines, and ethers, alkenes, alkadienes, and inertly substituted derivatives thereof. Suitable inert substituents include halogen, alkoxy, aryloxy, alkoxycarbonyl, aryloxycarbonyl, di(hydrocarbyl)amine, tri(hydrocarbyl)silyl, and nitrile groups. Preferred $Z^b$ groups include triphenylphosphine, tetrahydrofuran, pyridine, and 1,4-diphenylbutadiene;

f is an integer from 1 to 3;

two or three of $T^b$, $R^b$ and $R^{b'}$ may be joined together to form a single or multiple ring structure;

h is an integer from 1 to 6, preferably from 1 to 4, more preferably from 1 to 3;

∼∼∼ indicates any form of electronic interaction, especially coordinate or covalent bonds, including multiple bonds, arrows signify coordinate bonds, and dotted lines indicate optional double bonds.

In one embodiment, it is preferred that $R^b$ have relatively low steric hindrance with respect to $X^b$. In this embodiment, most preferred $R^b$ groups are straight chain alkyl groups, straight chain alkenyl groups, branched chain alkyl groups wherein the closest branching point is at least 3 atoms removed from $X^b$, and halo, dihydrocarbylamino, alkoxy or trihydrocarbylsilyl substituted derivatives thereof. Highly preferred $R^b$ groups in this embodiment are C1-8 straight chain alkyl groups.

At the same time, in this embodiment $R^{b'}$ preferably has relatively high steric hindrance with respect to $Y^b$. Non-limiting examples of suitable $R^{b'}$ groups for this embodiment include alkyl or alkenyl groups containing one or more secondary or tertiary carbon centers, cycloalkyl, aryl, alkaryl, aliphatic or aromatic heterocyclic groups, organic or inorganic oligomeric, polymeric or cyclic groups, and halo, dihydrocarbylamino, alkoxy or trihydrocarbylsilyl substituted derivatives thereof. Preferred $R^{b'}$ groups in this embodiment contain from 3 to 40, more preferably from 3 to 30, and most preferably from 4 to 20 atoms not counting hydrogen and are branched or cyclic. Examples of preferred $T^b$ groups are structures corresponding to the following formulas:

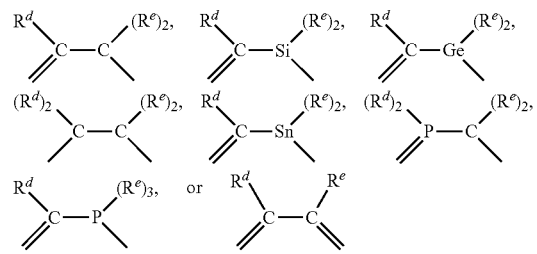

wherein

Each $R^d$ is C1-10 hydrocarbyl group, preferably methyl, ethyl, n-propyl, propyl, t-butyl, phenyl, 2,6-dimethylphenyl, benzyl, or tolyl. Each W is C1-10 hydrocarbyl, preferably methyl, ethyl, n-propyl, i-propyl, t-butyl, phenyl, 2,6-dimethylphenyl, benzyl, or tolyl. In addition, two or more $R^d$ or $R^e$ groups, or mixtures of Rd and Re groups may together form a polyvalent derivative of a hydrocarbyl group, such as, 1,4-butylene, 1,5-pentylene, or a multicyclic, fused ring, polyvalent hydrocarbyl- or heterohydrocarbyl-group, such as naphthalene-1,8-diyl.

Suitable examples of the foregoing polyvalent Lewis base complexes include:

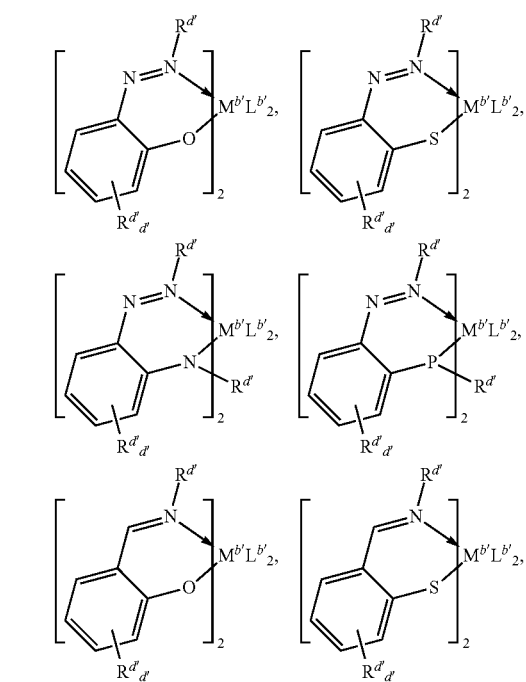

-continued

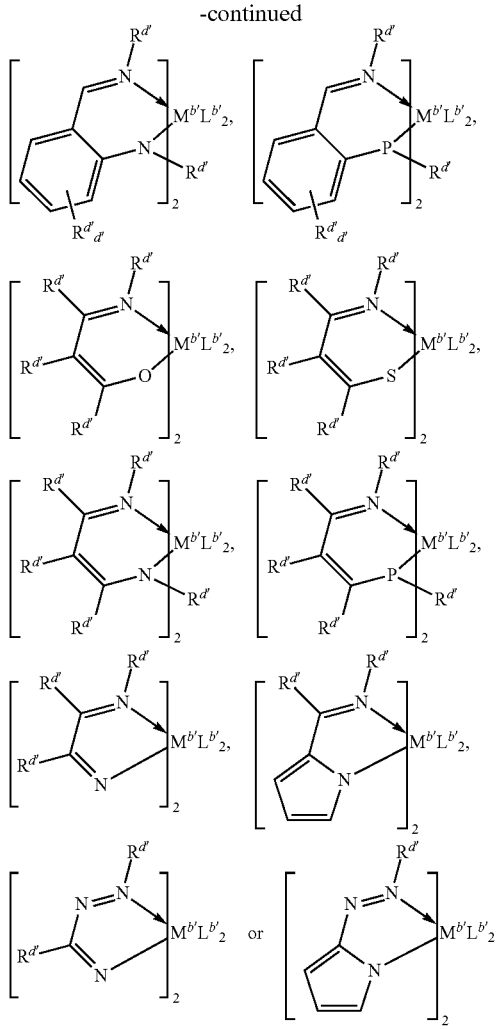

wherein R$^{d'}$ at each occurrence is independently selected from the group consisting of hydrogen and C1-50 hydrocarbyl groups optionally containing one or more heteroatoms, or inertly substituted derivative thereof, or further optionally, two adjacent R$^{d'}$ groups may together form a divalent bridging group;

d' is 4;

M$^{b'}$ is a Group 4 metal, preferably titanium or hafnium, or a Group 10 metal, preferably Ni or Pd;

L$^{b'}$ is a monovalent ligand of up to 50 atoms not counting hydrogen, preferably halide or hydrocarbyl, or two L$^{b'}$ groups together are a divalent or neutral ligand group, preferably a C$_{2-50}$ hydrocarbylene, hydrocarbadiyl or diene group.

The polyvalent Lewis base complexes for use in the present invention especially include Group 4 metal derivatives, especially hafnium derivatives of hydrocarbylamine substituted heteroaryl compounds corresponding to the formula:

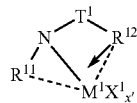

wherein:
R$^{11}$ is selected from alkyl, cycloalkyl, heteroalkyl, cycloheteroalkyl, aryl, and inertly substituted derivatives thereof containing from 1 to 30 atoms not counting hydrogen or a divalent derivative thereof;
T$^1$ is a divalent bridging group of from 1 to 41 atoms other than hydrogen, preferably 1 to 20 atoms other than hydrogen, and most preferably a mono- or di-C1-20 hydrocarbyl substituted methylene or silane group; and
R$^{12}$ is a C$_{5-20}$ heteroaryl group containing Lewis base functionality, especially a pyridin-2-yl- or substituted pyridin-2-yl group or a divalent derivative thereof;
M$^1$ is a Group 4 metal, preferably hafnium;
X$^1$ is an anionic, neutral or dianionic ligand group;
x' is a number from 0 to 5 indicating the number of such X$^1$ groups; and bonds, optional bonds and electron donative interactions are represented by lines, dotted lines and arrows respectively.

Suitable complexes are those wherein ligand formation results from hydrogen elimination from the amine group and optionally from the loss of one or more additional groups, especially from R$^{12}$. In addition, electron donation from the Lewis base functionality, preferably an electron pair, provides additional stability to the metal center. Suitable metal complexes correspond to the formula:

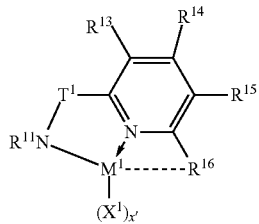

wherein M$^1$, X$^1$, x', R$^{11}$ and T$^1$ are as previously defined, R$^{13}$, R$^{14}$, R$^{15}$ and R$^{16}$ are hydrogen, halo, or an alkyl, cycloalkyl, heteroalkyl, heterocycloalkyl, aryl, or silyl group of up to 20 atoms not counting hydrogen, or adjacent R$^{13}$, R$^{14}$, R$^{15}$ or R$^{16}$ groups may be joined together thereby forming fused ring derivatives, and bonds, optional bonds and electron pair donative interactions are represented by lines, dotted lines and arrows respectively. Suitable examples of the foregoing metal complexes correspond to the formula:

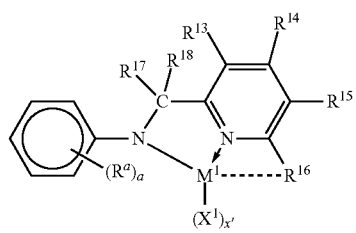

wherein
M$^1$, X$^1$, and x' are as previously defined,
R$^{13}$, R$^{14}$, R$^{15}$ and R$^{16}$ are as previously defined, preferably R$^{13}$, R$^{14}$, and R$^{15}$ are hydrogen, or C1-4 alkyl, and R$^{16}$ is C$_{6-20}$ aryl, most preferably naphthalenyl;
R$^a$ independently at each occurrence is C$_{1-4}$ alkyl, and a is 1-5, most preferably R$^a$ in two ortho-positions to the nitrogen is isopropyl or t-butyl;

R[17] and R[18] independently at each occurrence are hydrogen, halogen, or a $C_{1-20}$ alkyl or aryl group, most preferably one of R[17] and R[18] is hydrogen and the other is a C6-20 aryl group, especially 2-isopropyl, phenyl or a fused polycyclic aryl group, most preferably an anthracenyl group, and bonds, optional bonds and electron pair donative interactions are represented by lines, dotted lines and arrows respectively.

Exemplary metal complexes for use herein as catalysts correspond to the formula:

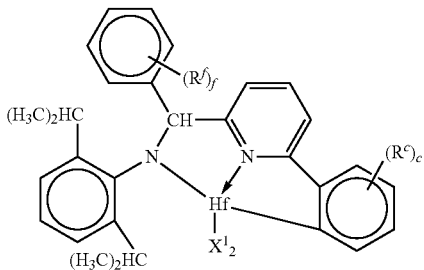

wherein $X^1$ at each occurrence is halide, N,N-dimethylamido, or $C_{1-4}$ alkyl, and preferably at each occurrence $X^1$ is methyl;

$R^f$ independently at each occurrence is hydrogen, halogen, C1-20 alkyl, or C6-20 aryl, or two adjacent $R^f$ groups are joined together thereby forming a ring, and f is 1-5; and $R^c$ independently at each occurrence is hydrogen, halogen, $C_{1-20}$ alkyl, or $C_{6-20}$ aryl, or two adjacent $R^c$ groups are joined together thereby forming a ring, and c is 1-5.

Suitable examples of metal complexes for use as catalysts according to the present invention are complexes of the following formulas:

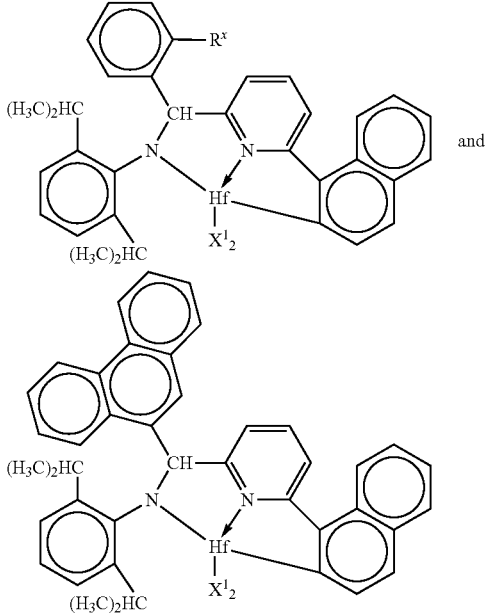

wherein $R^x$ is C1-4 alkyl or cycloalkyl, preferably methyl, isopropyl, t-butyl or cyclohexyl; and $X^1$ at each occurrence is halide, N,N-dimethylamido, or C1-4 alkyl, preferably methyl.

Examples of metal complexes usefully employed as catalysts according to the present invention include:

[N-(2,6-di(1-methylethyl)phenyl)amido)(o-tolyl)(α-naphthalen-2-diyl(6-pyridin-2-diyl)methane)]hafnium dimethyl;

[N-(2,6-di(1-methylethyl)phenyl)amido)(o-tolyl)(α-naphthalen-2-diyl(6-pyridin-2-diyl)methane)]hafnium di(N,N-dimethylamido);

[N-(2,6-di(1-methylethyl)phenyl)amido)(o-tolyl)(α-naphthalen-2-diyl(6-pyridin-2-diyl)methane)]hafnium dichloride;

[N-(2,6-di(1-methylethyl)phenyl)amido)(2-isopropylphenyl) (α-naphthalen-2-diyl(6-pyridin-2-diyl)methane)]hafnium dimethyl;

[N-(2,6-di(1-methylethyl)phenyl)amido)(2-isopropylphenyl) (α-naphthalen-2-diyl(6-pyridin-2-diyl)methane)]hafnium di(N,N-dimethylamido);

[N-(2,6-di(1-methylethyl)phenyl)amido)(2-isopropylphenyl)(α-naphthalen-2-diyl(6-pyridin-2-diyl)methane)]hafnium dichloride;

[N-(2,6-di(1-methylethyl)phenyl)amido)(phenanthren-5-yl) (α-naphthalen-2-diyl(6-pyridin-2-diyl)methane)]hafnium dimethyl;

[N-(2,6-di(1-methylethyl)phenyl)amido)(phenanthren-5-yl) (α-naphthalen-2-diyl(6-pyridin-2-diyl)methane)]hafnium di(N,N-dimethylamido); and

[N-(2,6-di(1-methylethyl)phenyl)amido)(phenanthren-5-yl) (α-naphthalen-2-diyl(6-pyridin-2-diyl)methane)]hafnium dichloride.

Under the reaction conditions used to prepare the metal complexes used in the present disclosure, the hydrogen of the 2-position of the α-naphthalene group substituted at the 6-position of the pyridin-2-yl group is subject to elimination, thereby uniquely forming metal complexes wherein the metal is covalently bonded to both the resulting amide group and to the 2-position of the α-naphthalenyl group, as well as stabilized by coordination to the pyridinyl nitrogen atom through the electron pair of the nitrogen atom.

Additional suitable metal complexes of polyvalent Lewis bases for use herein include compounds corresponding to the formula:

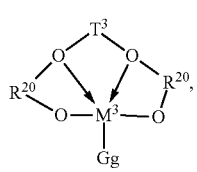

wherein:

$R^{20}$ is an aromatic or inertly substituted aromatic group containing from 5 to 20 atoms not counting hydrogen, or a polyvalent derivative thereof;

$T^3$ is a hydrocarbylene or hydrocarbyl silane group having from 1 to 20 atoms not counting hydrogen, or an inertly substituted derivative thereof;

$M^3$ is a Group 4 metal, preferably zirconium or hafnium;

G is an anionic, neutral or dianionic ligand group; preferably a halide, hydrocarbyl, silane, trihydrocarbylsilylhydrocarbyl, trihydrocarbylsilyl, or dihydrocarbylamide group having up to 20 atoms not counting hydrogen;

g is a number from 1 to 5 indicating the number of such G groups; and bonds and electron donative interactions are represented by lines and arrows respectively.

Illustratively, such complexes correspond to the formula:

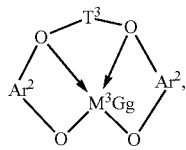

wherein:

$T^3$ is a divalent bridging group of from 2 to 20 atoms not counting hydrogen, preferably a substituted or unsubstituted, C3-6 alkylene group;

and $Ar^2$ independently at each occurrence is an arylene or an alkyl- or aryl-substituted arylene group of from 6 to 20 atoms not counting hydrogen;

$M^3$ is a Group 4 metal, preferably hafnium or zirconium;

G independently at each occurrence is an anionic, neutral or dianionic ligand group;

g is a number from 1 to 5 indicating the number of such X groups; and electron donative interactions are represented by arrows.

Suitable examples of metal complexes of foregoing formula include the following compounds

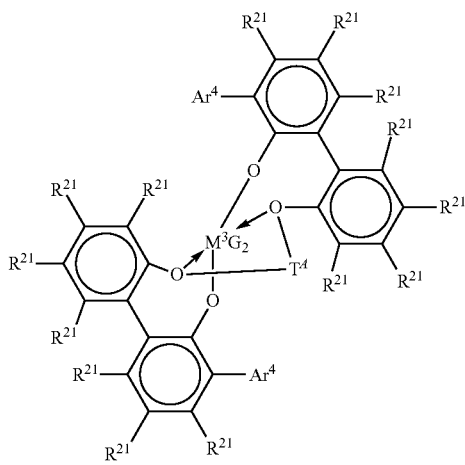

where $M^3$ is Hf or Zr;

$Ar^4$ is $C_{6-20}$ aryl or inertly substituted derivatives thereof, especially 3,5-di(isopropyl)phenyl, 3,5-di(isobutyl)phenyl, dibenzo-1H-pyrrole-1-yl, or anthracen-5-yl, and $T^4$ independently at each occurrence comprises a $C_{3-6}$ alkylene group, a $C_{3-6}$ cycloalkylene group, or an inertly substituted derivative thereof;

$R^{21}$ independently at each occurrence is hydrogen, halo, hydrocarbyl, trihydrocarbylsilyl, or trihydrocarbylsilylhydrocarbyl of up to 50 atoms not counting hydrogen; and G, independently at each occurrence is halo or a hydrocarbyl or trihydrocarbylsilyl group of up to 20 atoms not counting hydrogen, or 2 G groups together are a divalent derivative of the foregoing hydrocarbyl or trihydrocarbylsilyl groups.

Suitable compounds are compounds of the formulas:

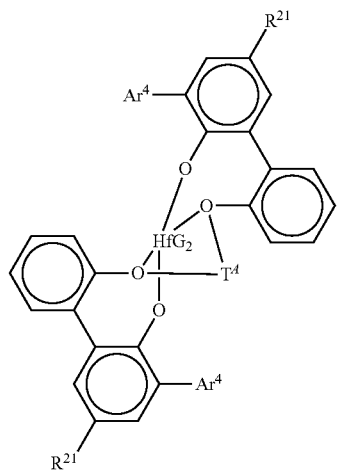

wherein $Ar^4$ is 3,5-di(isopropyl)phenyl, 3,5-di(isobutyl)phenyl, dibenzo-1H-pyrrole-1-yl, or anthracen-5-yl, $R^{21}$ is hydrogen, halo, or C1-4 alkyl, especially methyl $T^4$ is propan-1,3-diyl or butan-1,4-diyl, and G is chloro, methyl or benzyl.

An exemplary metal complex of the foregoing formula is:

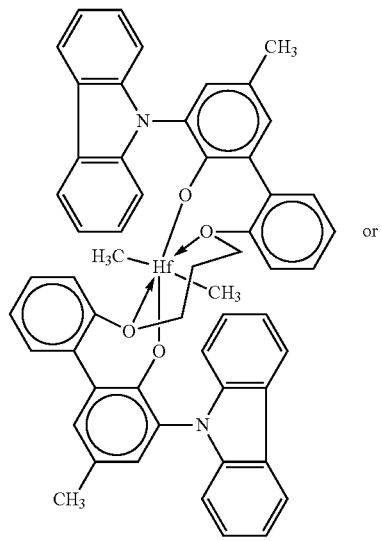

or

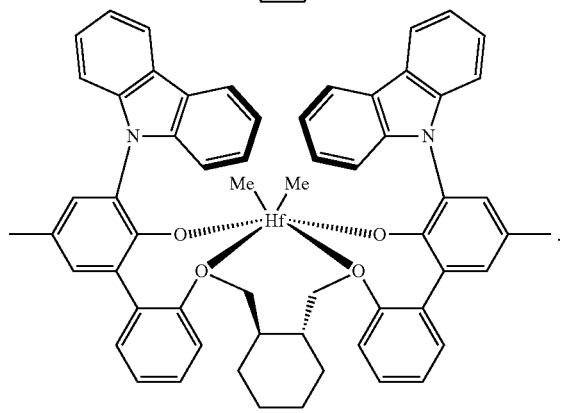

Suitable metal complexes for use according to the present disclosure further include compounds corresponding to the formula:

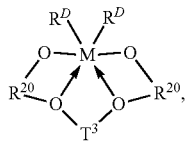

where:

M is zirconium or hafnium;

$R^{20}$ independently at each occurrence is a divalent aromatic or inertly substituted aromatic group containing from 5 to 20 atoms not counting hydrogen;

$T^3$ is a divalent hydrocarbon or silane group having from 3 to 20 atoms not counting hydrogen, or an inertly substituted derivative thereof; and $R^D$ independently at each occurrence is a monovalent ligand group of from 1 to 20 atoms, not counting hydrogen, or two $R^D$ groups together are a divalent ligand group of from 1 to 20 atoms, not counting hydrogen.

Such complexes may correspond to the formula:

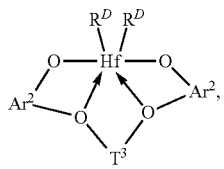

wherein:

$Ar^2$ independently at each occurrence is an arylene or an alkyl-, aryl-, alkoxy- or amino-substituted arylene group of from 6 to 20 atoms not counting hydrogen or any atoms of any substituent;

$T^3$ is a divalent hydrocarbon bridging group of from 3 to 20 atoms not counting hydrogen, preferably a divalent substituted or unsubstituted $C_{3-6}$ aliphatic, cycloaliphatic, or bis(alkylene)-substituted cycloaliphatic group having at least 3 carbon atoms separating oxygen atoms; and $R^D$ independently at each occurrence is a monovalent ligand group of from 1 to 20 atoms, not counting hydrogen, or two $R^D$ groups together are a divalent ligand group of from 1 to 40 atoms, not counting hydrogen.

Further examples of metal complexes suitable for use herein include compounds of the formula:

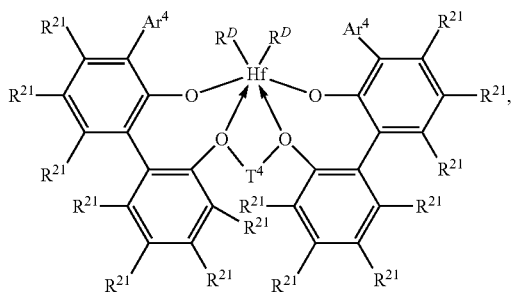

where $Ar^4$ independently at each occurrence is $C_{6-20}$ aryl or inertly substituted derivatives thereof, especially 3,5-di(isopropyl)phenyl, 3,5-di(isobutyl)phenyl, dibenzo-1H-pyrrole-1-yl, naphthyl, anthracen-5-yl, 1,2,3,4,6,7,8,9-octahydroanthracen-5-yl;

$T^4$ independently at each occurrence is a propylene-1,3-diyl group, a bis(alkylene)cyclohexan-1,2-diyl group, or an inertly substituted derivative thereof substituted with from 1 to 5 alkyl, aryl or aralkyl substituents having up to 20 carbons each;

$R^{21}$ independently at each occurrence is hydrogen, halo, hydrocarbyl, trihydrocarbylsilyl, trihydrocarbylsilylhydrocarbyl, alkoxy or amino of up to 50 atoms not counting hydrogen; and $R^D$, independently at each occurrence is halo or a hydrocarbyl or trihydrocarbylsilyl group of up to 20 atoms not counting hydrogen, or 2 $R^D$ groups together are a divalent hydrocarbylene, hydrocarbadiyl or trihydrocarbylsilyl group of up to 40 atoms not counting hydrogen.

Exemplary metal complexes are compounds of the formula:

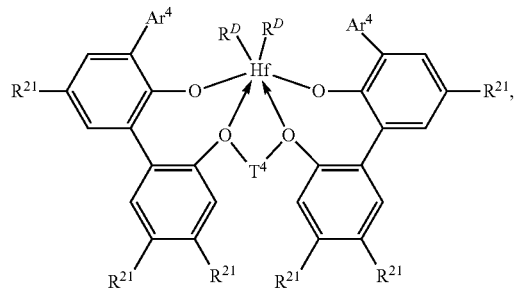

where, $Ar^4$, independently at each occurrence, is 3,5-di(isopropyl)phenyl, 3,5-di(isobutyl)phenyl, dibenzo-1H-pyrrole-1-yl, or anthracen-5-yl, $R^{21}$ independently at each occurrence is hydrogen, halo, hydrocarbyl, trihydrocarbylsilyl, trihydrocarbylsilylhydrocarbyl, alkoxy or amino of up to 50 atoms not counting hydrogen;

$T^4$ is propan-1,3-diyl or bis(methylene)cyclohexan-1,2-diyl; and $R^D$, independently at each occurrence is halo or a hydrocarbyl or trihydrocarbylsilyl group of up to 20 atoms not counting hydrogen, or 2 $R^D$ groups together are a hydrocarbylene, hydrocarbadiyl or hydrocarbylsilanediyl group of up to 40 atoms not counting hydrogen.

Suitable metal complexes according to the present disclosure correspond to the formulas:

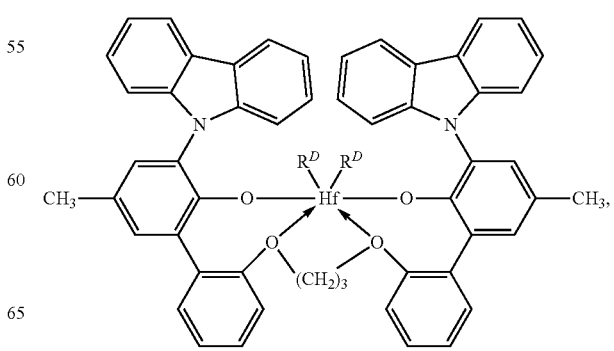

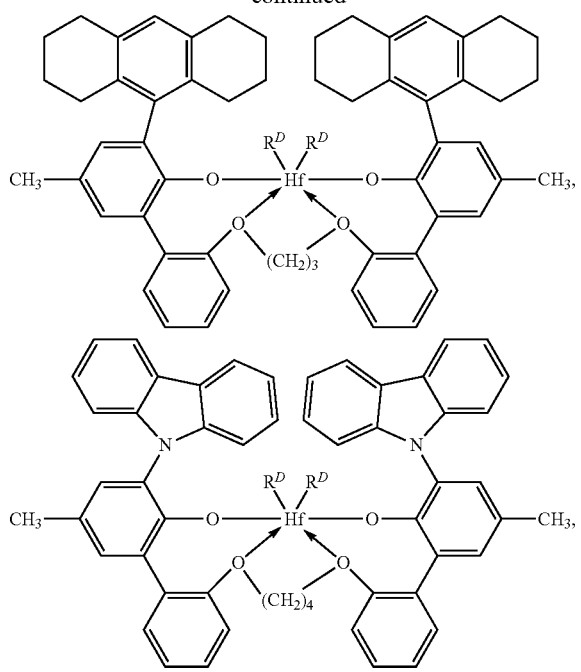
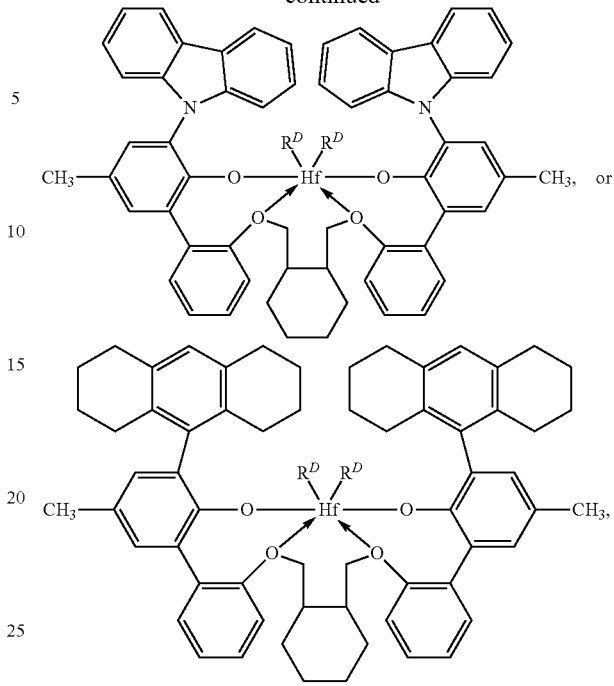
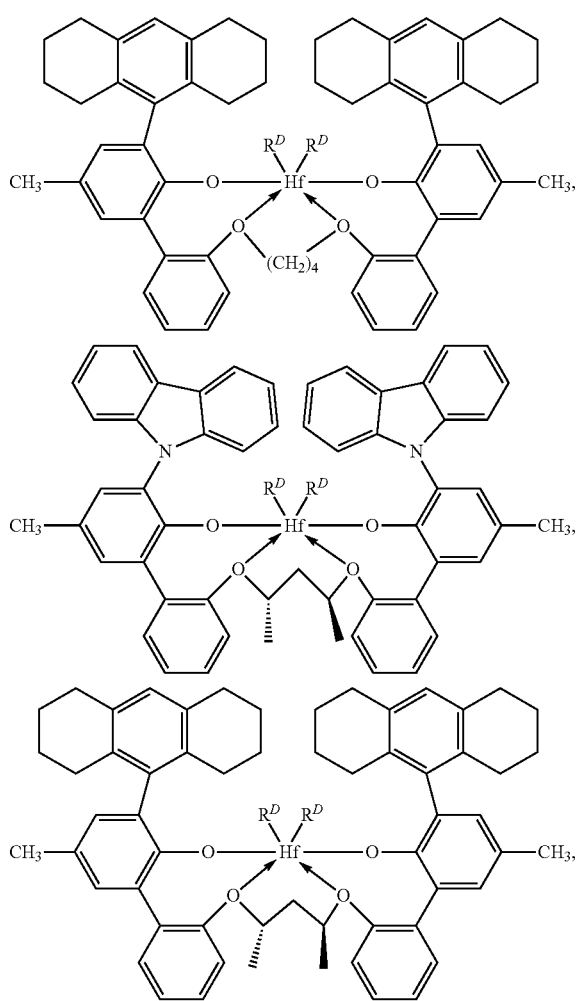

wherein, $R^D$ independently at each occurrence is chloro, methyl or benzyl.

Specific examples of suitable metal complexes are the following compounds:
A) bis((2-oxoyl-3-(1,2,3,4,6,7,8,9-octahydroanthracen-5-yl)-5-(methyl)phenyl)-2-phenoxy)-1,3-propanediylhafnium (IV) dimethyl,
bis((2-oxoyl-3-(1,2,3,4,6,7,8,9-octahydroanthracen-5-yl)-5-(methyl)phenyl)-2-phenoxy)-1,3-propanediylhafnium (IV) dichloride,
bis((2-oxoyl-3-(1,2,3,4,6,7,8,9-octahydroanthracen-5-yl)-5-(methyl)phenyl)-2-phenoxy)-1,3-propanediylhafnium (IV) dibenzyl,
bis((2-oxoyl-3-(dibenzo-1H-pyrrole-1-yl)-5-(methyl)phenyl)-2-phenoxy)-1,3-propanediylhafnium (IV) dimethyl,
bis((2-oxoyl-3-(dibenzo-1H-pyrrole-1-yl)-5-(methyl)phenyl)-2-phenoxy)-1,3-propanediylhafnium (IV) dichloride,
bis((2-oxoyl-3-(dibenzo-1H-pyrrole-1-yl)-5-(methyl)phenyl)-2-phenoxy)-1,3-propanediylhafnium (IV) dibenzyl,
B) bis((2-oxoyl-3-(1,2,3,4,6,7,8,9-octahydroanthracen-5-yl)-5-(methyl)phenyl)-2-phenoxymethyl)-1,4-butanediylhafnium (IV) dimethyl,
bis((2-oxoyl-3-(1,2,3,4,6,7,8,9-octahydroanthracen-5-yl)-5-(methyl)phenyl)-2-phenoxymethyl)-1,4-butanediylhafnium (IV) dichloride,
bis((2-oxoyl-3-(1,2,3,4,6,7,8,9-octahydroanthracen-5-yl)-5-(methyl)phenyl)-2-phenoxymethyl)-1,4-butanediylhafnium (IV) dibenzyl,
bis((2-oxoyl-3-(dibenzo-1H-pyrrole-1-yl)-5-(methyl)phenyl)-2-phenoxymethyl)-1,4-butanediylhafnium (IV) dimethyl,
bis((2-oxoyl-3-(dibenzo-1H-pyrrole-1-yl)-5-(methyl)phenyl)-2-phenoxymethyl)-1,4-butanediylhafnium (IV) dichloride,
bis((2-oxoyl-3-(dibenzo-1H-pyrrole-1-yl)-5-(methyl)phenyl)-2-phenoxymethyl)-1,4-butanediylhafnium (IV) dibenzyl,
C) bis((2-oxoyl-3-(1,2,3,4,6,7,8,9-octahydroanthracen-5-yl)-5-(methyl)phenyl)-2-phenoxy)-2,4-pentanediylhafnium (IV) dimethyl, bis((2-oxoyl-3-(1,2,3,4,6,7,8,9-octahydroanthracen-5-yl)-5-(methyl)phenyl)-2-phenoxy)-2,4-pentanediylhafnium (IV) dichloride,
bis((2-oxoyl-3-(1,2,3,4,6,7,8,9-octahydroanthracen-5-yl)-5-(methyl)phenyl)-2-phenoxy)-2,4-pentanediylhafnium (IV) dibenzyl,
bis((2-oxoyl-3-(dibenzo-1H-pyrrole-1-yl)-5-(methyl)phenyl)-2-phenoxy)-2,4-pentanediylhafnium (IV) dimethyl,
bis((2-oxoyl-3-(dibenzo-1H-pyrrole-1-yl)-5-(methyl)phenyl)-2-phenoxy)-2,4-pentanediylhafnium (IV) dichloride,
bis((2-oxoyl-3-(dibenzo-1H-pyrrole-1-yl)-5-(methyl)phenyl)-2-phenoxy)-2,4-pentanediylhafnium (IV) dibenzyl,
D) bis((2-oxoyl-3-(1,2,3,4,6,7,8,9-octahydroanthracen-5-yl)-5-(methyl)phenyl)-2-phenoxymethyl)-methylenetrans-1,2-cyclohexanediylhafnium (IV) dimethyl,
bis((2-oxoyl-3-(1,2,3,4,6,7,8,9-octahydroanthracen-5-yl)-5-(methyl)phenyl)-2-phenoxymethyl)-methylenetrans-1,2-cyclohexanediylhafnium (IV) dichloride,
bis((2-oxoyl-3-(1,2,3,4,6,7,8,9-octahydroanthracen-5-yl)-5-(methyl)phenyl)-2-phenoxymethyl)-methylenetrans-1,2-cyclohexanediylhafnium (IV) dibenzyl,
bis((2-oxoyl-3-(dibenzo-1H-pyrrole-1-yl)-5-(methyl)phenyl)-2-phenoxymethyl)-methylenetrans-1,2-cyclohexanediylhafnium (IV) dimethyl,
bis((2-oxoyl-3-(dibenzo-1H-pyrrole-1-yl)-5-(methyl)phenyl)-2-phenoxymethyl)-methylenetrans-1,2-cyclohexanediylhafnium (IV) dichloride, and
bis((2-oxoyl-3-(dibenzo-1H-pyrrole-1-yl)-5-(methyl)phenyl)-2-phenoxymethyl)-methylenetrans-1,2-cyclohexanediylhafnium (IV) dibenzyl.

The foregoing metal complexes may be conveniently prepared by standard metallation and ligand exchange procedures involving a source of the transition metal and a neutral polyfunctional ligand source. The techniques employed are the same as or analogous to those disclosed in U.S. Pat. No. 6,827,976 and US2004/0010103, and elsewhere.

The metal complex is activated to form the active catalyst composition by combination with the cocatalyst. The activation may occur prior to addition of the catalyst composition to the reactor with or without the presence of other components of the reaction mixture, or in situ through separate addition of the metal complex and activating cocatalyst to the reactor.

The foregoing polyvalent Lewis base complexes are conveniently prepared by standard metallation and ligand exchange procedures involving a source of the Group 4 metal and the neutral polyfunctional ligand source. In addition, the complexes may also be prepared by means of an amide elimination and hydrocarbylation process starting from the corresponding Group 4 metal tetraamide and a hydrocarbylating agent, such as trimethylaluminum. Other techniques may be used as well. These complexes are known from the disclosures of, among others, U.S. Pat. Nos. 6,320,005, 6,103,657, WO 02/38628, WO 03/40195, and U.S. Ser. No. 04/022,0050.

Catalysts having high comonomer incorporation properties are also known to reincorporate in situ prepared long chain olefins resulting incidentally during the polymerization through β-hydride elimination and chain termination of growing polymer, or other process. The concentration of such long chain olefins is particularly enhanced by use of continuous solution polymerization conditions at high conversions, especially ethylene conversions of 95 percent or greater, more preferably ethylene at ethylene conversions of 97 percent or greater. Under such conditions a small but detectable quantity of olefin terminated polymer may be reincorporated into a growing polymer chain, resulting in the formation of long chain branches, that is, branches of a carbon length greater than would result from other deliberately added comonomer. Moreover, such chains reflect the presence of other comonomers present in the reaction mixture. That is, the chains may include short chain or long chain branching as well, depending on the comonomer composition of the reaction mixture. Long chain branching of olefin polymers is further described in U.S. Pat. Nos. 5,272,236, 5,278,272, and 5,665,800.

Alternatively, branching, including hyper-branching, may be induced in a particular segment of the present multi-block copolymers by the use of specific catalysts known to result in "chain-walking" in the resulting polymer. For example, certain homogeneous bridged bis indenyl- or partially hydrogenated bis indenyl-zirconium catalysts, disclosed by Kaminski, et al., *J. Mol. Catal. A: Chemical,* 102 (1995) 59-65; Zambelli, et al., *Macromolecules,* 1988, 21, 617-622; or Dias, et al., *J. Mol. Catal. A: Chemical,* 185 (2002) 57-64 may be used to prepare branched copolymers from single monomers, including ethylene. Higher transition metal catalysts, especially nickel and palladium catalysts are also known to lead to hyper-branched polymers (the branches of which are also branched) as disclosed in Brookhart, et al., J. Am. Chem. Soc., 1995, 117, 64145-6415.

Additional complexes suitable for use include Group 4-10 derivatives corresponding to the formula:

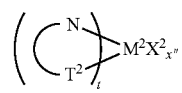

wherein $M^2$ is a metal of Groups 4-10 of the Periodic Table of the elements, preferably Group 4 metals, Ni(II) or Pd(II), most preferably zirconium;

$T^2$ is a nitrogen, oxygen or phosphorus containing group;

$X^2$ is halo, hydrocarbyl, or hydrocarbyloxy;

t is one or two;

x" is a number selected to provide charge balance;

and $T^2$ and N are linked by a bridging ligand.

Such catalysts have been previously disclosed in *J. Am. Chem. Soc.,* 118, 267-268 (1996), *J. Am. Chem. Soc.,* 117, 6414-6415 (1995), and *Organometallics,* 16, 1514-1516, (1997), among other disclosures.

Suitable examples of the foregoing metal complexes for use as catalysts are aromatic diimine or aromatic dioxyimine complexes of Group 4 metals, especially zirconium, corresponding to the formula:

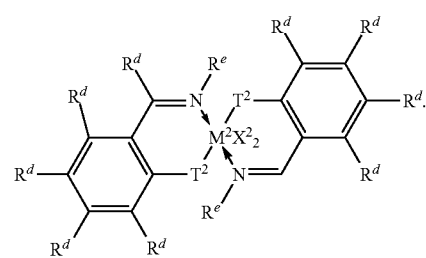

wherein

M², X² and T² are as previously defined;

$R^d$ independently in each occurrence is hydrogen, halogen, or $R^e$; and $R^e$ independently in each occurrence is C1-20 hydrocarbyl or a heteroatom-, especially a F, N, S or P-substituted derivative thereof, more preferably C1-20 hydrocarbyl or a F or N substituted derivative thereof, most preferably alkyl, dialkylaminoalkyl, pyrrolyl, piperidenyl, perfluorophenyl, cycloalkyl, (poly)alkylaryl, or aralkyl.

Suitable examples of the foregoing metal complexes for use as catalysts are aromatic dioxyimine complexes of zirconium, corresponding to the formula:

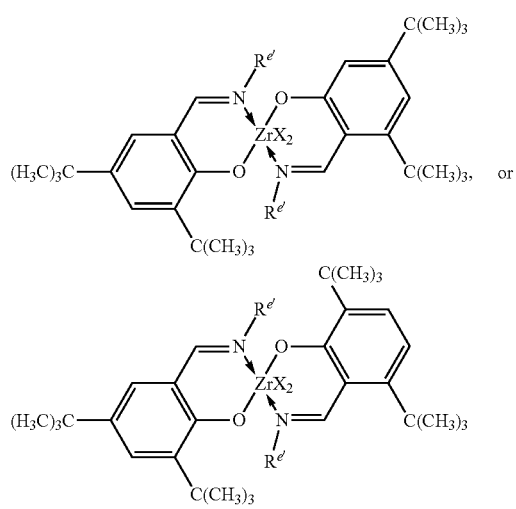

wherein;

X² is as previously defined, preferably C1-10 hydrocarbyl, most preferably methyl or benzyl; and $R^{e'}$ is methyl, isopropyl, t-butyl, cyclopentyl, cyclohexyl, 2-methylcyclohexyl, 2,4-dimethylcyclohexyl, 2-pyrrolyl, N-methyl-2-pyrrolyl, 2-piperidenyl, N-methyl-2-piperidenyl, benzyl, o-tolyl, 2,6-dimethylphenyl, perfluorophenyl, 2,6-di(isopropyl)phenyl, or 2,4,6-trimethylphenyl.

The foregoing complexes for use as also include certain phosphinimine complexes are disclosed in EP-A-890581. These complexes correspond to the formula: $[(R^f)_3—P\!=\!N]_f M(K^2)(R^f)_{3-f}$, wherein: $R^f$ is a monovalent ligand or two $R^f$ groups together are a divalent ligand, preferably $R^f$ is hydrogen or C1-4 alkyl;

M is a Group 4 metal,

K² is a group containing delocalized i-electrons through which K² is bound to M, said K² group containing up to 50 atoms not counting hydrogen atoms, and f is 1 or 2.

With reference to the above discussion of the process for preparing the composition having the formula (I) or (II), the catalyst precursor (in combination with the co-catalyst) may remain as an active catalyst in the final solution and can further function as an active catalyst in subsequent polymerization. Accordingly, the final solution of the process of the present disclosure (the final solution comprising the catalyst and the composition having the formula (I) or (II)) can be directly used for polymerization without any isolation, purification, or separation requirements and without the requirement of having a removable supported catalyst.

Exemplary, non-limiting catalyst precursors for the present disclosure include any catalyst having good chain transfer ability with organometallic compounds. Exemplary, non-limiting catalyst precursors should have no detrimental effect on subsequent polymerization and, therefore, need not be removed from the final solution prior to polymerization. Exemplary, non-limiting catalyst precursors may be good comonomer incorporating catalysts, can be used to make the compositions having the formula (I) or (II), and can also continue to remain active (in combination with co-catalyst) as active catalysts to make desired polymers in polymerization reactors, as discussed below.

Exemplary catalyst precursors that can be used in accordance with the present disclosure include but are not limited to Catalysts (A1)-(A7), as listed below.

Catalyst (A1): [N-(2,6-di(1-methylethyl)phenyl)amido)(2-isopropylphenyl)(α-naphthalen-2-diyl(6-pyridin-2-diyl)methane)]hafnium dimethyl]prepared according to the teachings of WO 03/40195 and WO 04/24740 as well as methods known in the art.

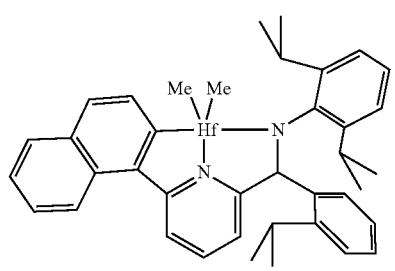

(A1)

Catalyst (A2): (E)-((2,6-diisopropylphenyl)(2-methyl-3-(octylimino)butan-2-yl)amino)trimethyl hafnium prepared according to methods known in the art.

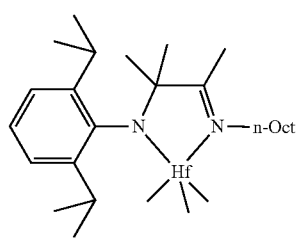

(A2)

Catalyst (A3): [[2',2'''-[1,2-cyclohexanediylbis(methyleneoxy-κO)]bis[3-(9H-carbazol-9-yl)-5-methyl[1,1'-biphenyl]-2-olato-κO]](2-)]dimethyl hafnium prepared according to methods known in the art.

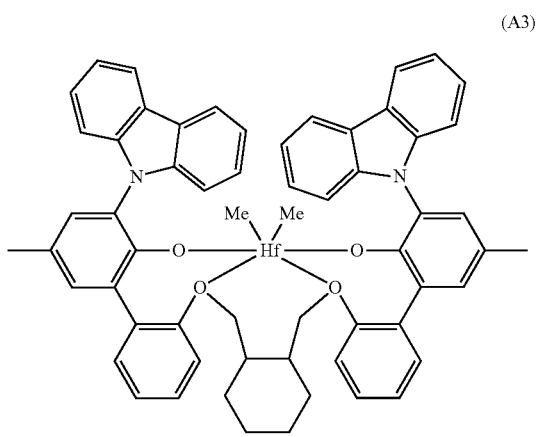

Catalyst (A4): [[2',2'''-[1,4-butanediylbis(oxy-κO)]bis[3-(9H-carbazol-9-yl)-3'-fluoro-5-methyl[1,1'-biphenyl]-2-olato-κO]](2-)]-dimethyl hafnium prepared according to methods known in the art.

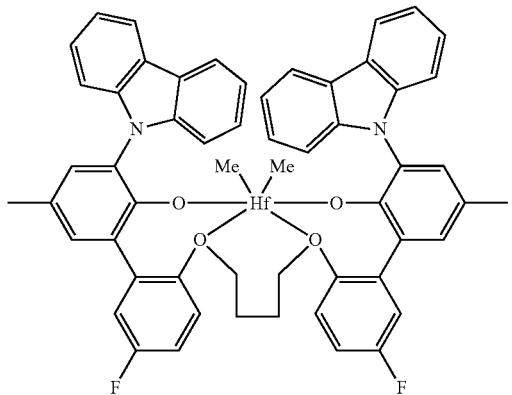

Catalyst (A5): Cyclopentadienylbis((trimethylsilyl)methyl)scandium tetrahydrofuran complex prepared according to methods known in the art.

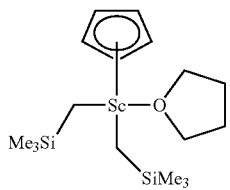

Catalyst (A6): (Mesityl(pyridin-2-ylmethyl)amino)tribenzyl hafnium prepared according to methods known in the art.

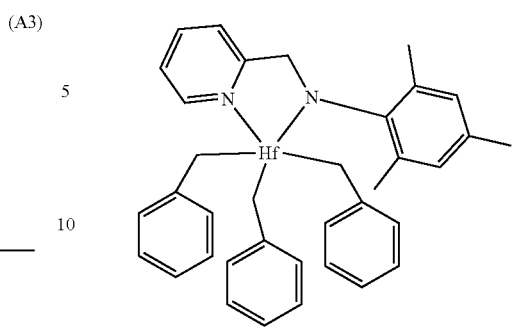

Catalyst (A7): (N-((6E)-6-(Butylimino-κN)-1-cyclohexen-1-yl)-2,6-bis(1-methylethyl)benzenaminato-κN) trimethyl-hafnium prepared according to the disclosures of WO2010/022228 as well as methods known in the art.

Co-Catalyst

Each of the catalyst precursors of the present disclosure may be activated to form an active catalyst composition by combination with a co-catalyst, preferably a cation forming co-catalyst, a strong Lewis acid, or a combination thereof. Thus, this disclosure also provides for the use of at least one co-catalyst in a catalyst composition and various methods, along with at least one catalyst precursor, and the composition having the formula (I) or (II) as disclosed herein.

The catalyst precursors desirably are rendered catalytically active by combination with a cation forming cocatalyst. Suitable cation forming co-catalysts include those previously known in the art for metal olefin polymerization complexes. Examples include neutral Lewis acids, such as $C_{1-30}$ hydrocarbyl substituted Group 13 compounds, especially tri(hydrocarbyl)aluminum- or tri(hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluoro-phenyl)borane; nonpolymeric, compatible, noncoordinating, ion forming compounds (including the use of such compounds under oxidizing conditions), especially the use of ammonium-, phosphonium-, oxonium-, carbonium-, silylium- or sulfonium-salts of compatible, noncoordinating anions, or ferrocenium-, lead- or silver salts of compatible, noncoordinating anions; and combinations of the foregoing cation forming cocatalysts and techniques. The foregoing activating co-catalysts and activating techniques have been previously taught with respect to different metal complexes for olefin polymerizations in the following references: EP-A-277,003; U.S. Pat. Nos. 5,153,157; 5,064,802; 5,321,106; 5,721,185; 5,350,723; 5,425,872; 5,625,087; 5,883,204; 5,919,983; 5,783,512; WO 99/15534, and WO99/42467.

Combinations of neutral Lewis acids, especially the combination of a trialkyl aluminum compound having from 1 to 4 carbons in each alkyl group and a halogenated tri(hydrocarbyl)boron compound having from 1 to 20 carbons in each hydrocarbyl group, especially tris(pentafluorophenyl)borane, further combinations of such neutral Lewis acid mixtures with a polymeric or oligomeric alumoxane, and combinations of a single neutral Lewis acid, especially tris (pentafluorophenyl)borane with a polymeric or oligomeric alumoxane may be used as activating cocatalysts. Exemplary molar ratios of metal complex:tris(pentafluorophenylborane:alumoxane are from 1:1:1 to 1:5:20, such as from 1:1:1.5 to 1:5:10.

Suitable ion forming compounds useful as co-catalysts in one embodiment of the present disclosure comprise a cation which is a Brønsted acid capable of donating a proton, and a compatible, noncoordinating anion, $A^-$. As used herein, the term "noncoordinating" refers to an anion or substance which either does not coordinate to the Group 4 metal containing precursor complex and the catalytic derivative derived there from, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Suitable anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitriles. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

In one aspect, suitable cocatalysts may be represented by the following general formula:

$(L^*-H)_g^+(A)^{g-}$, wherein:

L* is a neutral Lewis base;
$(L^*-H)^+$ is a conjugate Brønsted acid of L*;
$A^{g-}$ is a noncoordinating, compatible anion having a charge of g−, and g is an integer from 1 to 3.

More particularly, $A^{g-}$ corresponds to the formula: $[M'Q_4]^-$; wherein:

M' is boron or aluminum in the +3 formal oxidation state; and
Q independently in each occurrence is selected from hydride, dialkyl-amido, halide, hydrocarbyl, hydrocarbyloxide, halosubstituted-hydrocarbyl, halosubstituted hydrocarbyloxy, and halo-substituted silylhydrocarbyl radicals (including perhalogenated hydrocarbyl-perhalogenated hydrocarbyloxy- and perhalogenated silylhydrocarbyl radicals), each Q having up to 20 carbons with the proviso that in not more than one occurrence is Q halide. Examples of suitable hydrocarbyloxide Q groups are disclosed in U.S. Pat. No. 5,296,433.

In an exemplary embodiment, d is one, that is, the counter ion has a single negative charge and is $A^-$. Activating cocatalysts comprising boron which are particularly useful in the preparation of catalysts of this disclosure may be represented by the following general formula:

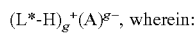
$(L^*-H)+(BQ_4)^-$; wherein:

L* is as previously defined;
B is boron in a formal oxidation state of 3; and
Q is a hydrocarbyl-, hydrocarbyloxy-, fluorinated hydrocarbyl-, fluorinated hydrocarbyloxy-, or fluorinated silylhydrocarbyl-group of up to 20 nonhydrogen atoms, with the proviso that in not more than one occasion is Q hydrocarbyl.

Especially useful Lewis base salts are ammonium salts, more preferably trialkyl-ammonium salts containing one or more $C_{12-40}$ alkyl groups. In this aspect, for example, Q in each occurrence can be a fluorinated aryl group, especially, a pentafluorophenyl group.

Illustrative, but not limiting, examples of boron compounds which may be used as an activating cocatalyst in the preparation of the improved catalysts of this disclosure include the tri-substituted ammonium salts such as:
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl)borate,
N,N-dimethylanilinium tetrakis(pentafluorophenyl)borate,
N,N-dimethylanilinium n-butyltris(pentafluorophenyl)borate,
N,N-dimethylanilinium benzyltris(pentafluorophenyl)borate,
N,N-dimethylanilinium tetrakis(4-(t-butyldimethylsilyl)-2,3,5,6 tetrafluorophenyl)borate,
N,N-dimethylanilinium tetrakis(4-(triisopropylsilyl)-2,3,5,6-tetrafluorophenyl)borate,
N,N-dimethylanilinium pentafluorophenoxytris(pentafluorophenyl)borate,
N,N-diethylanilinium tetrakis(pentafluorophenyl)borate,
N,N-dimethyl-2,4,6-trimethylanilinium tetrakis(pentafluorophenyl)borate,
dimethyloctadecylammonium tetrakis(pentafluorophenyl)borate,
methyldioctadecylammonium tetrakis(pentafluorophenyl)borate;
a number of dialkyl ammonium salts such as:
di-(i-propyl)ammonium tetrakis(pentafluorophenyl)borate,
methyloctadecylammonium tetrakis(pentafluorophenyl)borate,
methyloctadodecylammonium tetrakis(pentafluorophenyl)borate, and
dioctadecylammonium tetrakis(pentafluorophenyl)borate;
various tri-substituted phosphonium salts such as:
triphenylphosphonium tetrakis(pentafluorophenyl)borate,
methyldioctadecylphosphonium tetrakis(pentafluorophenyl)borate, and
tri(2,6-dimethylphenyl)phosphonium tetrakis(pentafluorophenyl)borate;
di-substituted oxonium salts such as:
diphenyloxonium tetrakis(pentafluorophenyl)borate,
di(o-tolyl)oxonium tetrakis(pentafluorophenyl)borate, and
di(octadecyl)oxonium tetrakis(pentafluorophenyl)borate; and di-substituted sulfonium salts such as:
di(o-tolyl)sulfonium tetrakis(pentafluorophenyl)borate, and methylcotadecylsulfonium tetrakis(pentafluorophenyl)borate.

Further to this aspect of the disclosure, examples of useful $(L^*\text{-}H)^+$ cations include, but are not limited to, methyldioctadecylammonium cations, dimethyloctadecylammonium cations, and ammonium cations derived from mixtures of trialkyl amines containing one or two $C_{14\text{-}18}$ alkyl groups.

Another suitable ion forming, activating cocatalyst comprises a salt of a cationic oxidizing agent and a noncoordinating, compatible anion represented by the formula:

$(Ox^{h+})_g(A^{g-})_h$, wherein:

$Ox^{h+}$ is a cationic oxidizing agent having a charge of h+;
h is an integer from 1 to 3; and
$A^{g-}$ and g are as previously defined.

Examples of cationic oxidizing agents include: ferrocenium, hydrocarbyl-substituted ferrocenium, $Ag^+$, or $Pb^{+2}$. Particularly useful examples of $A^{g-}$ are those anions previously defined with respect to the Bronsted acid containing activating cocatalysts, especially tetrakis(pentafluorophenyl)borate.

Another suitable ion forming, activating cocatalyst can be a compound which is a salt of a carbenium ion and a noncoordinating, compatible anion represented by the following formula:

$[C]^+A^-$ wherein:

$[C]^+$ is a $C_{1\text{-}20}$ carbenium ion; and
is a noncoordinating, compatible anion having a charge of −1. For example, one carbenium ion that works well is the trityl cation, that is triphenylmethylium.

A further suitable ion forming, activating cocatalyst comprises a compound which is a salt of a silylium ion and a noncoordinating, compatible anion represented by the formula:

$(Q^1_3Si)^+A^-$ wherein:

$Q^1$ is $C_{1\text{-}10}$ hydrocarbyl, and $A^-$ is as previously defined.

Suitable silylium salt activating cocatalysts include trimethylsilylium tetrakispentafluorophenylborate, triethylsilylium tetrakispentafluorophenylborate, and ether substituted adducts thereof. Silylium salts have been previously generically disclosed in *J. Chem. Soc. Chem. Comm.* 1993, 383-384, as well as in Lambert, J. B., et al., *Organometallics* 1994, 13, 2430-2443. The use of the above silylium salts as activating cocatalysts for addition polymerization catalysts is also described in U.S. Pat. No. 5,625,087.

Certain complexes of alcohols, mercaptans, silanols, and oximes with tris(pentafluorophenyl)borane are also effective catalyst activators and may be used according to the present disclosure. Such cocatalysts are disclosed in U.S. Pat. No. 5,296,433.

Suitable activating cocatalysts for use herein also include polymeric or oligomeric alumoxanes (also called aluminoxanes), especially methylalumoxane (MAO), triisobutyl aluminum modified methylalumoxane (MMAO), or isobutylalumoxane; Lewis acid modified alumoxanes, especially perhalogenated tri(hydrocarbyl)aluminum- or perhalogenated tri(hydrocarbyl)boron modified alumoxanes, having from 1 to 10 carbons in each hydrocarbyl or halogenated hydrocarbyl group, and most especially tris(pentafluorophenyl)borane modified alumoxanes. Such co-catalysts are previously disclosed in U.S. Pat. Nos. 6,214,760, 6,160,146, 6,140,521, and 6,696,379.

A class of co-catalysts comprising non-coordinating anions generically referred to as expanded anions, further disclosed in U.S. Pat. No. 6,395,671, may be suitably employed to activate the metal complexes of the present disclosure for olefin polymerization. Generally, these co-catalysts (illustrated by those having imidazolide, substituted imidazolide, imidazolinide, substituted imidazolinide, benzimidazolide, or substituted benzimidazolide anions) may be depicted as follows:

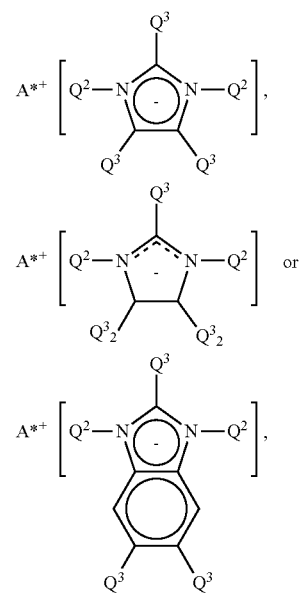

wherein:

$A^{*+}$ is a cation, especially a proton containing cation, and can be trihydrocarbyl ammonium cation containing one or two $C_{10\text{-}40}$ alkyl groups, especially a methyldi($C_{14\text{-}20}$ alkyl) ammonium cation, $Q^3$, independently in each occurrence, is hydrogen or a halo, hydrocarbyl, halocarbyl, halohydrocarbyl, silylhydrocarbyl, or silyl, (including for example mono-, di- and tri(hydrocarbyl)silyl) group of up to 30 atoms not counting hydrogen, such as $C_{1\text{-}20}$ alkyl, and $Q^2$ is tris(pentafluorophenyl)borane or tris(pentafluorophenyl)alumane).

Examples of these catalyst activators include trihydrocarbylammonium-salts, especially, methyldi($C_{i4\text{-}20}$ alkyl)ammonium-salts of:
bis(tris(pentafluorophenyl)borane)imidazolide,
bis(tris(pentafluorophenyl)borane)-2-undecylimidazolide,
bis(tris(pentafluorophenyl)borane)-2-heptadecylimidazolide,
bis(tris(pentafluorophenyl)borane)-4,5-bis(undecyl)imidazolide,
bis(tris(pentafluorophenyl)borane)-4,5-bis(heptadecyl)imidazolide,
bis(tris(pentafluorophenyl)borane)imidazolinide,
bis(tris(pentafluorophenyl)borane)-2-undecylimidazolinide,
bis(tris(pentafluorophenyl)borane)-2-heptadecylimidazolinide,
bis(tris(pentafluorophenyl)borane)-4,5-bis(undecyl)imidazolinide,
bis(tris(pentafluorophenyl)borane)-4,5-bis(heptadecyl)imidazolinide, bis(tris(pentafluorophenyl)borane)-5,6-dimethylbenzimidazolide,
bis(tris(pentafluorophenyl)borane)-5,6-bis(undecyl)benzimidazolide,
bis(tris(pentafluorophenyl) alumane)imidazolide,
bis(tris(pentafluorophenyl) alumane)-2-undecylimidazolide,
bis(tris(pentafluorophenyl) alumane)-2-heptadecylimidazolide,
bis(tris(pentafluorophenyl) alumane)-4,5-bis(undecyl)imidazolide,
bis(tris(pentafluorophenyl) alumane)-4,5-bis(heptadecyl) imidazolide,
bis(tris(pentafluorophenyl) alumane)imidazolinide,
bis(tris(pentafluorophenyl) alumane)-2-undecylimidazolinide,
bis(tris(pentafluorophenyl) alumane)-2-heptadecylimidazolinide,
bis(tris(pentafluorophenyl) alumane)-4,5-bis(undecyl)imidazolinide,
bis(tris(pentafluorophenyl) alumane)-4,5-bis(heptadecyl) imidazolinide,
bis(tris(pentafluorophenyl)alumane)-5,6-dimethylbenzimidazolide, and
bis(tris(pentafluorophenyl)alumane)-5,6-bis(undecyl)benzimidazolide.

Other activators include those described in the PCT publication WO 98/07515, such as tris(2,2',2"-nonafluorobiphenyl)fluoroaluminate. Combinations of activators are also contemplated by the disclosure, for example, alumoxanes and ionizing activators in combinations, see for example, EP-A-0 573120, PCT publications WO 94/07928 and WO 95/14044, and U.S. Pat. Nos. 5,153,157 and 5,453, 410. For example, and in general terms, WO 98/09996 describes activating catalyst compounds with perchlorates, periodates and iodates, including their hydrates. WO 99/18135 describes the use of organoboroaluminum activators. WO 03/10171 discloses catalyst activators that are adducts of Brønsted acids with Lewis acids. Other activators or methods for activating a catalyst compound are described in, for example, U.S. Pat. Nos. 5,849,852, 5,859,653, and 5,869,723, in EP-A-615981, and in PCT publication WO 98/32775. All of the foregoing catalyst activators as well as any other known activator for transition metal complex catalysts may be employed alone or in combination according to the present disclosure. In one aspect, however, the co-catalyst can be alumoxane-free. In another aspect, for example, the co-catalyst can be free of any specifically-named activator or class of activators as disclosed herein.

In a further aspect, the molar ratio of catalyst/co-catalyst employed generally ranges from 1:10,000 to 100:1, for example, from 1:5000 to 10:1, or from 1:1000 to 1:1. Alumoxane, when used by itself as an activating co-catalyst, can be employed in large quantity, generally at least 100 times the quantity of metal complex on a molar basis.

Tris(pentafluorophenyl)borane, where used as an activating co-catalyst can be employed generally in a molar ratio to the metal complex of from 0.5:1 to 10:1, such as from 1:1 to 6:1 and from 1:1 to 5:1. The remaining activating co-catalysts are generally employed in approximately equimolar quantity with the metal complex.

In exemplary embodiments of the present disclosure, the co-catalyst is [(C$_{16-18}$H$_{33-37}$)$_2$CH$_3$NH] tetrakis(pentafluorophenyl)borate salt.

Polymerization Process

The compositions of the present disclosure and catalyst systems using the compositions described herein are suitable for use in any prepolymerization and/or polymerization process over a wide range of temperatures and pressures. Such temperatures and pressures, as well as other polymerization process information, described herein can be referred to as "polymerization conditions." The temperatures may be in the range of from −60° C. to about 280° C., preferably from 50° C. to about 200° C. In another embodiment, the polymerization temperature is above 0° C., above 50° C., above 80° C., above 100° C., above 150° C. or above 200° C. In an embodiment, the pressures employed may be in the range from 1 atmosphere to about 500 atmospheres or higher. Polymerization processes include solution, gas phase, slurry phase and a high pressure process or a combination thereof.

In one embodiment, the process of the present disclosure is directed toward a solution, high pressure, slurry or gas phase polymerization process of one or more olefin monomers having from 2 to 30 carbon atoms, preferably 2 to 12 carbon atoms, and more preferably 2 to 8 carbon atoms. The present disclosure is particularly well suited to the polymerization of two or more olefin monomers of ethylene, propylene, butene-1, pentene-1, 4-methyl-pentene-1, hexene-1, octene-1 and decene-1. Other monomers useful in the process of the present disclosure include ethylenically unsaturated monomers, diolefins having 4 to 18 carbon atoms, conjugated or nonconjugated dienes, polyenes, vinyl monomers and cyclic olefins. Non-limiting monomers useful in the present disclosure may include norbornene, norbornadiene, isobutylene, isoprene, vinylbenzocyclobutane, styrenes, alkyl substituted styrene, ethylidene norbornene, dicyclopentadiene and cyclopentene. In another embodiment of the process of the present disclosure, a copolymer of ethylene is produced, where with ethylene, a comonomer having at least one alpha-olefin having from 4 to 15 carbon atoms, preferably from 4 to 12 carbon atoms, and most preferably from 4 to 8 carbon atoms, is polymerized in a solution process. In another embodiment of the process of the present disclosure, ethylene or propylene is polymerized with at least two different comonomers, optionally one of which may be a diene, to form a terpolymer.

In embodiments of the process of this present disclosure, the catalyst system may be employed in liquid phase (solution, slurry, suspension, bulk phase or combinations thereof), in high pressure liquid, or supercritical fluid or gas phase processes. Each of these processes may be employed in single, parallel or series reactors. The liquid processes comprise contacting the ethylene and/or α-olefin and at least one vicinally disubstituted olefin monomer with the catalyst system described herein in a suitable diluent or solvent and allowing the monomers to react for a sufficient time to produce embodiments of the invention copolymers. One or more of the monomers used in the polymerization may be utilized as a solvent and/or diluent, generally in homogeneous polymerizations in the liquid monomer or monomers. Hydrocarbyl solvents are also suitable, both aliphatic and aromatic, including hexane and toluene. Bulk and slurry processes may typically be accomplished by contacting the catalysts with a slurry of liquid monomer, the catalyst system being supported. Gas phase processes may use the supported catalyst and may be conducted in any manner known to be suitable for producing ethylene homopolymers or copolymers via coordination polymerization. Illustrative examples may be found in U.S. Pat. Nos. 4,543,399; 4,588,790; 5,028,670; 5,382,638; 5,352,749; 5,436,304; 5,453,471; 5,463,999; and WO 95/07942. Each is incorporated by reference for purposes of U.S. patent practice.

Generally, the polymerization reaction temperature may vary from −50° C. to 250° C. The reaction temperature conditions may be from −20° C. to 2200, or below 200° C. The pressure may vary from 1 mm Hg to 2500 bar, or from 0.1 bar to 1600 bar, or from 1.0 to 500 bar. Where lower molecular weight copolymers, e.g., $M_n$<10,000, are sought, it may be suitable to conduct the reaction processes at temperatures above 0° C. and pressures under 500 bar.

In one aspect of this disclosure, there is provided a process and the resulting polymer, the process comprising polymerizing one or more olefin monomers in the presence of an olefin polymerization catalyst and the composition having the formula (I) or (II) in a polymerization reactor or zone thereby causing the formation of at least some quantity of a polymer joined with the remnant of the composition having the formula (I) or (II). Exemplary, non-limiting polymerization processes include those known in the art, those disclosed in U.S. Pat. No. 8,501,885 B2, as well as those known in the art for producing random copolymers. Exemplary, non-limiting polymerization processes include those conducted in a single reactor or two reactors.

In yet another aspect, there is provided a process and the resulting polymer, the process comprising polymerizing one or more olefin monomers in the presence of an olefin polymerization catalyst and the composition having the formula (I) or (II) in a polymerization reactor or zone thereby causing the formation of at least some quantity of an initial polymer joined with the remnant of the composition having the formula (I) or (II) within the reactor or zone; discharging the reaction product from the first reactor or zone to a second polymerization reactor or zone operating under polymerization conditions that are distinguishable from those of the first polymerization reactor or zone; transferring at least some of the initial polymer joined with the remnant of the composition having the formula (I) or (II) to an active catalyst site in the second polymerization reactor or zone by means of at least one remaining shuttling site of the composition having the formula (I) or (II); and conducting polymerization in the second polymerization reactor or zone so as to form a second polymer segment bonded to some or all of the initial polymer by means of a remnant of the composition having the formula (I) or (II), the second polymer segment having distinguishable polymer properties from the initial polymer segment.

During the polymerization, the reaction mixture is contacted with the activated catalyst composition according to any suitable polymerization conditions. The process can be generally characterized by use of elevated temperatures and pressures. Hydrogen may be employed as a chain transfer agent for molecular weight control according to known techniques, if desired. As in other similar polymerizations, it is generally desirable that the monomers and solvents employed be of sufficiently high purity that catalyst deactivation or premature chain termination does not occur. Any suitable technique for monomer purification such as devolatilization at reduced pressure, contacting with molecular sieves or high surface area alumina, or a combination of the foregoing processes may be employed.

Supports may be employed in the present methods, especially in slurry or gas-phase polymerizations. Suitable supports include solid, particulated, high surface area, metal oxides, metalloid oxides, or mixtures thereof (interchangeably referred to herein as an inorganic oxide). Examples include, but are not limited to talc, silica, alumina, magnesia, titania, zirconia, $Sn_2O_3$, aluminosilicates, borosilicates, clays, and any combination or mixture thereof. Suitable supports preferably have a surface area as determined by nitrogen porosimetry using the B.E.T. method from 10 to 1000 $m^2/g$, and preferably from 100 to 600 $m^2/g$. The average particle size typically is from 0.1 to 500 μm, preferably from 1 to 200 μm, more preferably 10 to 100 μm.

In one aspect of the present disclosure, the catalyst composition and optional support may be spray dried or otherwise recovered in solid, particulated form to provide a composition that is readily transported and handled. Suitable methods for spray drying a liquid containing slurry are well known in the art and usefully employed herein. Preferred techniques for spray drying catalyst compositions for use herein are described in U.S. Pat. Nos. 5,648,310 and 5,672,669.

The polymerization is desirably carried out as a continuous polymerization, for example, a continuous, solution polymerization, in which catalyst components, monomers, and optionally solvent, adjuvants, scavengers, and polymerization aids are continuously supplied to one or more reactors or zones and polymer product continuously removed therefrom. Within the scope of the terms "continuous" and "continuously" as used in this context include those processes in which there are intermittent additions of reactants and removal of products at small regular or irregular intervals, so that, over time, the overall process is substantially continuous. While the composition having the formula (I) or (II) (if used) may be added at any point during the polymerization including in the first reactor or zone, at the exit or slightly before the exit of the first reactor, between the first reactor or zone and any subsequent reactor or zone, or even solely to the second reactor or zone; if present, both are typically added at the initial stages of the polymerization. If there exists any difference in monomers, temperatures, pressures or other polymerization conditions within a reactor or between two or more reactors or zones connected in series, polymer segments of differing composition such as comonomer content, crystallinity, density, tacticity, regio-regularity, or other chemical or physical differences, within the same molecule can be formed in the polymers of this disclosure. In such event, the size of each segment or block is determined by the polymer reaction conditions and typically is a most probable distribution of polymer sizes.

If multiple reactors are employed, each can be independently operated under high pressure, solution, slurry, or gas phase polymerization conditions. In a multiple zone polymerization, all zones operate under the same type of polymerization, such as solution, slurry, or gas phase, but, optionally, at different process conditions. For a solution polymerization process, it is desirable to employ homogeneous dispersions of the catalyst components in a liquid diluent in which the polymer is soluble under the polymerization conditions employed. One such process utilizing an extremely fine silica or similar dispersing agent to produce such a homogeneous catalyst dispersion wherein normally either the metal complex or the co-catalyst is only poorly soluble is disclosed in U.S. Pat. No. 5,783,512. A high pressure process is usually carried out at temperatures from 100° C. to 400° C. and at pressures above 500 bar (50 MPa). A slurry process typically uses an inert hydrocarbon diluent and temperatures of from 0° C. up to a temperature just below the temperature at which the resulting polymer becomes substantially soluble in the inert polymerization medium. For example, typical temperatures in a slurry polymerization are from 30° C., generally from 60° C. up to 115° C., including up to 100° C., depending on the polymer being prepared. Pressures typically range from atmospheric (100 kPa) to 500 psi (3.4 MPa).

In all of the foregoing processes, continuous or substantially continuous polymerization conditions generally are employed. The use of such polymerization conditions, especially continuous, solution polymerization processes, allows the use of elevated reactor temperatures which results in the economical production of the present block copolymers in high yields and efficiencies.

The catalyst may be prepared as a homogeneous composition by addition of the requisite metal complex or multiple complexes to a solvent in which the polymerization will be conducted or in a diluent compatible with the ultimate reaction mixture. The desired co-catalyst or activator and, optionally, the composition having the formula (I) or (II) may be combined with the catalyst composition either prior to, simultaneously with, or after combination of the catalyst with the monomers to be polymerized and any additional reaction diluent. Desirably, if present, the composition having the formula (I) or (II) is added at the same time.

At all times, the individual ingredients as well as any active catalyst composition are protected from oxygen, moisture, and other catalyst poisons. Therefore, the catalyst components, the composition having the formula (I) or (II), and activated catalysts are prepared and stored in an oxygen and moisture free atmosphere, generally under a dry, inert gas such as nitrogen.

Without limiting in any way the scope of the disclosure, one means for carrying out such a polymerization process is as follows. In one or more well stirred tank or loop reactors operating under solution polymerization conditions, the monomers to be polymerized are introduced continuously together with any solvent or diluent at one part of the reactor. The reactor contains a relatively homogeneous liquid phase composed substantially of monomers together with any solvent or diluent and dissolved polymer. Preferred solvents include $C_{4-10}$ hydrocarbons or mixtures thereof, especially alkanes such as hexane or mixtures of alkanes, as well as one or more of the monomers employed in the polymerization. Examples of suitable loop reactors and a variety of suitable operating conditions for use therewith, including the use of multiple loop reactors, operating in series, are found in U.S. Pat. Nos. 5,977,251, 6,319,989 and 6,683,149.

Catalyst along with co-catalyst and the composition having the formula (I) or (II) are continuously or intermittently introduced in the reactor liquid phase or any recycled portion thereof at a minimum of one location. The reactor temperature and pressure may be controlled, for example, by adjusting the solvent/monomer ratio or the catalyst addition rate, as well as by use of cooling or heating coils, jackets or both. The polymerization rate can be controlled by the rate of catalyst addition. The content of a given monomer in the polymer product is influenced by the ratio of monomers in the reactor, which is controlled by manipulating the respective feed rates of these components to the reactor. The polymer product molecular weight is controlled, optionally, by controlling other polymerization variables such as the temperature, monomer concentration, or by the composition having the formula (I) or (II), or a chain terminating agent such as hydrogen, as is known in the art.

In one aspect of the disclosure, a second reactor is connected to the discharge of a first reactor, optionally by means of a conduit or other transfer means, such that the reaction mixture prepared in the first reactor is discharged to the second reactor without substantial termination of polymer growth. Between the first and second reactors, a differential in at least one process condition may be established. Generally, for use in formation of a copolymer of two or more monomers, the difference is the presence or absence of one or more comonomers or a difference in comonomer concentration. Additional reactors, each arranged in a manner similar to the second reactor in the series may be provided as well. Further polymerization is ended by contacting the reactor effluent with a catalyst kill agent such as water, steam or an alcohol or with a coupling agent if a coupled reaction product is desired.

The resulting polymer product is recovered by flashing off volatile components of the reaction mixture such as residual monomer(s) or diluent at reduced pressure, and, if necessary, conducting further devolatilization in equipment such as a devolatilizing extruder. In a continuous process the mean residence time of the catalyst and polymer in the reactor generally is from 5 minutes to 8 hours, for example, from 10 minutes to 6 hours.

In a further aspect of this disclosure, alternatively, the foregoing polymerization may be carried out in a plug flow reactor optionally with a monomer, catalyst, the composition having the formula (I) or (II), temperature or other gradient established between differing zones or regions thereof, further optionally accompanied by separate addition of catalysts and/or the composition having the formula (I) or (II), and operating under adiabatic or non-adiabatic polymerization conditions.

In yet a further aspect, the catalyst composition may also be prepared and employed as a heterogeneous catalyst by adsorbing the requisite components on an inert inorganic or organic particulated solid, as previously disclosed. For example, a heterogeneous catalyst can be prepared by co-precipitating the metal complex and the reaction product of an inert inorganic compound and an active hydrogen containing activator, especially the reaction product of a tri($C_{1-4}$ alkyl) aluminum compound and an ammonium salt of a hydroxyaryltris(pentafluorophenyl)borate, such as an ammonium salt of (4-hydroxy-3,5-ditertiarybutylphenyl)tris (pentafluorophenyl)borate. When prepared in heterogeneous or supported form, the catalyst composition may be employed in a slurry or a gas phase polymerization. As a practical limitation, slurry polymerization takes place in liquid diluents in which the polymer product is substantially insoluble. Generally, the diluent for slurry polymerization is one or more hydrocarbons with less than 5 carbon atoms. If desired, saturated hydrocarbons such as ethane, propane, or butane may be used in whole or part as the diluent. As with a solution polymerization, the α-olefin comonomer or a combination of different α-olefin monomers may be used in whole or part as the diluent. Most preferably at least a major part of the diluent comprises the α-olefin monomer or monomers to be polymerized.

In this aspect, for use in gas phase polymerization processes, the support material and resulting catalyst typically can have a median particle diameter from 20 to 200 µm, generally from 30 µm to 150 µm, and typically from 50 µm to 100 µm. For use in slurry polymerization processes, the support can have a median particle diameter from 1 µm to 200 µm, generally from 5 µm to 100 µm, and typically from 10 µm to 80 µm.

Suitable gas phase polymerization process for use herein are substantially similar to known processes used commercially on a large scale for the manufacture of polypropylene, ethylene/α-olefin copolymers, and other olefin polymers. The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported or suspended above a perforated plate or fluidization grid, by a flow of fluidization gas. Suitable gas phase processes which are adaptable for use in the process of this disclosure are disclosed in, for example, U.S. Pat. Nos. 4,588,790; 4,543,399; 5,352,749; 5,436,304; 5,405,922; 5,462,999; 5,461,123; 5,453,471; 5,032,562; 5,028,670; 5,473,028; 5,106,804; 5,556,238; 5,541,270; 5,608,019; and 5,616,661.

The use of functionalized derivatives of polymers are also included within the present disclosure. Examples include metallated polymers wherein the metal is the remnant of the catalyst or the composition having the formula (I) or (II) employed, as well as further derivatives thereof. Because a substantial fraction of the polymeric product exiting the reactor is terminated with the composition having the formula (I) or (II), further functionalization is relatively easy. The metallated polymer species can be utilized in well known chemical reactions such as those suitable for other alkyl-aluminum, alkyl-gallium, alkyl-zinc, or alkyl-Group 1 compounds to form amine-, hydroxy-, epoxy-, silane, vinylic, and other functionalized terminated polymer products. Examples of suitable reaction techniques that are adaptable for use herein are described in Negishi, "Organometallics in Organic Synthesis", Vol. 1 and 2, (1980), and other standard texts in organometallic and organic synthesis.

Olefin Monomers

Suitable monomers for use in preparing the polymer products of the present disclosure in polymerization processes include any addition polymerizable monomer, generally any olefin or diolefin monomer. Suitable monomers can be linear, branched, acyclic, cyclic, substituted, or unsubstituted. In one aspect, the olefin can be any α-olefin, including, for example, ethylene and at least one different copolymerizable comonomer, propylene and at least one different copolymerizable comonomer having from 4 to 20 carbons, or 4-methyl-1-pentene and at least one different copolymerizable comonomer having from 4 to 20 carbons. Examples of suitable monomers include, but are not limited to, straight-chain or branched α-olefins having from 2 to 30 carbon atoms, from 2 to 20 carbon atoms, or from 2 to 12 carbon atoms. Specific examples of suitable monomers include, but are not limited to, ethylene, propylene, 1-butene, 1-pentene, 3-methyl-1-butene, 1-hexane, 4-methyl-1-pentene, 3-methyl-1-pentene, 1-octene, 1-decene, 1-dodecene, 1-tetradecene, 1-hexadecene, 1-octadecene, and 1-eicosene. Suitable monomers for use in preparing the copolymers disclosed herein also include cycloolefins having from 3 to 30, from 3 to 20 carbon atoms, or from 3 to 12 carbon atoms. Examples of cycloolefins that can be used include, but are not limited to, cyclopentene, cycloheptene, norbornene, 5-methyl-2-norbornene, tetracyclododecene, and 2-methyl-1,4,5,8-dimethano-1,2,3,4,4a,5,8,8a-octahydronaphthalene. Suitable monomers for preparing the copolymers disclosed herein also include di- and poly-olefins having from 3 to 30, from 3 to 20 carbon atoms, or from 3 to 12 carbon atoms. Examples of di- and poly-olefins that can be used include, but are not limited to, butadiene, isoprene, 4-methyl-1,3-pentadiene, 1,3-pentadiene, 1,4-pentadiene, 1,5-hexadiene, 1,4-hexadiene, 1,3-hexadiene, 1,3-octadiene, 1,4-octadiene, 1,5-octadiene, 1,6-octadiene, 1,7-octadiene, ethylidene norbornene, vinyl norbornene, dicyclopentadiene, 7-methyl-1,6-octadiene, 4-ethylidene-8-methyl-1,7-nonadiene, and 5,9-dimethyl-1,4,8-decatriene. In a further aspect, aromatic vinyl compounds also constitute suitable monomers for preparing the copolymers disclosed here, examples of which include, but are not limited to, mono- or poly-alkylstyrenes (including styrene, o-methylstyrene, m-methylstyrene, p-methylstyrene, o,p-dimethylstyrene, o-ethylstyrene, m-ethylstyrene and p-ethylstyrene), and functional group-containing derivatives, such as methoxystyrene, ethoxystyrene, vinylbenzoic acid, methyl vinylbenzoate, vinylbenzyl acetate, hydroxystyrene, o-chlorostyrene, p-chlorostyrene, divinylbenzene, 3-phenylpropene, 4-phenylpropene and a-methylstyrene, vinylchloride, 1,2-difluoroethylene, 1,2-dichloroethylene, tetrafluoroethylene, and 3,3,3-trifluoro-1-propene, provided the monomer is polymerizable under the conditions employed.

Further, in one aspect, suitable monomers or mixtures of monomers for use in combination with the composition having the formula (I) or (II) disclosed here include ethylene; propylene; mixtures of ethylene with one or more monomers selected from propylene, 1-butene, 1-hexene, 4-methyl-1-pentene, 1-octene, and styrene; and mixtures of ethylene, propylene and a conjugated or non-conjugated diene. In this aspect, the copolymer or interpolymer can contain two or more intramolecular regions comprising differing chemical or physical properties, especially regions of differentiated comonomer incorporation, joined in a dimeric, linear, branched or polybranched polymer structure. Such polymers may be prepared by altering the polymerization conditions during a polymerization that includes a composition having the formula (I) or (II), for example by using two reactors with differing comonomer ratios, multiple catalysts with differing comonomer incorporation abilities, or a combination of such process conditions, and optionally a polyfunctional coupling agent.

Polymer Products

As disclosed herein, the polymer products refer to polymer products, after polymerization, that are typically subjected to chemical treatment to consume reactive metal alkyl groups and liberate the polymer products from attachment to transition group or main group metals. This process comprises hydrolysis with water to generate saturated polymer end groups. Alternatively, addition of various organic or inorganic reagents may be added to both consume the metal alkyl groups and generate reactive functional end groups on the polymer chains.

The polymers produced by the processes of the present disclosure can be used in a wide variety of products and end-use applications. The polymers produced can be homo- and co-polymers of ethylene and propylene and include linear low density polyethylene, elastomers, plastomers, high-density polyethylenes, medium density polyethylenes, low density polyethylenes, polypropylene, and polypropylene copolymers. Propylene based polymers produced include isotactic polypropylene, atactic polypropylene, and random, block or impact copolymers.

Utilizing the polymerization processes disclosed here, novel polymer compositions, including block copolymers of one or more olefin monomers having the present molecular weight distribution, are readily prepared. Exemplary polymers comprise in polymerized form at least one monomer selected from ethylene, propylene, and 4-methyl-1-pentene. Illustratively, the polymers are interpolymers comprising in polymerized form ethylene, propylene, or 4-methyl-1-pentene and at least one different $C_{2-20}$ α-olefin comonomer, and optionally one or more additional copolymerizable comonomers. Suitable comonomers are selected from diolefins, cyclic olefins, and cyclic diolefins, halogenated vinyl compounds, vinylidene aromatic compounds, and combinations thereof. Exemplary polymers are interpolymers of ethylene with propylene, 1-butene, 1-hexene or 1-octene. Illustratively, the polymer compositions disclosed here have an ethylene content from 1 to 99 percent, a diene content from 0 to 10 percent, and a styrene and/or $C_{3-8}$ α-olefin content from 99 to 1 percent, based on the total weight of the polymer. The polymers of the present disclosure may have a weight average molecular weight (Mw) from 10,000 to 2,500,000. Typically, the polymers of the present disclosure have a weight average molecular weight (Mw) from 500 to 250,000 (e.g., from 2,000 to 150,000, from 3,000 to 100,000, from 1,000 to 25,000, from 5,000 to 25,000, etc.).

The polymers prepared according to this disclosure can have a melt index, $I_2$, from 0.01 to 2000 g/10 minutes, typically from 0.01 to 1000 g/10 minutes, more typically from 0.01 to 500 g/10 minutes, and especially from 0.01 to 100 g/10 minutes. Desirably, the disclosed polymers can have molecular weights, $M_w$, from 1,000 g/mole to 5,000,000 g/mole, typically from 1000 g/mole to 1,000,000, more typically from 1000 g/mole to 500,000 g/mole, and especially from 1,000 g/mole to 300,000 g/mole.

The density of the polymers of this disclosure can be from 0.80 to 0.99 $g/cm^3$ and typically, for ethylene containing polymers, from 0.85 $g/cm^3$ to 0.97 $g/cm^3$ (e.g., from 0.853 to 0.970 $g/cm^3$).

The polymers according to this disclosure may be differentiated from conventional, random copolymers, physical blends of polymers, and block copolymers prepared via sequential monomer addition, fluxional catalysts, or by anionic or cationic living polymerization techniques, by, among other things, their narrow molecular weight distributions. In this aspect, for example, the polymer composition prepared according to this disclosure can be characterized by a polydispersity index (PDI) of from 1.5 to 10.0 (e.g, from 2.0 to 8.0, from 2.0 to 6.0, from 2.0 to 5.0, from 2.0 to 4.0, etc.). For example, the polydispersity index (PDI) of the polymer composition can be from 1.5 to 2.8, from 1.5 to 2.5, or from 1.5 to 2.3.

If present, the separate regions or blocks within each polymer are relatively uniform, depending on the uniformity of reactor conditions, and chemically distinct from each other. That is, the comonomer distribution, tacticity, or other property of segments within the polymer are relatively uniform within the same block or segment. However, the average block length can be a narrow distribution, but is not necessarily so. The average block length can also be a most probable distribution.

Illustratively, these interpolymers can be characterized by terminal blocks or segments of polymer having higher tacticity or crystallinity from at least some remaining blocks or segments. Illustratively, the polymer can be a triblock copolymer containing a central polymer block or segment that is relatively amorphous or even elastomeric.

In a still further aspect of this disclosure, there is provided a polymer composition comprising: (1) an organic or inorganic polymer, preferably a homopolymer of ethylene or of propylene and/or a copolymer of ethylene or propylene with one or more copolymerizable comonomers, and (2) a polymer or combination of polymers according to the present disclosure or prepared according to the process disclosed here.

The inventive polymer products include combinations of two or more polymers comprising regions or segments (blocks) of differing chemical composition. In addition, at least one of the constituents of the polymer combination can contain a linking group which is the remnant of the composition having the formula (I) or (II), causing the polymer to possess certain physical properties.

Various additives may be usefully incorporated into the present compositions in amounts that do not detract from the properties of the resultant composition. These additives include, for example, reinforcing agents, fillers including conductive and non-conductive materials, ignition resistant additives, antioxidants, heat and light stabilizers, colorants, extenders, crosslinkers, blowing agents, plasticizers, flame retardants, anti-drip agents, lubricants, slip additives, anti-blocking aids, anti-degradants, softeners, waxes, pigments, and the like, including combinations thereof.

The resultant polymers may be block interpolymers that can be characterized by an average block index, e.g., as discussed in U.S. Pat. Nos. 7,947,793, 7,897,698, and 8,293,859. The resultant polymers may be block composites that can be characterized by a block composite index, e.g., as discussed in U.S. Pat. Nos. 8,563,658, 8,476,366, 8,686,087, and 8,716,400. The resultant polymers may be crystalline block composites that can be characterized by a crystalline block composite index, e.g., as discussed in U.S. Pat. Nos. 8,785,554, 8,822,598, and 8,822,599. The resultant polymers may be specified block composites that can be characterized by a microstructure index, e.g., as discussed in WO 2016/028957. The resultant polymers may be specified block composites that can be characterized by a modified block composite index, e.g., as discussed in WO 2016/028970.

In certain embodiments, the process for preparing the composition having the formula (I) or (II) may be combined with functionalization chemistry to develop telechelic olefin prepolymers or polymers. In certain embodiments, the composition having the formula (I) or (II) can generate and grow telechelic polymer chains with both ends bonded to the composition having the formula (I) or (II); subsequent transformation of the terminal polymeryl-metal bonds to desired di-end-functional groups may then occur to form the telechelic polymer.

Applications of the combination of the process for preparing the composition having the formula (I) or (II) of the present disclosure with functionalization chemistry are in no way limited to development of telechelic olefin prepolymers or polymers and the above example. In certain embodiments, the process for preparing the composition having the formula (I) or (II) of the present disclosure may be combined with, e.g., coordinative chain transfer polymerization, to produce functionalized polyolefins.

The polymers of the present disclosure may be blended and/or coextruded with any other polymer. Non-limiting examples of other polymers include linear low density polyethylenes, elastomers, plastomers, high pressure low density polyethylene, high density polyethylenes, isotactic polypropylene, ethylene propylene copolymers and the like.

Polymers produced by the process of the present disclosure and blends thereof are useful in such forming operations as film, sheet, and fiber extrusion and coextrusion as well as blow molding, injection molding, roto-molding. Films include blown or cast films formed by coextrusion or by lamination useful as shrink film, cling film, stretch film, sealing film or oriented films.

EXAMPLES

Methodologies $^1$H NMR:

$^1$H NMR spectra are recorded on a Bruker AV-400 spectrometer at ambient temperature. $^1$H NMR chemical shifts in benzene-$d_6$ are referenced to 7.16 ppm ($C_6D_5H$) relative to TMS (0.00 ppm).

$^{13}$C NMR:

$^{13}$C NMR spectra of polymers are collected using a Bruker 400 MHz spectrometer equipped with a Bruker Dual DUL high-temperature CryoProbe. The polymer samples are prepared by adding approximately 2.6 g of a 50/50 mixture of tetrachloroethane-$d_2$/orthodichlorobenzene containing 0.025M chromium trisacetylacetonate (relaxation agent) to 0.2 g of polymer in a 10 mm NMR tube. The samples are dissolved and homogenized by heating the tube and its contents to 150° C. The data is acquired using 320 scans per data file, with a 7.3 second pulse repetition delay with a sample temperature of 120° C.

GCMS:

Tandem gas chromatography/low resolution mass spectroscopy using electron impact ionization (EI) is performed at 70 eV on an Agilent Technologies 6890N series gas chromatograph equipped with an Agilent Technologies 5975 inert XL mass selective detector and an Agilent Technologies Capillary column (HP1MS, 15 m×0.25 mm, 0.25 micron) with respect to the following:

Programmed Method:
Oven Equilibration Time 0.5 min
50° C. for 0 min
then 25° C./min to 200° C. for 5 min
Run Time 11 min DSC Standard Method:

Differential Scanning Calorimetry results are determined using a TAI model Q1OOO DSC equipped with an RCS cooling accessory and an autosampler. A nitrogen purge gas flow of 50 ml/min is used. The sample is pressed into a thin film and melted in the press at 175° C. and then air-cooled to room temperature (25° C.). About 10 mg of material in the form of a 5-6 mm diameter disk is accurately weighed and placed in an aluminum foil pan (ca 50 mg) which is then crimped shut. The thermal behavior of the sample is investigated with the following temperature profile. The sample is rapidly heated to 180° C. and held isothermal for 3 minutes in order to remove any previous thermal history. The sample is then cooled to −40° C. at 10° C./min cooling rate and held at −40° C. for 3 minutes. The sample is then heated to 150° C. at 10° C./min heating rate. The cooling and second heating curves are recorded.

The DSC melting peak is measured as the maximum in heat flow rate (W/g) with respect to the linear baseline drawn between −30° C. and end of melting. The heat of fusion is measured as the area under the melting curve between −30° C. and the end of melting using a linear baseline.

Molecular Weight Determination:

Molecular weights are determined by optical analysis techniques including deconvoluted gel permeation chromatography coupled with a low angle laser light scattering detector (GPC-LALLS) as described by Rudin, A., "Modern Methods of Polymer Characterization", John Wiley & Sons, New York (1991) pp. 103-112.

GPC Method:

The gel permeation chromatographic system consists of either a Polymer Laboratories Model PL-210 or a Polymer Laboratories Model PL-220 instrument. The column and carousel compartments are operated at 140° C. Three Polymer Laboratories 10-micron Mixed-B columns are used. The solvent is 1,2,4 trichlorobenzene. The samples are prepared at a concentration of 0.1 grams of polymer in 50 milliliters of solvent containing 200 ppm of butylated hydroxytoluene (BHT). Samples are prepared by agitating lightly for 2 hours at 160° C. The injection volume used is 100 microliters and the flow rate is 1.0 ml/minute.

Calibration of the GPC column set is performed with 21 narrow molecular weight distribution polystyrene standards with molecular weights ranging from 580 to 8,400,000, arranged in 6 "cocktail" mixtures with at least a decade of separation between individual molecular weights. The standards are purchased from Polymer Laboratories (Shropshire, UK). The polystyrene standards are prepared at 0.025 grams in 50 milliliters of solvent for molecular weights equal to or greater than 1,000,000 and 0.05 grams in 50 milliliters of solvent for molecular weights less than 1,000,000. The polystyrene standards are dissolved at 80° C. with gentle agitation for 30 minutes. The narrow standards mixtures are run first and in order of decreasing highest molecular weight component to minimize degradation. The polystyrene standard peak molecular weights are converted to polyethylene molecular weights using the following equation (as described in Williams and Ward, J. Polym. ScL, Polym. Let., 6, 621 (1968)):

$M_{polyethylene}$=0.431($M_{polystyrene}$). Polyethylene equivalent molecular weight calculations are performed using Viscotek TriSEC software Version 3.0.

Density:

Density measurements are conducted according to ASTM D792.

Materials

The following materials are principally used in the examples of the present disclosure.

Anhydrous toluene is obtained from Sigma-Aldrich and is further dried over alumina, which is activated in a 275° C. oven for about 5 hours. 1,2,4-trivinylcyclohexane ("TVCH") is obtained from Sigma-Aldrich and is dried over activated alumina before use. Diethylzinc ("DEZ" or "ZnEt2") and triethylaluminum ("TEA" or "AlEt3") are obtained from Sigma-Aldrich. [($C_{16-18}H_{33-37}$)$_2$$CH_3NH$] tetrakis(pentafluorophenyl)borate salt ("Co-catalyst A") is obtained from Boulder Scientific Co. Isopar™ E is obtained from Exxon.

(E)-((2,6-diisopropylphenyl)(2-methyl-3-(octylimino)butan-2-yl)amino)trimethyl hafnium ("Catalyst (A2)") is obtained from Boulder Scientific Co. and prepared according to methods known in the art. The structure of Catalyst (A2) is illustrated below:

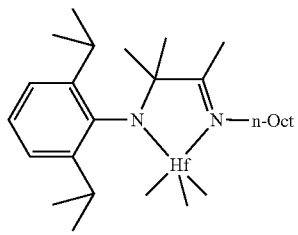

The following examples are provided as further illustrations of the present disclosure and are not to be construed as limiting. The term "overnight", if used, refers to a time of approximately 16-18 hours, and the term "room temperature" refers to a temperature of 20-25° C. In the event the name of a compound herein does not conform to the structural representation thereof, the structural representation shall control. The synthesis of all metal complexes and the preparation of all screening experiments are carried out in a dry nitrogen atmosphere using dry box (glove box) techniques, including running reactions entirely within a dry box under a nitrogen atmosphere. All solvents used are HPLC grade and are dried before their use.

Working Example 1

In a drybox under an atmosphere of nitrogen, TVCH (0.327 ml, 1.68 mmol), DEZ (0.2 ml, 1.94 mmol) and Co-catalyst A (0.06 mmol in 1 ml methylcyclohexane) are added to 7 ml of toluene in a 2 oz glass vial equipped with a stir-bar. A sample is taken for $^1$H NMR in C6D6, as seen in the "before reaction" spectrum in FIG. 1. Catalyst (A2) (19 mg in 2 ml toluene, 0.032 mmol) is added to initiate the reaction and to form a final solution containing the composition of Working Example 1. The final solution is stirred at room temperature overnight and has a [Zn] of 0.22 M.

A sample of the final solution is diluted in benzene-d6 for "after overnight reaction" $^1$H NMR analysis as seen in FIG. 1. As seen in FIG. 1, only trace amounts of vinyl unsaturation are left in the "after overnight reaction" spectrum, indicating that the vinyl groups of TVCH are consumed after overnight reaction. Concurrently, the ZnEt peak is also diminished, but a small amount remains as seen on the $^1$H NMR spectra. Accordingly, $^1$H NMR analysis provides proof of the coordination and insertion of TVCH into the transition metal catalyst precursor followed by chain transfer to zinc.

Figure 3A:
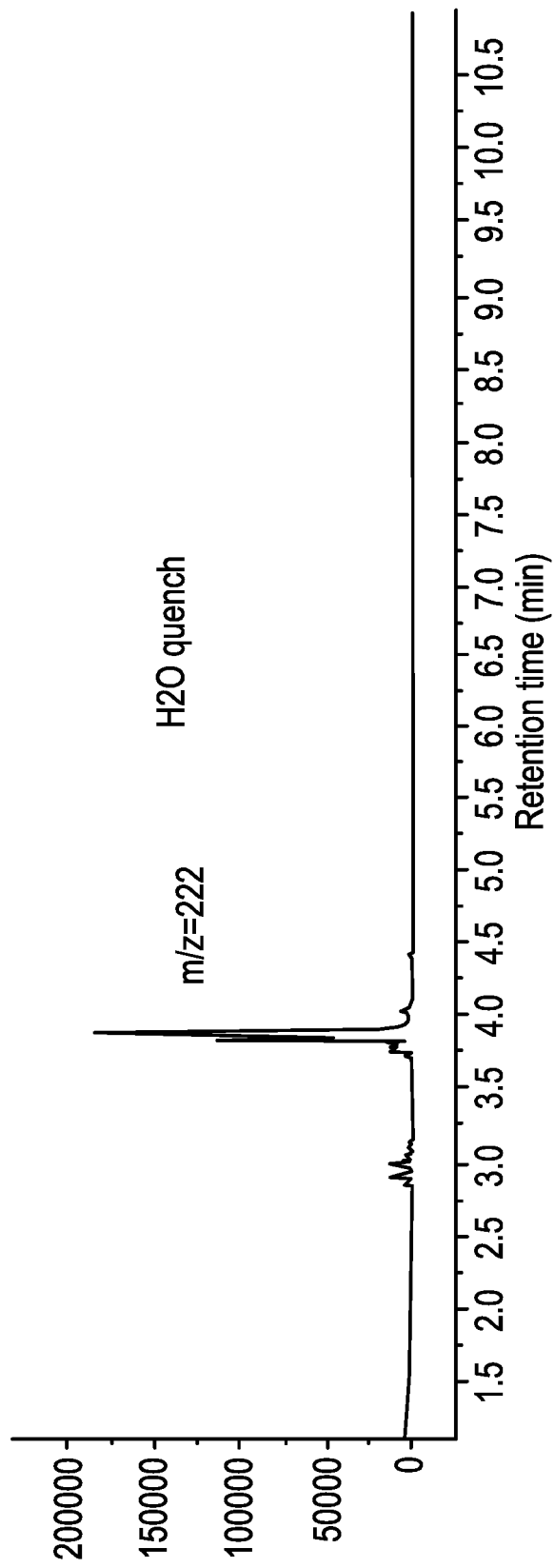
FIGS. 3A and 3B provide the GCMS of the composition of Working Example 1.
Figure 3B:
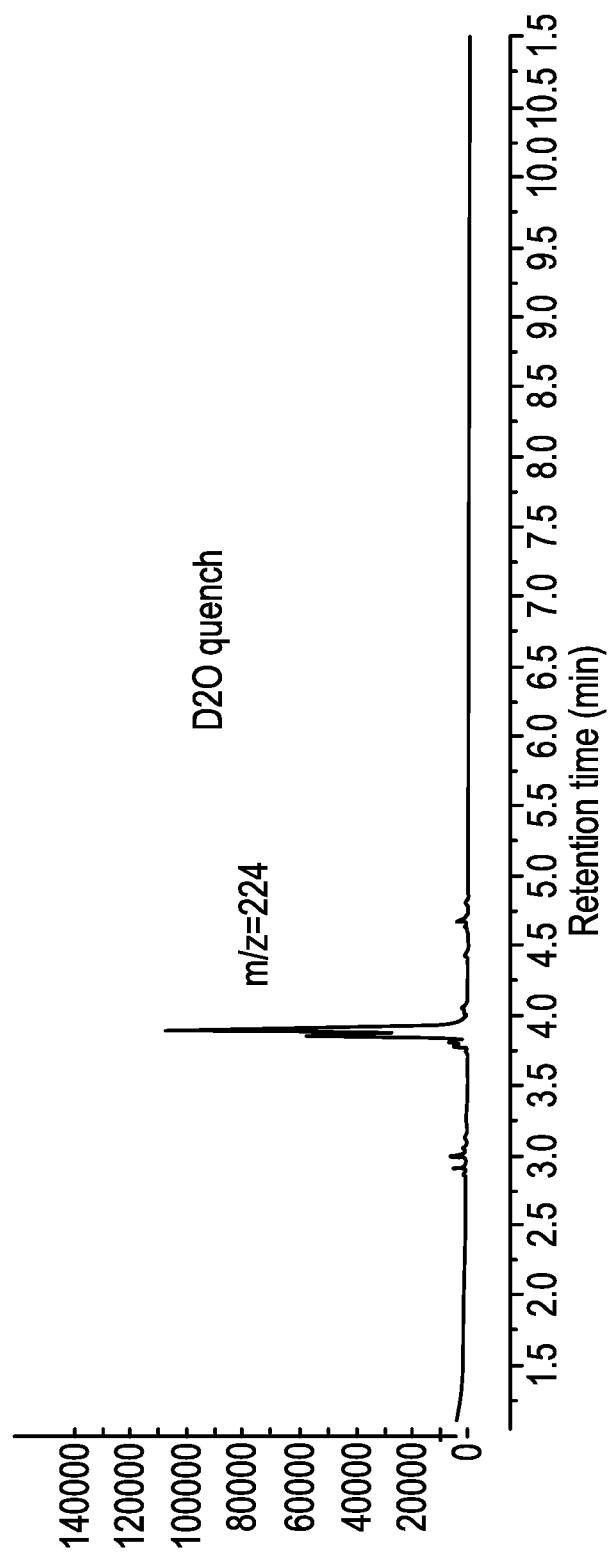

Further samples of the final solution are also analyzed via GCMS. More specifically, as seen in FIGS. 3A and 3B, aliquots of the final solution are quenched by water and deuterium oxide separately. As seen in FIGS. 3A and 3B, the water quenched sample shows major peaks at m/z of about 222, while the D2O quenched sample shows major peaks at m/z of about 224; these peaks are consistent with the expected hydrolyzed products shown below in exemplary, non-limiting Scheme 2. The multiplicity of peaks is believed to be the result of multiple chiral centers in the structure.

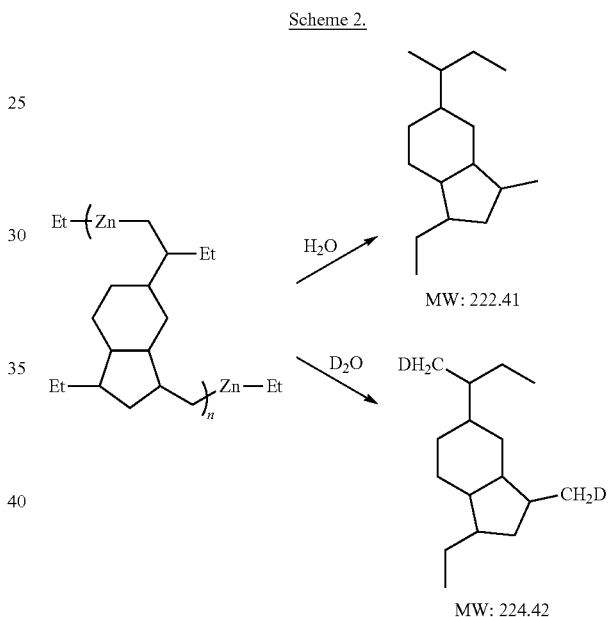

Scheme 2.

Furthermore, GCMS analysis shows the surprising and unexpected nature of the present disclosure. It was expected that TVCH might form a three-headed organometallic species since TVCH has three vinyl groups; such a three-headed organometallic species would generate a hydrolyzed product with a molecular weight of about 252, as illustrated below in exemplary, non-limiting Scheme 3. Surprisingly, GCMS does not detect peaks at m/z of about 252. Instead, it unexpectedly shows groups of peaks at m/z of about 222, which is consistent with the double-ring structures formed by intramolecular insertion of two neighboring vinyl groups. Accordingly, an exemplary mechanism is insertion of the first vinyl group on the transition metal followed by the consecutive insertion of the neighboring vinyl in 2,1-fashion to form a 6/6 ring structure or in 1,2-fashion to form a 6/5 ring structure as shown in exemplary, non-limiting Scheme 1. The minor peaks at m/z of about 192 are presumably half reacted TVCH with only one vinyl group inserted.

Scheme 3.

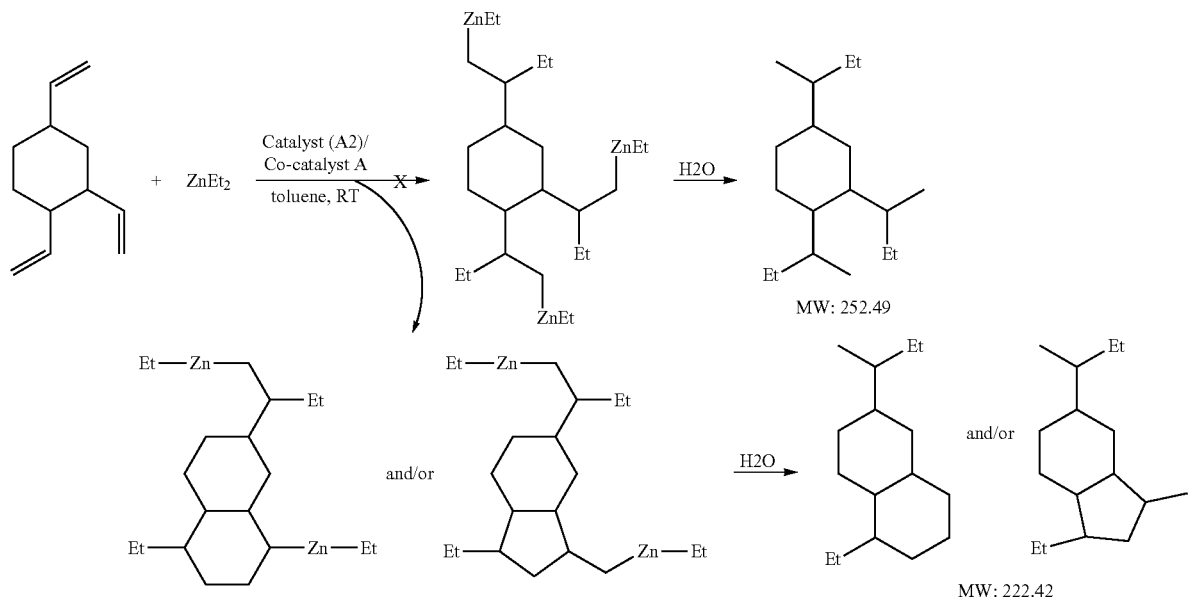

The D2O quenched sample confirms the dual-headed nature of the organometallic species. As anticipated, the 222 peaks on the GCMS shift to about 224 for the D2O quenched sample, indicating that the alkane moiety is attached to two zinc atoms before hydrolysis.

To further probe the structure, a further sample of the final solution is hydrolyzed with deuterium oxide, and $^{13}$C NMR analysis is performed on the isolated hydrolyzed product, as seen in FIG. 2. As seen in FIG. 2, $^{13}$C NMR analysis shows that the isolated hydrolyzed product is consistent with the structure shown in exemplary, non-limiting Scheme 2. Specifically, as seen in FIG. 2, the deuterium labelled carbons shift slightly up-field and split into three peaks and are, thus, easily distinguished from the unlabeled carbons. As indicated in exemplary, non-limiting Scheme 4, the 6/6 ring structure would have one labelled primary carbon and one labelled secondary carbon (CH2D:CHD=1), and the 6/5 ring structure would have two labelled primary carbons with different chemical shift (CH2D(1): CH2D(2)=1). If the product is a mixture of the two, we would get CH2D(1): [CH2D(2)+CHD]=1. As shown by the $^{13}$C NMR spectra in FIG. 2, no CHD (D on secondary carbon) is detected; there are two CH2D peaks with similar intensity. The result indicates that the product has a 6/5 ring structure. It is noted that the D-labelling is not complete, possibly due to residual water in the D2O reagent.

Scheme 4.

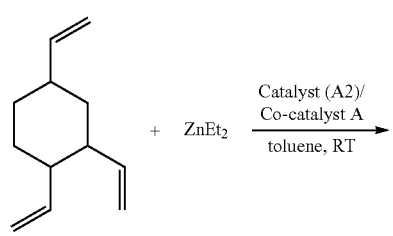

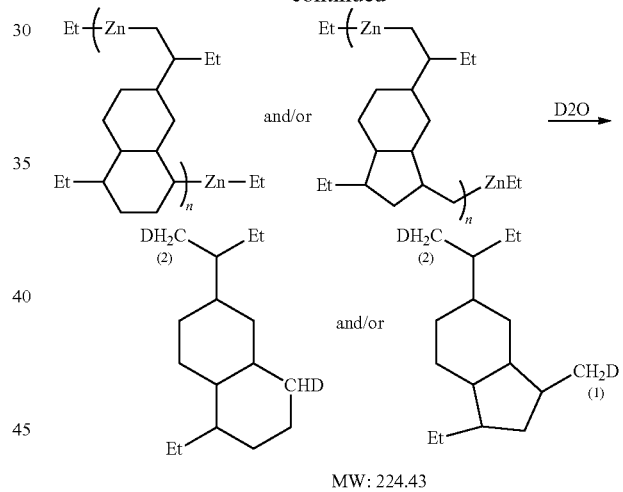

Ethylene Polymerization with the Composition of Working Example 1

To validate the dual-headed composition of Working Example 1, ethylene polymerization is performed using the composition in a polymerization setup.

ISOPAR™ E (10 ml), MMAO-3A (0.03 mmol) and Co-catalyst A (0.0013 mmol) are added to a 40 ml glass vial equipped with a stirbar in the drybox. The vial is capped with a septum lined lid and connected to an ethylene line via a needle. Another needle is inserted on the lid to let ethylene slowly purge the vial for 2 min. The vial is placed in a heating block at 100° C. The final solution of Working Example 1 (2 ml, 0.4 mmol) and Catalyst (A2) (0.001 mmol) are injected, and the purge needle is removed to maintain a total pressure at 12 psig. The reaction is maintained for 30 min. After polymerization, 0.5 ml of deuterated isopropyl alcohol (iPrOD) is added to quench the reaction. The mixture is moved out of the drybox and poured into a large amount of MeOH. The precipitated polymer is filtered, dried under vacuum at RT overnight then at 70° C. for 3 hr. 0.5 g of white polyethylene is obtained. Such a procedure is cursorily illustrated below in exemplary, non-limiting Scheme 5.

consistent to the expected hydrolyzed product (i.e., the derivative of a TVCH linking group).

Accordingly, analysis of $^1$H NMR and GCMS shows that the synthesis reaction proceeded as intended. The process for preparing the composition of Working Example 2 is illustrated below in exemplary, non-limiting Scheme 6.

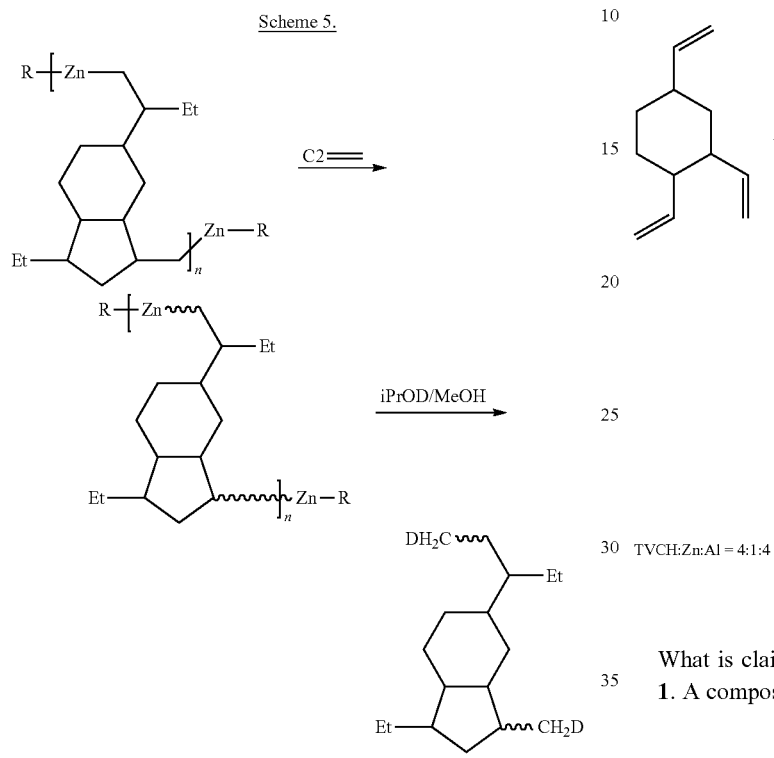

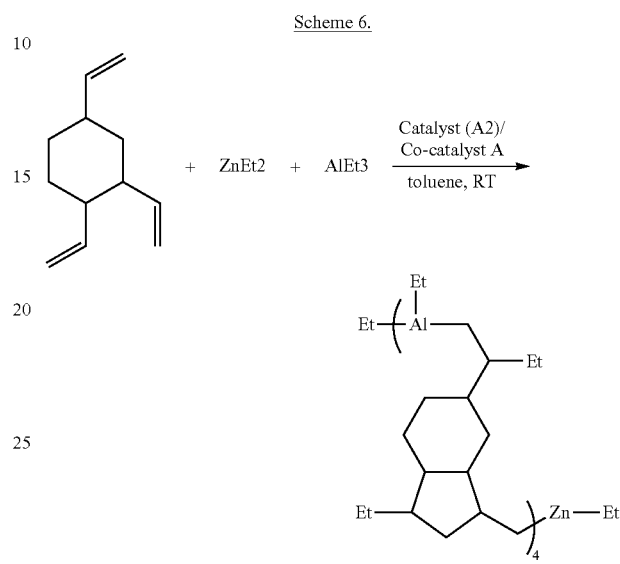

TVCH:Zn:Al = 4:1:4

Figure 4:
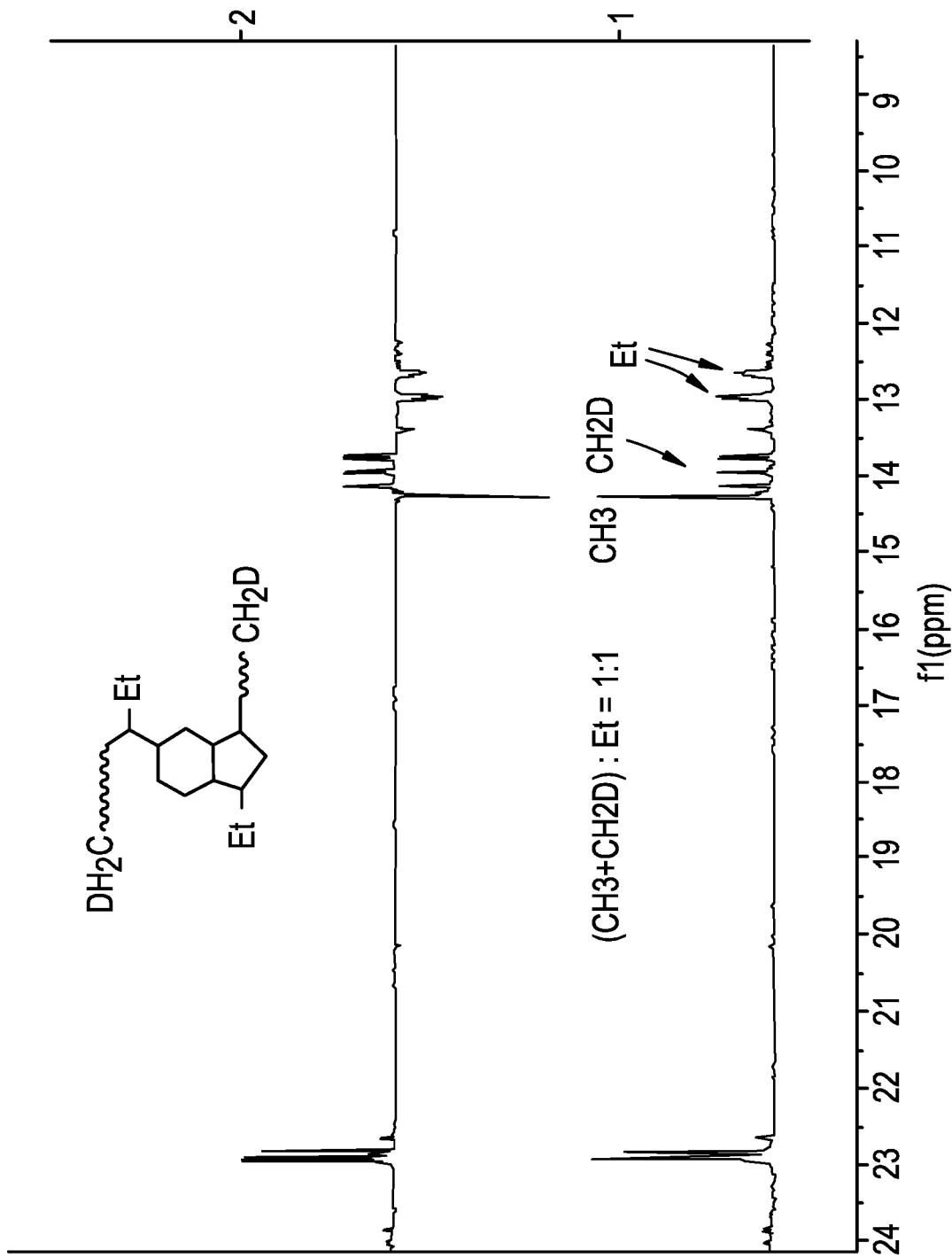
FIG. 4 provides the $^{13}$C NMR spectra of deuterium labeled polyethylene polymerized in the presence of the composition of Working Example 1.

As seen in FIG. 4, $^{13}$C NMR analysis of the polymer shows the ethyl groups from the composition fragment as well as the labeled and some unlabeled chain ends due to incomplete quenching. The result validates the effective transfer of polymer chains to the composition and chain growth in a dual headed fashion. The result also validates the one-pot nature of the process of the present disclosure. The final solution of Working Example 1 is used directly in polymerization without any isolation, separation, or purification requirements.

Working Example 2

Figure 5:
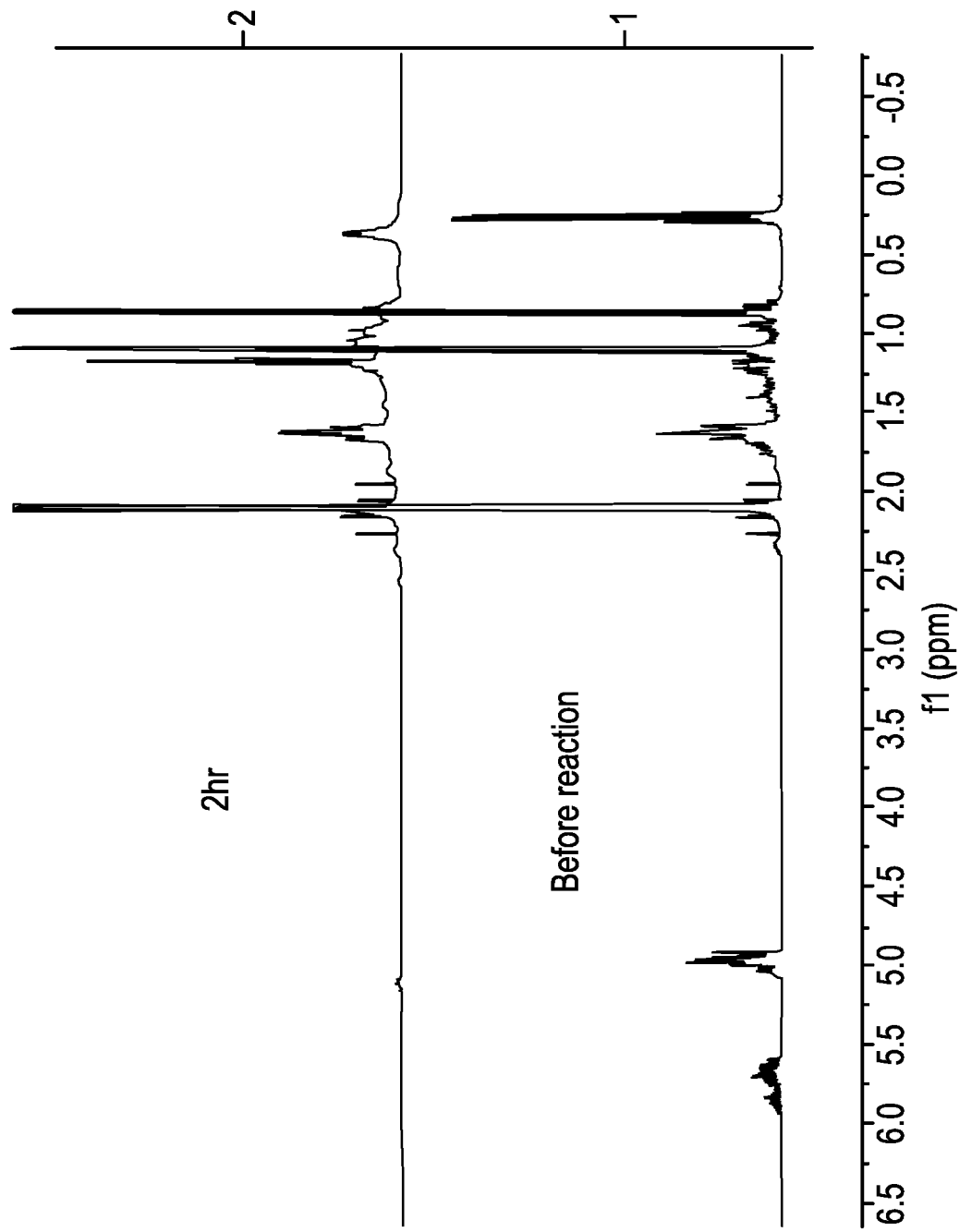
FIG. 5 provides the $^1$H NMR spectra of the composition of Working Example 2.
Figure 6:
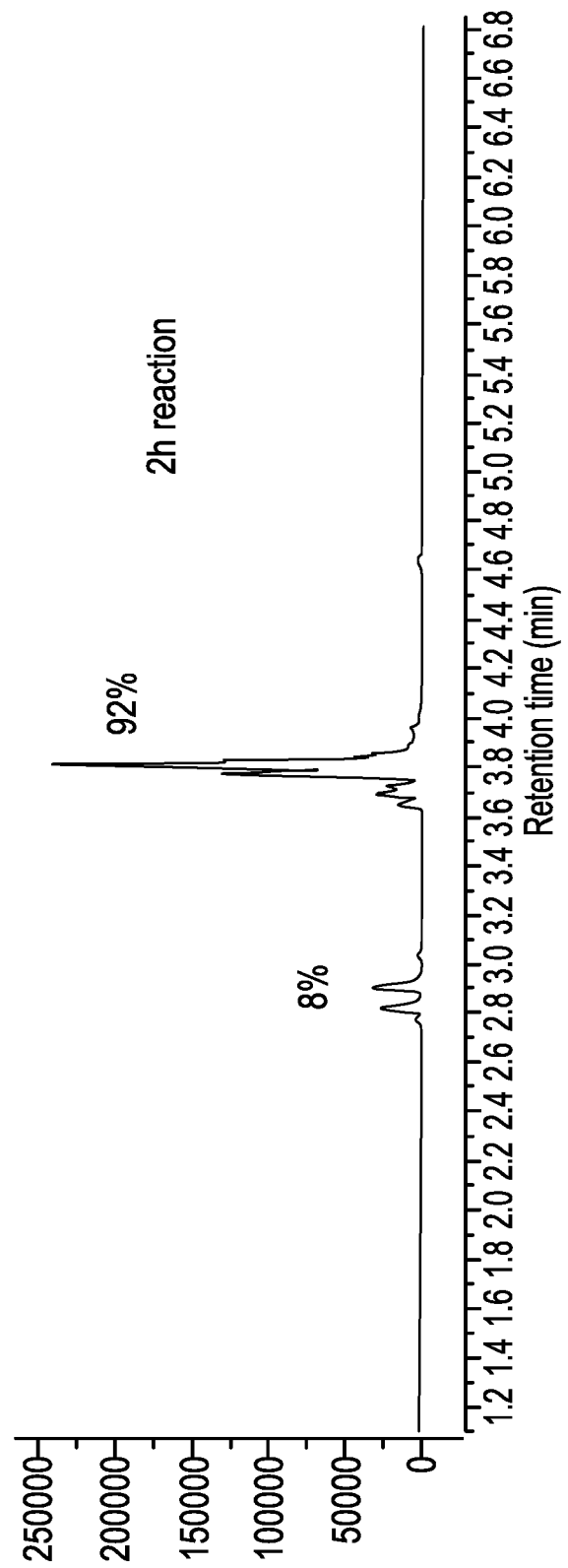
FIG. 6 provides the GCMS of the composition of Working Example 2.

In a glovebox under nitrogen atmosphere, TVCH (0.39 ml, 2.02 mmol), DEZ (0.052 ml, 0.505 mmol), TEA (0.276 ml, 2.02 mmol) and Co-catalyst A (0.362 ml of 0.0644 M solution in methylcyclohexane, 0.023 mmol) are mixed in 3 ml of toluene. Catalyst (A2) (10 mg, 0.02 mmol) is dissolved in 1 ml of toluene and added to the mixture to initiate the reaction and to form a final solution containing the composition of Working Example 2. After 2 hr, TVCH is all reacted as evidenced by the disappearance of vinyl peaks (4.8-6 ppm) on $^1$H NMR, as seen in FIG. 5. The solution is brownish and clear, showing no sign of gel formation. In addition, an aliquot of the final solution is quenched by water and analyzed by GCMS. As seen in FIG. 6, the GCMS shows a major group of peaks at 3.6-4.0 min (m/z=222),

What is claimed is:

1. A composition represented by formula (I) or (II):

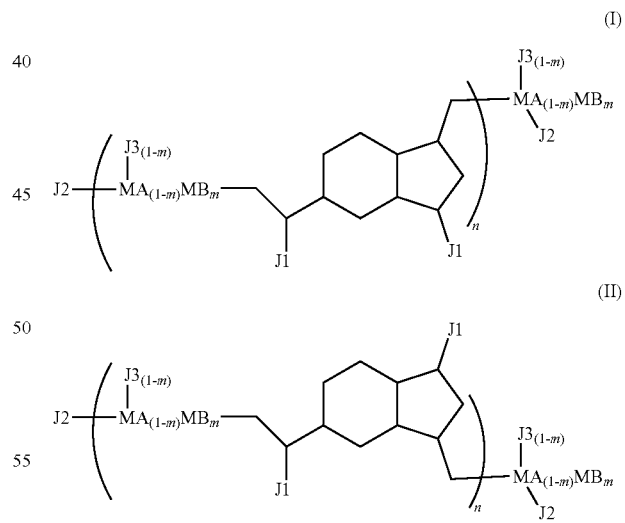

wherein:
each MA is Al, B, or Ga;
each MB is Zn or Mg;
m is a number from 0 to 1;
n is a number from 1 to 100; and
each J1, J2, and J3 is hydrogen or a $C_{1-20}$ alkyl group, and wherein J1, J2, and J3 may be the same or different.

2. The composition of claim 1, wherein each J1, J2, and J3 is selected from the group consisting of methyl, ethyl, n-propyl, n-butyl, isobutyl, n-hexyl, isohexyl, n-octyl, isooctyl, and isomers thereof.

3. A catalyst composition comprising a reaction product of at least one catalyst precursor, at least one co-catalyst, and the composition of claim 1.

4. A polymerization process for preparing a polymer composition comprising:
contacting at least one olefin monomer with a catalyst composition; wherein
the catalyst composition comprises a reaction product of a catalyst precursor, a co-catalyst, and the composition of claim 1.

5. A polymer composition obtained by the polymerization process of claim 4.

6. A process for preparing a telechelic functional polymer comprising performing functional group conversion reactions at carbon-metal bonds of the composition of claim 1.

7. A process for preparing a composition represented by formula (I) or (II):

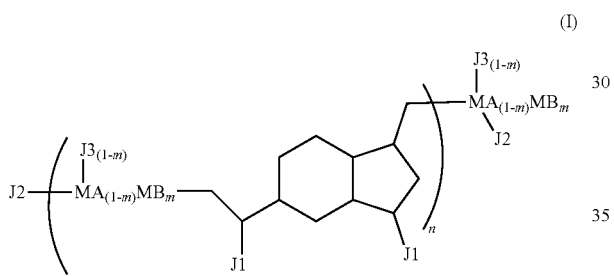

(I)

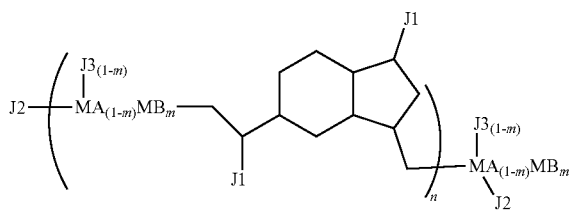

(II)

wherein:
each MA is Al, B, or Ga;
each MB is Zn or Mg;
m is a number from 0 to 1;
n is a number from 1 to 100; and
each J1, J2, and J3 is hydrogen or a $C_{1-20}$ alkyl group, and wherein J1, J2, and J3 may be the same or different, the process comprising: (a) combining 1,2,4-trivinylcyclohexane, an organometallic compound, a co-catalyst, a solvent, and a first catalyst precursor, and (b) obtaining a solution comprising the composition represented by formula (I) or (II).

8. The process of claim 7, wherein each J1, J2, and J3 is selected from the group consisting of methyl, ethyl, n-propyl, n-butyl, isobutyl, n-hexyl, isohexyl, n-octyl, isooctyl, and isomers thereof.

9. A polymerization process for preparing a polymer composition, the process comprising:
contacting at least one olefin monomer with a catalyst composition;
wherein the catalyst composition comprises a reaction product of a second catalyst precursor, a co-catalyst, and the composition prepared according to the process of claim 7, and
wherein the second catalyst precursor is a same compound as the first catalyst precursor.

* * * * *